United States Patent
Freund et al.

(10) Patent No.: US 12,157,776 B2
(45) Date of Patent: Dec. 3, 2024

(54) ANTI-PAPP-A ANTIBODIES AND METHODS OF USE THEREOF

(71) Applicants: Calico Life Sciences LLC, South San Francisco, CA (US); AbbVie Inc., North Chicago, IL (US)

(72) Inventors: Adam Freund, San Mateo, CA (US); Yuliya Kutskova, Northborough, MA (US); Jeffrey R. Barker, Holden, MA (US)

(73) Assignees: Calico Life Sciences LLC, South San Francisco, CA (US); AbbVie Inc., North Chicago, IL (US)

( * ) Notice: Subject to any disclaimer, the term of this patent is extended or adjusted under 35 U.S.C. 154(b) by 0 days.

(21) Appl. No.: 18/508,874

(22) Filed: Nov. 14, 2023

(65) Prior Publication Data

US 2024/0158534 A1    May 16, 2024

Related U.S. Application Data

(60) Provisional application No. 63/383,875, filed on Nov. 15, 2022.

(51) Int. Cl.
*C07K 16/40* (2006.01)

(52) U.S. Cl.
CPC .......... *C07K 16/40* (2013.01); *C07K 2317/52* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 6,172,198 B1 | 1/2001 | Sinosich |
| 6,500,630 B2 | 12/2002 | Conover et al. |
| 6,699,675 B2 | 3/2004 | Holmes et al. |
| 7,115,382 B1 | 10/2006 | Overgaard et al. |
| 7,220,892 B2 | 5/2007 | Conover et al. |
| 7,402,724 B2 | 7/2008 | Conover |
| 7,563,443 B2 | 7/2009 | Grant et al. |
| 7,723,049 B2 | 5/2010 | Conover et al. |
| 8,323,913 B2 | 12/2012 | Conover et al. |
| 8,653,020 B2 | 2/2014 | Oxvig et al. |
| 8,802,619 B2 | 8/2014 | Birnie |
| 9,983,215 B2 | 5/2018 | Speicher et al. |
| 2005/0009136 A1 | 1/2005 | Nixon et al. |
| 2005/0232863 A1 | 10/2005 | Conover |
| 2010/0310646 A1 | 12/2010 | Oxvig et al. |
| 2015/0132770 A1 | 5/2015 | Oxvig et al. |
| 2016/0024589 A1 | 1/2016 | Johannessen et al. |
| 2016/0175462 A1 | 6/2016 | Zhang et al. |
| 2016/0232293 A1 | 8/2016 | Godzik et al. |
| 2017/0315130 A1 | 11/2017 | Grobe et al. |
| 2022/0372167 A1 | 11/2022 | Chini |

FOREIGN PATENT DOCUMENTS

| | | |
|---|---|---|
| EP | 1169058 B1 | 5/2007 |
| EP | 1350109 B1 | 5/2009 |
| WO | 2009092806 A2 | 7/2009 |
| WO | 2014180485 A2 | 11/2014 |
| WO | 2018098363 A2 | 5/2018 |
| WO | 2018217945 A1 | 11/2018 |
| WO | 2019084033 A1 | 5/2019 |
| WO | 2020198166 A1 | 10/2020 |
| WO | 2021207152 A1 | 10/2021 |

OTHER PUBLICATIONS

Ulinski et al., 2000, Pediatr. Nephrol. 14:589-597.*
Wang et al., Dec. 22, 2021, Frontiers in Pharmacology 12:807119; pp. 1-7.*
EP 20777391.2 Extended European Search Report dated Nov. 25, 2022.
Kalousová, M., et al., Pregnancy-associated plasma protein A: spotlight on kidney diseases, Clin Chem Lab Med, 50(7): 1183-1190 (2012).
Kamenický, P., et al., Growth hormone, insulin-like growth factor-1, and the kidney: pathophysiological and clinical implications, Endocr Rev, 35(2): 234-281 (2014).
Kashyap, S., et al., Implications of the PAPP-A-IGFBP-IGF-1 pathway in the pathogenesis and treatment of polycystic kidney disease, Cell Signal, 73: 109698 (2020).
Kashyap, S., et al., Metalloproteinase PAPP-A regulation of IGF-1 contributes to polycystic kidney disease pathogenesis, JCI Insight, 5(4): e135700 (2020).
Mader, J.R., et al., Mice Deficient in PAPP-A Show Resistance to the Development of Diabetic Nephropathy, J Endocrinol, 219(1): 51-58 (2013).
Mohrin, M., et al., Inhibition of longevity regulator PAPP-A modulates tissue homeostasis via restraint of mesenchymal stromal cells, Aging Cell, 20(3): e13313 (2021).
PCT/US2020/024310 International Search Report and Written Opinion mailed Jul. 30, 2020.
PCT/US2023/079640 International Search Report and Written Opinion mailed Apr. 22, 2024.

* cited by examiner

*Primary Examiner* — Elizabeth C. Kemmerer
(74) *Attorney, Agent, or Firm* — Goodwin Procter LLP

(57) ABSTRACT

Provided herein are anti-PAPP-A antibodies. Also provided are methods of using such antibodies to treat PAPP-A associated disorders such as kidney disease.

9 Claims, 4 Drawing Sheets
Specification includes a Sequence Listing.

SEQUENCE LISTING

```
Sequence total quantity: 103
SEQ ID NO: 1            moltype = AA  length = 453
FEATURE                 Location/Qualifiers
source                  1..453
                        mol_type = protein
                        organism = synthetic construct
SEQUENCE: 1
EVQLVESGGG VVQPGRSLRL SCAASGFTFS SYAMHWVRQA PGKGLEWVAV ISYDGSIKYY    60
ADAVKGRFTI SRDNSKNTLY LQMNSLRAED TAVYYCARHN RIYSWGWHTF DIWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 2            moltype = AA  length = 123
FEATURE                 Location/Qualifiers
source                  1..123
```

```
                               mol_type = protein
                               organism = synthetic construct
SEQUENCE: 2
EVQLVESGGG  VVQPGRSLRL  SCAASGFTFS  SYAMHWVRQA  PGKGLEWVAV  ISYDGSIKYY    60
ADAVKGRFTI  SRDNSKNTLY  LQMNSLRAED  TAVYYCARHN  RIYSWGWHTF  DIWGQGTLVT   120
VSS                                                                      123

SEQ ID NO: 3                   moltype = AA   length = 5
FEATURE                        Location/Qualifiers
source                         1..5
                               mol_type = protein
                               organism = synthetic construct
SEQUENCE: 3
SYAMH                                                                      5

SEQ ID NO: 4                   moltype = AA   length = 17
FEATURE                        Location/Qualifiers
source                         1..17
                               mol_type = protein
                               organism = synthetic construct
SEQUENCE: 4
VISYDGSIKY YADAVKG                                                        17

SEQ ID NO: 5                   moltype = AA   length = 14
FEATURE                        Location/Qualifiers
source                         1..14
                               mol_type = protein
                               organism = synthetic construct
SEQUENCE: 5
HNRIYSWGWH TFDI                                                           14

SEQ ID NO: 6                   moltype = AA   length = 213
FEATURE                        Location/Qualifiers
source                         1..213
                               mol_type = protein
                               organism = synthetic construct
SEQUENCE: 6
IQMTQSPSSL  SASVGDRVTI  TCRASQDISI  YLNWYQQKPG  KAPKLLIYGA  SSLQSGVPSR    60
FSGSGSGTDF  TLTISSLQPE  DFATYYCQQA  DAGPWKFGGG  TKVEIKRTVA  APSVFIFPPS   120
DEQLKSGTAS  VVCLLNNFYP  REAKVQWKVD  NALQSGNSQE  SVTEQDSKDS  TYSLSSTLTL   180
SKADYEKHKV  YACEVTHQGL  SSPVTKSFNR  GEC                                  213

SEQ ID NO: 7                   moltype = AA   length = 107
FEATURE                        Location/Qualifiers
source                         1..107
                               mol_type = protein
                               organism = synthetic construct
SEQUENCE: 7
DIQMTQSPSS  LSASVGDRVT  ITCRASQDIS  IYLNWYQQKP  GKAPKLLIYG  ASSLQSGVPS    60
RFSGSGSGTD  FTLTISSLQP  EDFATYYCQQ  ADAGPWKFGG  GTKVEIK                  107

SEQ ID NO: 8                   moltype = AA   length = 11
FEATURE                        Location/Qualifiers
source                         1..11
                               mol_type = protein
                               organism = synthetic construct
SEQUENCE: 8
RASQDISIYL N                                                              11

SEQ ID NO: 9                   moltype = AA   length = 7
FEATURE                        Location/Qualifiers
source                         1..7
                               mol_type = protein
                               organism = synthetic construct
SEQUENCE: 9
GASSLQS                                                                    7

SEQ ID NO: 10                  moltype = AA   length = 9
FEATURE                        Location/Qualifiers
source                         1..9
                               mol_type = protein
                               organism = synthetic construct
SEQUENCE: 10
QQADAGPWK                                                                  9

SEQ ID NO: 11                  moltype = AA   length = 453
FEATURE                        Location/Qualifiers
source                         1..453
                               mol_type = protein
```

```
                                organism = synthetic construct
SEQUENCE: 11
EVQLVESGGG VVQPGRSLRL SCAASGFTFS SYAMHWVRQA PGKGLEWVAV ISYDGSIKYY   60
ADAVKGRFTI SRDNSKNTLY LQMNSLRAED TAVYYCARHE RIPPWGFHTF DIWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 12           moltype = AA  length = 123
FEATURE                 Location/Qualifiers
source                  1..123
                        mol_type = protein
                        organism = synthetic construct
SEQUENCE: 12
EVQLVESGGG VVQPGRSLRL SCAASGFTFS SYAMHWVRQA PGKGLEWVAV ISYDGSIKYY   60
ADAVKGRFTI SRDNSKNTLY LQMNSLRAED TAVYYCARHE RIPPWGFHTF DIWGQGTLVT  120
VSS                                                                123

SEQ ID NO: 13           moltype = AA  length = 5
FEATURE                 Location/Qualifiers
source                  1..5
                        mol_type = protein
                        organism = synthetic construct
SEQUENCE: 13
SYAMH                                                                5

SEQ ID NO: 14           moltype = AA  length = 17
FEATURE                 Location/Qualifiers
source                  1..17
                        mol_type = protein
                        organism = synthetic construct
SEQUENCE: 14
VISYDGSIKY YADAVKG                                                  17

SEQ ID NO: 15           moltype = AA  length = 14
FEATURE                 Location/Qualifiers
source                  1..14
                        mol_type = protein
                        organism = synthetic construct
SEQUENCE: 15
HERIPPWGFH TFDI                                                     14

SEQ ID NO: 16           moltype = AA  length = 214
FEATURE                 Location/Qualifiers
source                  1..214
                        mol_type = protein
                        organism = synthetic construct
SEQUENCE: 16
DIQMTQSPSS LSASVGDRVT ITCRASQGIS IYLNWYQQKP GKAPKLLIYG ASSLQSGVPS   60
RFSGSGSGTD FTLTISSLQP EDFATYYCQQ SDGTPWTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 17           moltype = AA  length = 107
FEATURE                 Location/Qualifiers
source                  1..107
                        mol_type = protein
                        organism = synthetic construct
SEQUENCE: 17
DIQMTQSPSS LSASVGDRVT ITCRASQGIS IYLNWYQQKP GKAPKLLIYG ASSLQSGVPS   60
RFSGSGSGTD FTLTISSLQP EDFATYYCQQ SDGTPWTFGG GTKVEIK                107

SEQ ID NO: 18           moltype = AA  length = 11
FEATURE                 Location/Qualifiers
source                  1..11
                        mol_type = protein
                        organism = synthetic construct
SEQUENCE: 18
RASQGISIYL N                                                        11

SEQ ID NO: 19           moltype = AA  length = 7
FEATURE                 Location/Qualifiers
source                  1..7
                        mol_type = protein
                        organism = synthetic construct
SEQUENCE: 19
```

```
SEQ ID NO: 20            moltype = AA   length = 9
FEATURE                  Location/Qualifiers
source                   1..9
                         mol_type = protein
                         organism = synthetic construct
SEQUENCE: 20
QQSDGTPWT                                                                    9

SEQ ID NO: 21            moltype = AA   length = 447
FEATURE                  Location/Qualifiers
source                   1..447
                         mol_type = protein
                         organism = synthetic construct
SEQUENCE: 21
EVQLVESGGG VVQPGRSLRL SCAASGFTFS SYGMHWVRQA PGKGLEWVAV ISYDGRNKYY          60
ADAVKGRFTI SRDNSKNTLY LQMNSLRAED TAVYYCARYK PMPFDVWGQG TLVTVSSAST         120
KGPSVFPLAP SSKSTSGGTA ALGCLVKDYF PEPVTVSWNS GALTSGVHTF PAVLQSSGLY         180
SLSSVVTVPS SSLGTQTYIC NVNHKPSNTK VDKKVEPKSC DKTHTCPPCP APEAAGGPSV         240
FLFPPKPKDT LMISRTPEVT CVVVDVSHED PEVKFNWYVD GVEVHNAKTK PREEQYNSTY         300
RVVSVLTVLH QDWLNGKEYK CKVSNKALPA PIEKTISKAK GQPREPQVYT LPPSREEMTK         360
NQVSLTCLVK GFYPSDIAVE WESNGQPENN YKTTPPVLDS DGSFFLYSKL TVDKSRWQQG         420
NVFSCSVMHE ALHNHYTQKS LSLSPGK                                            447

SEQ ID NO: 22            moltype = AA   length = 117
FEATURE                  Location/Qualifiers
source                   1..117
                         mol_type = protein
                         organism = synthetic construct
SEQUENCE: 22
EVQLVESGGG VVQPGRSLRL SCAASGFTFS SYGMHWVRQA PGKGLEWVAV ISYDGRNKYY          60
ADAVKGRFTI SRDNSKNTLY LQMNSLRAED TAVYYCARYK PMPFDVWGQG TLVTVSS           117

SEQ ID NO: 23            moltype = AA   length = 5
FEATURE                  Location/Qualifiers
source                   1..5
                         mol_type = protein
                         organism = synthetic construct
SEQUENCE: 23
SYGMH                                                                        5

SEQ ID NO: 24            moltype = AA   length = 17
FEATURE                  Location/Qualifiers
source                   1..17
                         mol_type = protein
                         organism = synthetic construct
SEQUENCE: 24
VISYDGRNKY YADAVKG                                                          17

SEQ ID NO: 25            moltype = AA   length = 8
FEATURE                  Location/Qualifiers
source                   1..8
                         mol_type = protein
                         organism = synthetic construct
SEQUENCE: 25
YKPMPFDV                                                                     8

SEQ ID NO: 26            moltype = AA   length = 214
FEATURE                  Location/Qualifiers
source                   1..214
                         mol_type = protein
                         organism = synthetic construct
SEQUENCE: 26
DIQMTQSPSS LSASVGDRVT ITCRASQSIS SYLNWYQQKP GKAPKLLIYE ASILQSGVPS          60
RFSGSGSGTD FTLTISSLQP EDFATYYCGQ SYYTPFPFGG GTKVEIKRTV AAPSVFIFPP         120
SDEQLKSGTA SVVCLLNNFY PREAKVQWKV DNALQSGNSQ ESVTEQDSKD STYSLSSTLT         180
LSKADYEKHK VYACEVTHQG LSSPVTKSFN RGEC                                    214

SEQ ID NO: 27            moltype = AA   length = 107
FEATURE                  Location/Qualifiers
source                   1..107
                         mol_type = protein
                         organism = synthetic construct
SEQUENCE: 27
DIQMTQSPSS LSASVGDRVT ITCRASQSIS SYLNWYQQKP GKAPKLLIYE ASILQSGVPS          60
RFSGSGSGTD FTLTISSLQP EDFATYYCGQ SYYTPFPFGG GTKVEIK                      107

SEQ ID NO: 28            moltype = AA   length = 11
```

| | | |
|---|---|---|
| FEATURE | Location/Qualifiers | |
| source | 1..11<br>mol_type = protein<br>organism = synthetic construct | |
| SEQUENCE: 28 | | |
| RASQSISSYL N | | 11 |
| | | |
| SEQ ID NO: 29 | moltype = AA  length = 7 | |
| FEATURE | Location/Qualifiers | |
| source | 1..7<br>mol_type = protein<br>organism = synthetic construct | |
| SEQUENCE: 29 | | |
| EASILQS | | 7 |
| | | |
| SEQ ID NO: 30 | moltype = AA  length = 9 | |
| FEATURE | Location/Qualifiers | |
| source | 1..9<br>mol_type = protein<br>organism = synthetic construct | |
| SEQUENCE: 30 | | |
| GQSYYTPFP | | 9 |
| | | |
| SEQ ID NO: 31 | moltype = AA  length = 447 | |
| FEATURE | Location/Qualifiers | |
| source | 1..447<br>mol_type = protein<br>organism = synthetic construct | |
| SEQUENCE: 31 | | |
| EVQLVESGGG VVQPGRSLRL SCAASGFAFS TYGMHWVRQA PGKGLEWVAV IRYDGQEKYY | | 60 |
| ADAVKGRFTI SRDNSKNTLY LQMNSLRAED TAVYYCARYK PMPFDVWGQG TLVTVSSAST | | 120 |
| KGPSVFPLAP SSKSTSGGTA ALGCLVKDYF PEPVTVSWNS GALTSGVHTF PAVLQSSGLY | | 180 |
| SLSSVVTVPS SSLGTQTYIC NVNHKPSNTK VDKKVEPKSC DKTHTCPPCP APEAAGGPSV | | 240 |
| FLFPPKPKDT LMISRTPEVT CVVVDVSHED PEVKFNWYVD GVEVHNAKTK PREEQYNSTY | | 300 |
| RVVSVLTVLH QDWLNGKEYK CKVSNKALPA PIEKTISKAK GQPREPQVYT LPPSREEMTK | | 360 |
| NQVSLTCLVK GFYPSDIAVE WESNGQPENN YKTTPPVLDS DGSFFLYSKL TVDKSRWQQG | | 420 |
| NVFSCSVMHE ALHNHYTQKS LSLSPGK | | 447 |
| | | |
| SEQ ID NO: 32 | moltype = AA  length = 117 | |
| FEATURE | Location/Qualifiers | |
| source | 1..117<br>mol_type = protein<br>organism = synthetic construct | |
| SEQUENCE: 32 | | |
| EVQLVESGGG VVQPGRSLRL SCAASGFAFS TYGMHWVRQA PGKGLEWVAV IRYDGQEKYY | | 60 |
| ADAVKGRFTI SRDNSKNTLY LQMNSLRAED TAVYYCARYK PMPFDVWGQG TLVTVSS | | 117 |
| | | |
| SEQ ID NO: 33 | moltype = AA  length = 5 | |
| FEATURE | Location/Qualifiers | |
| source | 1..5<br>mol_type = protein<br>organism = synthetic construct | |
| SEQUENCE: 33 | | |
| TYGMH | | 5 |
| | | |
| SEQ ID NO: 34 | moltype = AA  length = 17 | |
| FEATURE | Location/Qualifiers | |
| source | 1..17<br>mol_type = protein<br>organism = synthetic construct | |
| SEQUENCE: 34 | | |
| VIRYDGQEKY YADAVKG | | 17 |
| | | |
| SEQ ID NO: 35 | moltype = AA  length = 8 | |
| FEATURE | Location/Qualifiers | |
| source | 1..8<br>mol_type = protein<br>organism = synthetic construct | |
| SEQUENCE: 35 | | |
| YKPMPFDV | | 8 |
| | | |
| SEQ ID NO: 36 | moltype = AA  length = 214 | |
| FEATURE | Location/Qualifiers | |
| source | 1..214<br>mol_type = protein<br>organism = synthetic construct | |
| SEQUENCE: 36 | | |
| DIQMTQSPSS LSASVGDRVT ITCRASQSIS RYLNWYQQKP GKAPKLLIYA ASILQSGVPS | | 60 |
| RFSGSGSGTD FTLTISSLQP EDFATYYCQQ SHPTPFTFGG GTKVEIKRTV AAPSVFIFPP | | 120 |

```
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 37              moltype = AA   length = 107
FEATURE                    Location/Qualifiers
source                     1..107
                           mol_type = protein
                           organism = synthetic construct
SEQUENCE: 37
DIQMTQSPSS LSASVGDRVT ITCRASQSIS RYLNWYQQKP GKAPKLLIYA ASILQSGVPS    60
RFSGSGSGTD FTLTISSLQP EDFATYYCQQ SHPTPFTFGG GTKVEIK                  107

SEQ ID NO: 38              moltype = AA   length = 11
FEATURE                    Location/Qualifiers
source                     1..11
                           mol_type = protein
                           organism = synthetic construct
SEQUENCE: 38
RASQSISRYL N                                                         11

SEQ ID NO: 39              moltype = AA   length = 7
FEATURE                    Location/Qualifiers
source                     1..7
                           mol_type = protein
                           organism = synthetic construct
SEQUENCE: 39
AASILQS                                                              7

SEQ ID NO: 40              moltype = AA   length = 9
FEATURE                    Location/Qualifiers
source                     1..9
                           mol_type = protein
                           organism = synthetic construct
SEQUENCE: 40
QQSHPTPFT                                                            9

SEQ ID NO: 41              moltype = AA   length = 447
FEATURE                    Location/Qualifiers
source                     1..447
                           mol_type = protein
                           organism = synthetic construct
SEQUENCE: 41
EVQLVESGGG VVQPGRSLRL SCAASGFTFS SYGMHWVRQA PGKGLEWVAV IYYDGRRKYY    60
ADSVKGRFTI SRDNSKNTLY LQMNSLRAED TAVYYCARAD MHRFDVWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APEAAGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSREEMTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                        447

SEQ ID NO: 42              moltype = AA   length = 117
FEATURE                    Location/Qualifiers
source                     1..117
                           mol_type = protein
                           organism = synthetic construct
SEQUENCE: 42
EVQLVESGGG VVQPGRSLRL SCAASGFTFS SYGMHWVRQA PGKGLEWVAV IYYDGRRKYY    60
ADSVKGRFTI SRDNSKNTLY LQMNSLRAED TAVYYCARAD MHRFDVWGQG TLVTVSS      117

SEQ ID NO: 43              moltype = AA   length = 5
FEATURE                    Location/Qualifiers
source                     1..5
                           mol_type = protein
                           organism = synthetic construct
SEQUENCE: 43
SYGMH                                                                5

SEQ ID NO: 44              moltype = AA   length = 17
FEATURE                    Location/Qualifiers
source                     1..17
                           mol_type = protein
                           organism = synthetic construct
SEQUENCE: 44
VIYYDGRRKY YADSVKG                                                   17

SEQ ID NO: 45              moltype = AA   length = 8
FEATURE                    Location/Qualifiers
source                     1..8
```

```
                              mol_type = protein
                              organism = synthetic construct
SEQUENCE: 45
ADMHRFDV                                                                    8

SEQ ID NO: 46         moltype = AA   length = 214
FEATURE               Location/Qualifiers
source                1..214
                      mol_type = protein
                      organism = synthetic construct
SEQUENCE: 46
DIQMTQSPSS LSASVGDRVT ITCRASQDII SYLNWYQQKP GKAPKLLIYV ASSLQSGVPS            60
RFSGSGSGTD FTLTISSLQP EDFATYYCQQ SYSPPYTFGG GTKVEIKRTV AAPSVFIFPP           120
SDEQLKSGTA SVVCLLNNFY PREAKVQWKV DNALQSGNSQ ESVTEQDSKD STYSLSSTLT           180
LSKADYEKHK VYACEVTHQG LSSPVTKSFN RGEC                                      214

SEQ ID NO: 47         moltype = AA   length = 107
FEATURE               Location/Qualifiers
source                1..107
                      mol_type = protein
                      organism = synthetic construct
SEQUENCE: 47
DIQMTQSPSS LSASVGDRVT ITCRASQDII SYLNWYQQKP GKAPKLLIYV ASSLQSGVPS            60
RFSGSGSGTD FTLTISSLQP EDFATYYCQQ SYSPPYTFGG GTKVEIK                        107

SEQ ID NO: 48         moltype = AA   length = 11
FEATURE               Location/Qualifiers
source                1..11
                      mol_type = protein
                      organism = synthetic construct
SEQUENCE: 48
RASQDIISYL N                                                               11

SEQ ID NO: 49         moltype = AA   length = 7
FEATURE               Location/Qualifiers
source                1..7
                      mol_type = protein
                      organism = synthetic construct
SEQUENCE: 49
VASSLQS                                                                     7

SEQ ID NO: 50         moltype = AA   length = 9
FEATURE               Location/Qualifiers
source                1..9
                      mol_type = protein
                      organism = synthetic construct
SEQUENCE: 50
QQSYSPPYT                                                                   9

SEQ ID NO: 51         moltype = AA   length = 448
FEATURE               Location/Qualifiers
source                1..448
                      mol_type = protein
                      organism = synthetic construct
SEQUENCE: 51
EVQLLESGGG LVQPGGSLRL SCAASGFTFS SYAMSWVRQA PGKGLEWVSA ISMTVGRTYY            60
ADSVKGRFTI SRDNSKNTLY LQMNSLRAED TAVYYCARVW GGVRFDVWGQ GTLVTVSSAS           120
TKGPSVFPLA PSSKSTSGGT AALGCLVKDY FPEPVTVSWN SGALTSGVHT FPAVLQSSGL           180
YSLSSVVTVP SSSLGTQTYI CNVNHKPSNT KVDKKVEPKS CDKTHTCPPC PAPEAAGGPS           240
VFLFPPKPKD TLMISRTPEV TCVVVDVSHE DPEVKFNWYV DGVEVHNAKT KPREEQYNST           300
YRVVSVLTVL HQDWLNGKEY KCKVSNKALP APIEKTISKA KGQPREPQVY TLPPSREEMT           360
KNQVSLTCLV KGFYPSDIAV EWESNGQPEN NYKTTPPVLD SDGSFFLYSK LTVDKSRWQQ           420
GNVFSCSVMH EALHNHYTQK SLSLSPGK                                             448

SEQ ID NO: 52         moltype = AA   length = 118
FEATURE               Location/Qualifiers
source                1..118
                      mol_type = protein
                      organism = synthetic construct
SEQUENCE: 52
EVQLLESGGG LVQPGGSLRL SCAASGFTFS SYAMSWVRQA PGKGLEWVSA ISMTVGRTYY            60
ADSVKGRFTI SRDNSKNTLY LQMNSLRAED TAVYYCARVW GGVRFDVWGQ GTLVTVSS             118

SEQ ID NO: 53         moltype = AA   length = 5
FEATURE               Location/Qualifiers
source                1..5
                      mol_type = protein
                      organism = synthetic construct
SEQUENCE: 53
```

```
SYAMS                                                                       5

SEQ ID NO: 54           moltype = AA  length = 17
FEATURE                 Location/Qualifiers
source                  1..17
                        mol_type = protein
                        organism = synthetic construct
SEQUENCE: 54
AISMTVGRTY YADSVKG                                                         17

SEQ ID NO: 55           moltype = AA  length = 9
FEATURE                 Location/Qualifiers
source                  1..9
                        mol_type = protein
                        organism = synthetic construct
SEQUENCE: 55
QQSSSTPWT                                                                   9

SEQ ID NO: 56           moltype = AA  length = 214
FEATURE                 Location/Qualifiers
source                  1..214
                        mol_type = protein
                        organism = synthetic construct
SEQUENCE: 56
DIQMTQSPSS LSASVGDRVT ITCRASQSIS TYLNWYQQKP GKAPKLLIYV ASILQSGVPS           60
RFSGSGSGTD FTLTISSLQP EDFATYYCQQ SSSTPWTFGG GTKVEIKRTV AAPSVFIFPP          120
SDEQLKSGTA SVVCLLNNFY PREAKVQWKV DNALQSGNSQ ESVTEQDSKD STYSLSSTLT          180
LSKADYEKHK VYACEVTHQG LSSPVTKSFN RGEC                                     214

SEQ ID NO: 57           moltype = AA  length = 107
FEATURE                 Location/Qualifiers
source                  1..107
                        mol_type = protein
                        organism = synthetic construct
SEQUENCE: 57
DIQMTQSPSS LSASVGDRVT ITCRASQSIS TYLNWYQQKP GKAPKLLIYV ASILQSGVPS           60
RFSGSGSGTD FTLTISSLQP EDFATYYCQQ SSSTPWTFGG GTKVEIK                       107

SEQ ID NO: 58           moltype = AA  length = 11
FEATURE                 Location/Qualifiers
source                  1..11
                        mol_type = protein
                        organism = synthetic construct
SEQUENCE: 58
RASQSISTYL N                                                               11

SEQ ID NO: 59           moltype = AA  length = 7
FEATURE                 Location/Qualifiers
source                  1..7
                        mol_type = protein
                        organism = synthetic construct
SEQUENCE: 59
VASILQS                                                                     7

SEQ ID NO: 60           moltype = AA  length = 9
FEATURE                 Location/Qualifiers
source                  1..9
                        mol_type = protein
                        organism = synthetic construct
SEQUENCE: 60
QQSSSTPWT                                                                   9

SEQ ID NO: 61           moltype = AA  length = 446
FEATURE                 Location/Qualifiers
source                  1..446
                        mol_type = protein
                        organism = synthetic construct
SEQUENCE: 61
VQLVESGGGV VQPGRSLRLS CAASGFTFSS YAMHWVRQAP GKGLEWVAVI SYDGSIKYYA           60
DAVKGRFTIS RDNSKNTLYL QMNSLRAEDT AVYYCARHNR IYSWGWHTFD IWGQGTLVTV          120
SSAKTTPPSV YPLAPGSAAQ TNSMVTLGCL VKGYFPEPVT VTWNSGSLSS GVHTFPAVLQ          180
SDLYTLSSSV TVPSSTWPSQ TVTCNVAHPA SSTKVDKKIV PRDCGCKPCI CTVPEVSSVF          240
IFPPKPKDVL TITLTPKVTC VVVDISKDDP EVQFSWFVDD VEVHTAQTKP REEQINSTFR          300
SVSELPIMHQ DWLNGKEFKC RVNSAAFPAP IEKTISKTKG RPKAPQVYTI PPPKEQMAKD          360
KVSLTCMITN FFPEDITVEW QWNGQPAENY KNTQPIMDTD GSYFVYSKLN VQKSNWEAGN          420
TFTCSVLHEG LHNHHTEKSL SHSPGK                                              446

SEQ ID NO: 62           moltype = AA  length = 123
FEATURE                 Location/Qualifiers
```

```
                        source                  1..123
                                                mol_type = protein
                                                organism = synthetic construct
SEQUENCE: 62
EVQLVESGGG VVQPGRSLRL SCAASGFTFS SYAMHWVRQA PGKGLEWVAV ISYDGSIKYY    60
ADAVKGRFTI SRDNSKNTLY LQMNSLRAED TAVYYCARHN RIYSWGWHTF DIWGQGTLVT   120
VSS                                                                 123

SEQ ID NO: 63           moltype = AA  length = 5
FEATURE                 Location/Qualifiers
source                  1..5
                        mol_type = protein
                        organism = synthetic construct
SEQUENCE: 63
SYAMH                                                                 5

SEQ ID NO: 64           moltype = AA  length = 17
FEATURE                 Location/Qualifiers
source                  1..17
                        mol_type = protein
                        organism = synthetic construct
SEQUENCE: 64
VISYDGSIKY YADAVKG                                                   17

SEQ ID NO: 65           moltype = AA  length = 14
FEATURE                 Location/Qualifiers
source                  1..14
                        mol_type = protein
                        organism = synthetic construct
SEQUENCE: 65
HNRIYSWGWH TFDI                                                      14

SEQ ID NO: 66           moltype = AA  length = 214
FEATURE                 Location/Qualifiers
source                  1..214
                        mol_type = protein
                        organism = synthetic construct
SEQUENCE: 66
DIQMTQSPSS LSASVGDRVT ITCRASQDIS IYLNWYQQKP GKAPKLLIYG ASSLQSGVPS    60
RFSGSGSGTD FTLTISSLQP EDFATYYCQQ ADAGPWKFGG GTKVEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214

SEQ ID NO: 67           moltype = AA  length = 107
FEATURE                 Location/Qualifiers
source                  1..107
                        mol_type = protein
                        organism = synthetic construct
SEQUENCE: 67
DIQMTQSPSS LSASVGDRVT ITCRASQDIS IYLNWYQQKP GKAPKLLIYG ASSLQSGVPS    60
RFSGSGSGTD FTLTISSLQP EDFATYYCQQ ADAGPWKFGG GTKVEIK                 107

SEQ ID NO: 68           moltype = AA  length = 11
FEATURE                 Location/Qualifiers
source                  1..11
                        mol_type = protein
                        organism = synthetic construct
SEQUENCE: 68
RASQDISIYL N                                                         11

SEQ ID NO: 69           moltype = AA  length = 7
FEATURE                 Location/Qualifiers
source                  1..7
                        mol_type = protein
                        organism = synthetic construct
SEQUENCE: 69
GASSLQS                                                               7

SEQ ID NO: 70           moltype = AA  length = 9
FEATURE                 Location/Qualifiers
source                  1..9
                        mol_type = protein
                        organism = synthetic construct
SEQUENCE: 70
QQADAGPWK                                                             9

SEQ ID NO: 71           moltype = AA  length = 445
FEATURE                 Location/Qualifiers
source                  1..445
```

```
                        mol_type =  protein
                        organism =  synthetic construct
SEQUENCE: 71
EVQLLESGGD LVRPGGSLRL SCAASGFSFS RYGMSWVRQA PGKGLDWVAH ISASAGATYY    60
ADSVKGRFTI SRDNSKNTLF LQMNNLRADD TAIYYCAKGG KQWLIPWFDP WGQGTLVTVS   120
SAKTTPPSVY PLAPGSAAQT NSMVTLGCLV KGYFPEPVTV TWNSGSLSSG VHTFPAVLQS   180
DLYTLSSSVT VPSSTWPSET VTCNVAHPAS STKVDKKIVP RDCGCKPCIC TVPEVSSVFI   240
FPPKPKDVLT ITLTPKVTCV VVDISKDDPE VQFSWFVDDV EVHTAQTQPR EEQFNSTFRS   300
VSELPIMHQD WLNGKEFKCR VNSAAFPAPI EKTISKTKGR PKAPQVYTIP PPKEQMAKDK   360
VSLTCMITDF FPEDITVEWQ WNGQPAENYK NTQPIMDTDG SYFVYSKLNV QKSNWEAGNT   420
FTCSVLHEGL HNHHTEKSLS HSPGK                                        445

SEQ ID NO: 72           moltype =  AA  length =  214
FEATURE                 Location/Qualifiers
source                  1..214
                        mol_type =  protein
                        organism =  synthetic construct
SEQUENCE: 72
DIQMTQSPSS VSASVGDRVT IACRASQDIS DRLAWYQQKP GKVPKVLIYG ASSLQSGVPS    60
RFSGSGSGTD FTLTINSLQP EDFATYYCQQ ANSFPLTFGG GTKVEMKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214

SEQ ID NO: 73           moltype =     length =
SEQUENCE: 73
000

SEQ ID NO: 74           moltype =  AA  length =  17
FEATURE                 Location/Qualifiers
source                  1..17
                        mol_type =  protein
                        organism =  synthetic construct
SEQUENCE: 74
XIXXXXXXXY YADXVKG                                                   17

SEQ ID NO: 75           moltype =  AA  length =  14
FEATURE                 Location/Qualifiers
source                  1..14
                        mol_type =  protein
                        organism =  synthetic construct
SEQUENCE: 75
HXRIXXWGXH TFDI                                                      14

SEQ ID NO: 76           moltype =  AA  length =  11
FEATURE                 Location/Qualifiers
source                  1..11
                        mol_type =  protein
                        organism =  synthetic construct
SEQUENCE: 76
RASQXIXXYL N                                                         11

SEQ ID NO: 77           moltype =  AA  length =  7
FEATURE                 Location/Qualifiers
source                  1..7
                        mol_type =  protein
                        organism =  synthetic construct
SEQUENCE: 77
XASXLQS                                                               7

SEQ ID NO: 78           moltype =     length =
SEQUENCE: 78
000

SEQ ID NO: 79           moltype =  AA  length =  1627
FEATURE                 Location/Qualifiers
source                  1..1627
                        mol_type =  protein
                        organism =  Homo sapiens
SEQUENCE: 79
MRLWSWVLHL GLLSAALGCG LAERPRRARR DPRAGRPPRP AAGPATCATR AARGRRASPP    60
PPPPPGGAWE AVRVPRRRQQ REARGATEEP SPPSRALYFS GREGQLRLRA DLELPRDAFT   120
LQVWLRAEGG QRSPAVITGL YDKCSYISRD RGWVVGIHTI SDQDNKDPRY FFSLKTDRAR   180
QVTTINAHRS YLPGQWVYLA ATYDGQFMKL YVNGAQVATS GEQVGGIFSP LTQKCKVLML   240
GGSALNHNYR GYIEHFSLWK VARTQREILS DMETHGAHTA LPQLLLQENW DNVKHAWSPM   300
KDGSSPKVEF SNAHGFLLDT SLEPPLCGQT LCDNTEVIAS YNQLSSFRQP KVVRYRVVNL   360
YEDDHKNPTV TREQVDFQHH QLAEAFKQYN ISWELDVLEV SNSSLRRRLI LANCDISKIG   420
DENCDPECNH TLTGHDGGDC RHLRHPAFVK KQHNGVCDMD CNYERFNFDG GECCDPEITN   480
VTQTCFDPDS PHRAYLDVNE LKNILKLDGS THLNIFFAKS SEEELAGVAT WPWDKEALMH   540
LGGIVLNPSF YGMPGHTHTM IHEIGHSLGL YHVFRGISEI QSCSDPCMET EPSFETGDLC   600
```

-continued

```
NDTNPAPKHK SCGDPGPGND TCGFHSFFNT PYNNFMSYAD DDCTDSFTPN QVARMHCYLD   660
LVYQGWQPSR KPAPVALAPQ VLGHTTDSVT LEWFPPIDGH FFERELGSAC HLCLEGRILV   720
QYASNASSPM PCSPSGHWSP REAEGHPDVE QPCKSSVRTW SPNSAVNPHT VPPACPEPQG   780
CYLELEFLYP LVPESLTIWV TFVSTDWDSS GAVNDIKLLA VSGKNISLGP QNVFCDVPLT   840
IRLWDVGEEV YGIQIYTLDE HLEIDAAMLT STADTPLCLQ CKPLKYKVVR DPPLQMDVAS   900
ILHLNRKFVD MDLNLGSVYQ YWVITISGTE ESEPSPAVTY IHGSGYCGDG IIQKDQGEQC   960
DDDMNKINGDG CSLFCRQEVS FNCIDEPSRC YFHDGDGVCE EFEQKTSIKD CGVYTPQGFL  1020
DQWASNASVS HQDQQCPGWV IIGQPAASQV CRTKVIDLSE GISQHAWYPC TISYPYSQLA  1080
QTTFWLRAYF SQPMVAAAVI VHLVTDGTYY GDQKQETISV QLLDTKDQSH DLGLHVLSCR  1140
NNPLIIPVVH DLSQPFYHSQ AVRVSFSSPL VAISGVALRS FDNFDPVTLS SCQRGETYSP  1200
AEQSCVHFAC EKTDCPELAV ENASLNCSSS DRYHGAQCTV SCRTGYVLQI RRDDELIKSQ  1260
TGPSVTVTCT EGKWNKQVAC EPVDCSIPDH HQVYAASFSC PEGTTFGSQC SFQCRHPAQL  1320
KGNNSLLTCM EDGLWSFPEA LCELMCLAPP PVPNADLQTA RCRENKHKVG SFCKYKCKPG  1380
YHVPGSSRKS KKRAFKTQCT QDGSWQEGAC VPVTCDPPPP KFHGLYQCTN GFQFNSECRI  1440
KCEDSDASQG LGSNVIHCRK DGTWNGSFHV CQEMQGQCSV PNELNSNLKL QCPDGYAIGS  1500
ECATSCLDHN SESIILPMNV TVRDIPHWLN PTRVERVVCT AGLKWYPHPA LIHCVKGCEP  1560
FMGDNYCDAI NNRAFCNYDG GDCCTSTVKT KKVTPFPMSC DLQGDCACRD PQAQEHSRKD  1620
LRGYSHG                                                          1627

SEQ ID NO: 80           moltype = DNA   length = 1359
FEATURE                 Location/Qualifiers
source                  1..1359
                        mol_type = other DNA
                        organism = synthetic construct
SEQUENCE: 80
gaggtgcagc tggtggagtc tggtggaggc gtggtccagc ctgggcgctc cctgagactc    60
tcctgtgcag cctctggatt caccttcagt agctatgcca tgcactgggt ccgccaggct   120
ccaggcaagg gtctggagtg ggtggcagtg atatcctacg atggaagcat caagtactat   180
gcagacgccg tgaagggccg attcaccatc tccagagaca attccaagaa cacgctgtat   240
ctgcaaatga acagcctgag agctgaggac acggccgtgt attactgtgc agagacacaac  300
cgcatctact cctggggctg gcacaccttt gacatctggg gccaaggaac cctggtcacc   360
gtctcctcag cgtcgaccaa gggcccatcg gtcttccccc tggcaccctc ctccaagagc   420
acctctgggg gcacagcggc cctgggctgc ctggtcaagg actacttccc cgaaccggtg   480
acggtgtcgt ggaactcagg cgccctgacc agcggcgtgc acaccttccc ggctgtccta   540
cagtcctcag gactctactc cctcagcagc gtggtgaccg tgccctccag cagcttgggc   600
acccagacct acatctgcaa cgtgaatcac aagcccagca acaccaaggt ggacaagaaa   660
gttgagccca aatcttgtga caaaactcac acatgcccac cgtgcccagc acctgaagcc   720
gcgggggggac cgtcagtctt cctcttcccc ccaaaaccca aggacaccct catgatctcc   780
cggacccctg aggtcacatg cgtggtggtg gacgtgagcc acgaagaccc tgaggtcaag   840
ttcaactggt acgtggacgg cgtggaggtg cataatgcca agacaaagcc gcgggaggag   900
cagtacaaca gcacgtaccg tgtggtcagc gtcctcaccg tcctgcacca ggactggctg   960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgcgaggaga tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtga tgcatgaggc tctgcacaac  1320
cactacacgc agaagagcct ctccctgtct ccgggtaaa                         1359

SEQ ID NO: 81           moltype = DNA   length = 369
FEATURE                 Location/Qualifiers
source                  1..369
                        mol_type = other DNA
                        organism = synthetic construct
SEQUENCE: 81
gaggtgcagc tggtggagtc tggtggaggc gtggtccagc ctgggcgctc cctgagactc    60
tcctgtgcag cctctggatt caccttcagt agctatgcca tgcactgggt ccgccaggct   120
ccaggcaagg gtctggagtg ggtggcagtg atatcctacg atggaagcat caagtactat   180
gcagacgccg tgaagggccg attcaccatc tccagagaca attccaagaa cacgctgtat   240
ctgcaaatga acagcctgag agctgaggac acggccgtgt attactgtgc agagacacaac  300
cgcatctact cctggggctg gcacaccttt gacatctggg gccaaggaac cctggtcacc   360
gtctcctca                                                          369

SEQ ID NO: 82           moltype = DNA   length = 642
FEATURE                 Location/Qualifiers
source                  1..642
                        mol_type = other DNA
                        organism = synthetic construct
SEQUENCE: 82
gacatccaga tgacccagtc tccatcctcc ctgtctgcat ctgtaggaga cagagtcacc    60
atcacttgcc gggcaagtca ggacattagc atatatttaa actggtatca gcagaaacca   120
gggaaagctc ctaagctcct gatctatggc gcatccagct tgcagagtgg tgtcccatca   180
cgcttcagtg gcagtggatc tgggacagat ttcactctca ccatcagcag tctgcaacct   240
gaagattttg caacttacta ctgtcagcag gccgacgcgg ggcctggaca gttcggcgga   300
gggaccaagg tggagatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
```

```
ctgagctcgc ccgtcacaaa gagcttcaac aggggagagt gt                      642
```

SEQ ID NO: 83           moltype = DNA   length = 321
FEATURE                 Location/Qualifiers
source                  1..321
                        mol_type = other DNA
                        organism = synthetic construct SEQUENCE: 83
```
gacatccaga tgacccagtc tccatcctcc ctgtctgcat ctgtaggaga cagagtcacc    60
atcacttgcc gggcaagtca ggacattagc atatatttaa actggtatca gcagaaacca   120
gggaaagctc ctaagctcct gatctatggc gcatccagct tgcagagtgg tgtcccatca   180
cgcttcagtg gcagtggatc tgggacagat ttcactctca ccatcagcag tctgcaacct   240
gaagatttcg caacttacta ctgtcagcag gccgacgcgg ggccttggaa gttcggcgga   300
gggaccaagg tggagatcaa a                                             321
```

SEQ ID NO: 84           moltype = DNA   length = 1290
FEATURE                 Location/Qualifiers
source                  1..1290
                        mol_type = other DNA
                        organism = synthetic construct SEQUENCE: 84
```
gcctctggat tcaccttcag tagctatgcc atgcactggg tccgccaggc tccaggcaag    60
ggtctggagt gggtggcagt gatatcctac gatggaagca tcaagtacta tgcagacgcc   120
gtgaagggcc gattcaccat ctccagagac aattccaaga acacgctgta tctgcaaatg   180
aacagcctga gagctgagga cacggccgtg tattactgtg cgagcacga gcgcatcccc   240
ccctgggggt ttcacacctt tgacatctgg ggccaaggaa ccctggtcac cgtctcctca   300
gcgtcgacca agggcccatc ggtcttcccc ctggcaccct cctccaagag cacctctggg   360
ggcacagcgg ccctgggctg cctggtcaag gactacttcc ccgaaccggt gacggtgtcg   420
tggaactcag gcgccctgac cagcggcgtg cacaccttcc cggctgtcct acagtcctca   480
ggactctact ccctcagcag cgtggtgacc gtgccctcca gcagcttggg cacccagacc   540
tacatctgca acgtgaatca caagcccagc aacaccaagg tggacaagaa agttgagccc   600
aaatcttgtg acaaaactca cacatgccca ccgtgcccag cacctgaagc cgcggggga   660
ccgtcagtct tcctcttccc cccaaaaccc aaggacaccc tcatgatctc ccggacccct   720
gaggtcacat gcgtggtggt ggacgtgagc cacgaagacc ctgaggtcaa gttcaactgg   780
tacgtggacg gcgtggaggt gcataatgcc aagacaaagc cgcgggagga gcagtacaac   840
agcacgtacc gtgtggtcag cgtcctcacc gtcctgcacc aggactggct gaatggcaag   900
gagtacaagt gcaaggtctc caacaaagcc ctcccagccc ccatcgagaa aaccatctcc   960
aaagccaaag gcagccccg agaaccacag gtgtacaccc tgcccccatc ccgcgaggag  1020
atgaccaaga accaggtcag cctgacctgc ctggtcaaag gcttctatcc cagcgacatc  1080
gccgtggagt gggagagcaa tgggcagccg gagaacaact acaagaccac gcctcccgtg  1140
ctggactccg acggctcctt cttcctctac agcaagctca ccgtggacaa gagcaggtgg  1200
cagcagggga acgtcttctc atgctccgtg atgcatgagg ctctgcacaa ccactacacg  1260
cagaagagcc tctccctgtc tccgggtaaa                                  1290
```

SEQ ID NO: 85           moltype = DNA   length = 300
FEATURE                 Location/Qualifiers
source                  1..300
                        mol_type = other DNA
                        organism = synthetic construct SEQUENCE: 85
```
gcctctggat tcaccttcag tagctatgcc atgcactggg tccgccaggc tccaggcaag    60
ggtctggagt gggtggcagt gatatcctac gatggaagca tcaagtacta tgcagacgcc   120
gtgaagggcc gattcaccat ctccagagac aattccaaga acacgctgta tctgcaaatg   180
aacagcctga gagctgagga cacggccgtg tattactgtg cgagcacga gcgcatcccc   240
ccctgggggt tcacaccttt gacatctgg ggccaaggaa ccctggtcac cgtctcctca   300
```

SEQ ID NO: 86           moltype = DNA   length = 642
FEATURE                 Location/Qualifiers
source                  1..642
                        mol_type = other DNA
                        organism = synthetic construct SEQUENCE: 86
```
gacatccaga tgacccagtc tccatcctcc ctgtctgcat ctgtaggaga cagagtcacc    60
atcacttgcc gggcaagtca gggcattagc atttatttaa actggtatca gcagaaacca   120
gggaaagctc ctaagctcct gatctatggc gcatccagct tgcagagtgg tgtcccatca   180
cgcttcagtg gcagtggatc tgggacagat ttcactctca ccatcagcag tctgcaacct   240
gaagatttcg caacttacta ctgtcaacag agtgacggca ccccttggac tttcggcgga   300
gggaccaagg tggagatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

SEQ ID NO: 87           moltype = DNA   length = 321
FEATURE                 Location/Qualifiers
source                  1..321
                        mol_type = other DNA
                        organism = synthetic construct

```
SEQUENCE: 87
gacatccaga tgacccagtc tccatcctcc ctgtctgcat ctgtaggaga cagagtcacc    60
atcacttgcc gggcaagtca gggcattagc atttatttaa actggtatca gcagaaacca   120
gggaaagctc ctaagctcct gatctatggc gcatccagct tgcagagtgg tgtcccatca   180
cgcttcagtg gcagtggatc tgggacagat ttcactctca ccatcagcag tctgcaacct   240
gaagatttcg caacttacta ctgtcaacag agtgacggca cccccttggac tttcggcgga   300
gggaccaagg tggagatcaa a                                              321

SEQ ID NO: 88           moltype = DNA   length = 1341
FEATURE                 Location/Qualifiers
source                  1..1341
                        mol_type = other DNA
                        organism = synthetic construct
SEQUENCE: 88
gaggtgcagc tggtggagtc tggtggaggc gtggtccagc ctgggcgctc cctgagactc    60
tcctgtgcag cctctggatt caccttcagt agctatggga tgcactgggt ccgccaggct   120
ccaggcaagg gtctggagtg ggtggcagtc atatcctacg atggacgcaa caagtactat   180
gcagacgccg tgaagggccg attcaccatc tccagagaca attccaagaa cacgctgtat   240
ctgcaaatga acagcctgag agctgaggac acggccgtgt attactgtgc gagatacaag   300
cccatgccct ttgacgtctg gggccaagga accctggtca ccgtctcctc agcgtcgacc   360
aagggcccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600
aacgtgaatc acaagcccag caacaccaag gtggacaaga agttgagcc caaatcttgt   660
gacaaaactc acacatgccc accgtgccca gcacctgaac cgcgggggg accgtcagtc   720
ttcctcttcc ccccaaaacc caaggacacc ctcatgatct cccggacccc tgaggtcaca   780
tgcgtggtgg tggacgtgag ccacgaagac cctgaggtca agttcaactg gtacgtggac   840
ggcgtggagg tgcataatgc caagacaaag ccgcgggagg agcagtacaa cagcacgtac   900
cgtgtggtca gcgtcctcac cgtcctgcac caggactggc tgaatggcaa ggagtacaag   960
tgcaaggtct ccaacaaagc cctcccagcc cccatcgaga aaccatctc caaagccaaa   1020
gggcagcccc gagaaccaca ggtgtacacc ctgcccccat cccgcgagga tgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa a                                             1341

SEQ ID NO: 89           moltype = DNA   length = 351
FEATURE                 Location/Qualifiers
source                  1..351
                        mol_type = other DNA
                        organism = synthetic construct
SEQUENCE: 89
gaggtgcagc tggtggagtc tggtggaggc gtggtccagc ctgggcgctc cctgagactc    60
tcctgtgcag cctctggatt caccttcagt agctatggga tgcactgggt ccgccaggct   120
ccaggcaagg gtctggagtg ggtggcagtc atatcctacg atggacgcaa caagtactat   180
gcagacgccg tgaagggccg attcaccatc tccagagaca attccaagaa cacgctgtat   240
ctgcaaatga acagcctgag agctgaggac acggccgtgt attactgtgc gagatacaag   300
cccatgccct ttgacgtctg gggccaagga accctggtca ccgtctcctc a             351

SEQ ID NO: 90           moltype = DNA   length = 642
FEATURE                 Location/Qualifiers
source                  1..642
                        mol_type = other DNA
                        organism = synthetic construct
SEQUENCE: 90
gacatccaga tgacccagtc tccatcctcc ctgtctgcat ctgtaggaga cagagtcacc    60
atcacttgcc gggcaagtca gagcattagc agctatttaa actggtatca gcagaaacca   120
gggaaagctc ctaagctcct gatctatgag gcatccatat tgcagagtgg tgtcccatca   180
cgcttcagtg gcagtggatc tgggacagat ttcactctca ccatcagcag tctgcaacct   240
gaagatttcg caacttacta ctgtgggcag agctactaca ccccttttcc cgttcggcga   300
gggaccaagg tggagatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642

SEQ ID NO: 91           moltype = DNA   length = 321
FEATURE                 Location/Qualifiers
source                  1..321
                        mol_type = other DNA
                        organism = synthetic construct
SEQUENCE: 91
gacatccaga tgacccagtc tccatcctcc ctgtctgcat ctgtaggaga cagagtcacc    60
atcacttgcc gggcaagtca gagcattagc agctatttaa actggtatca gcagaaacca   120
gggaaagctc ctaagctcct gatctatgag gcatccatat tgcagagtgg tgtcccatca   180
cgcttcagtg gcagtggatc tgggacagat ttcactctca ccatcagcag tctgcaacct   240
```

```
gaagatttcg caacttacta ctgtgggcag agctactaca cccctttccc gttcggcgga    300
gggaccaagg tggagatcaa a                                              321

SEQ ID NO: 92           moltype = DNA  length = 1341
FEATURE                 Location/Qualifiers
source                  1..1341
                        mol_type = other DNA
                        organism = synthetic construct
SEQUENCE: 92
gaggtgcagc tggtggagtc tggtggaggc gtggtccagc ctgggcgctc cctgagactc    60
tcctgtgcag cctctggatt cgcgttcagc acctatggga tgcactgggt ccgccaggct    120
ccaggcaagg gtctggagtg ggtggcagtg ataaggtacg acggacagga agtactatat    180
gcagacgccg tgaagggccg attcaccatc tccagagaca attccaagaa cacgctgtat    240
ctgcaaatga acagcctgag agctgaggac acggccgtgt attactgtgc agatacaag    300
cccatgccct tgacgtctg gggccaagga accctggtca ccgtctcctc agcgtcgacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660
gacaaaactc acacatgccc accgtgccca gcacctgaag ccgcggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc ccatcgaga aaaccatctc caaagccaaa    1020
gggcagcccc gagaaccaca ggtgtacacc ctgcccccat cccgcgagga tgatgaccaag   1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg    1260
aacgtcttct catgctccgt gatgcatgag gctctgcaca accactacac gcagaagagc    1320
ctctccctgt ctccgggtaa a                                             1341

SEQ ID NO: 93           moltype = DNA  length = 351
FEATURE                 Location/Qualifiers
source                  1..351
                        mol_type = other DNA
                        organism = synthetic construct
SEQUENCE: 93
gaggtgcagc tggtggagtc tggtggaggc gtggtccagc ctgggcgctc cctgagactc    60
tcctgtgcag cctctggatt cgcgttcagc acctatggga tgcactgggt ccgccaggct    120
ccaggcaagg gtctggagtg ggtggcagtg ataaggtacg acggacagga agtactatat    180
gcagacgccg tgaagggccg attcaccatc tccagagaca attccaagaa cacgctgtat    240
ctgcaaatga acagcctgag agctgaggac acggccgtgt attactgtgc agatacaag    300
cccatgccct tgacgtctg gggccaagga accctggtca ccgtctcctc a              351

SEQ ID NO: 94           moltype = DNA  length = 642
FEATURE                 Location/Qualifiers
source                  1..642
                        mol_type = other DNA
                        organism = synthetic construct
SEQUENCE: 94
gacatccaga tgacccagtc tccatcctcc ctgtctgcat ctgtaggaga cagagtcacc    60
atcacttgcc gggcaagtca gagcattagc aggtatttaa actggtatca gcagaaacca    120
gggaaagctc ctaagctcct gatctatgcg gcatccatct gcagagtgg tgtcccatca    180
cgcttcagtg gcagtggatc tgggacagat ttcactctca ccatcagcag tctgcaacct    240
gaagatttcg caacttacta ctgtcaacag agtcacccca cgcctttcac tttcggcgga    300
gggaccaagg tggagatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540
ctgagcaaag cagactacga gaaacacaaa gtctacgcct gcgaagtcac ccatcagggc    600
ctgagctcgc ccgtcacaaa gagcttcaac aggggagagt gt                       642

SEQ ID NO: 95           moltype = DNA  length = 321
FEATURE                 Location/Qualifiers
source                  1..321
                        mol_type = other DNA
                        organism = synthetic construct
SEQUENCE: 95
gacatccaga tgacccagtc tccatcctcc ctgtctgcat ctgtaggaga cagagtcacc    60
atcacttgcc gggcaagtca gagcattagc aggtatttaa actggtatca gcagaaacca    120
gggaaagctc ctaagctcct gatctatgcg gcatccatct gcagagtgg tgtcccatca    180
cgcttcagtg gcagtggatc tgggacagat ttcactctca ccatcagcag tctgcaacct    240
gaagatttcg caacttacta ctgtcaacag agtcacccca cgcctttcac tttcggcgga    300
gggaccaagg tggagatcaa a                                              321

SEQ ID NO: 96           moltype = DNA  length = 1341
FEATURE                 Location/Qualifiers
```

```
source                  1..1341
                        mol_type = other DNA
                        organism = synthetic construct
SEQUENCE: 96
gaggtgcagc tggtggagtc tggtggaggc gtggtccagc ctgggcgctc cctgagactc      60
tcctgtgcag cctctggatt caccttcagt agctatggga tgcactgggt ccgccaggct     120
ccaggcaagg gtctggagtg ggtggcagtc atatactacg atggacgccg caagtactat     180
gcagactccg tgaagggccg attcaccatc tccagagaca attccaagaa cacgctgtat     240
ctgcaaatga acagcctgag agctgaggac acggctgtgt attactgtgc gagagccgac     300
atgcaccgct ttgacgtctg gggccaagga accctggtca ccgtctcctc agcgtcgacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagccc aaatcttgt      660
gacaaaactc acacatgccc accgtgccca gcacctgaac tcgcgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaaa ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc ccatcgaga aaaccatctc caaagccaaa     1020
gggcagcccc gagaaccaca ggtgtacacc ctgcccccat cccgcgagga tgaccaagg     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtaa a                                               1341

SEQ ID NO: 97           moltype = DNA   length = 351
FEATURE                 Location/Qualifiers
source                  1..351
                        mol_type = other DNA
                        organism = synthetic construct
SEQUENCE: 97
gaggtgcagc tggtggagtc tggtggaggc gtggtccagc ctgggcgctc cctgagactc      60
tcctgtgcag cctctggatt caccttcagt agctatggga tgcactgggt ccgccaggct     120
ccaggcaagg gtctggagtg ggtggcagtc atatactacg atggacgccg caagtactat     180
gcagactccg tgaagggccg attcaccatc tccagagaca attccaagaa cacgctgtat     240
ctgcaaatga acagcctgag agctgaggac acggctgtgt attactgtgc gagagccgac     300
atgcaccgct ttgacgtctg gggccaagga accctggtca ccgtctcctc a              351

SEQ ID NO: 98           moltype = DNA   length = 642
FEATURE                 Location/Qualifiers
source                  1..642
                        mol_type = other DNA
                        organism = synthetic construct
SEQUENCE: 98
gacatccaga tgacccagtc tccatcctcc ctgtctgcat ctgtaggaga cagagtcacc      60
atcacttgcc gggcaagtca ggacattatc agctatttaa actggtatca gcagaaacca     120
gggaaagctc ctaagctcct gatctatgtg gcatccagct tgcagagtgg tgtcccatca     180
cgcttcagtg gcagtggatc tgggacagat ttcactctca ccatcagcag tctgcaacct     240
gaagatttcg caactactac tgtcaacag agttacagcc cgccttacac tttcggcgga     300
gggaccaagg tggagatcaa acgtacgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642

SEQ ID NO: 99           moltype = DNA   length = 321
FEATURE                 Location/Qualifiers
source                  1..321
                        mol_type = other DNA
                        organism = synthetic construct
SEQUENCE: 99
gacatccaga tgacccagtc tccatcctcc ctgtctgcat ctgtaggaga cagagtcacc      60
atcacttgcc gggcaagtca ggacattatc agctatttaa actggtatca gcagaaacca     120
gggaaagctc ctaagctcct gatctatgtg gcatccagct tgcagagtgg tgtcccatca     180
cgcttcagtg gcagtggatc tgggacagat ttcactctca ccatcagcag tctgcaacct     240
gaagatttcg caactactac tgtcaacag agttacagcc cgccttacac tttcggcgga     300
gggaccaagg tggagatcaa a                                                321

SEQ ID NO: 100          moltype = DNA   length = 1344
FEATURE                 Location/Qualifiers
source                  1..1344
                        mol_type = other DNA
                        organism = synthetic construct
SEQUENCE: 100
gaggtgcagc tgttggagtc tggtggaggc ttggtacagc ctggtggatc cctgagactc      60
```

```
tcctgtgcag cctctggatt cacctttagc agctacgcga tgagctgggt ccgccaggct    120
ccagggaagg gtctggagtg ggtctcagcc atcagtatga ccgtgggtcg cacatactac    180
gcagactccg tgaagggccg gttcaccatc tccagagaca attccaagaa cacgctgtat    240
ctgcaaatga cagcctgag agccgaggac acggccgtgt attactgtgc gagagtgtgg    300
ggcggcgtgc gctttgacgt ctggggccaa ggaaccctgg tcaccgtctc ctcagcgtcg    360
accaagggcc catcggtctt cccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct tgggcaccca gacctacatc    600
tgcaacgtga atcacaagcc cagcaacacc aaggtggaca gaaagttga cccaaatct     660
tgtgacaaaa ctcacacatg cccaccgtgc ccagcacctg aagccgcggg ggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc ccgagaacc acaggtgtac accctgcccc catcccgcga ggagatgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344

SEQ ID NO: 101         moltype = DNA  length = 354
FEATURE                Location/Qualifiers
source                 1..354
                       mol_type = other DNA
                       organism = synthetic construct
SEQUENCE: 101
gaggtgcagc tgttggagtc tggtggaggc ttggtacagc ctggtggatc cctgagactc     60
tcctgtgcag cctctggatt cacctttagc agctacgcga tgagctgggt ccgccaggct    120
ccagggaagg gtctggagtg ggtctcagcc atcagtatga ccgtgggtcg cacatactac    180
gcagactccg tgaagggccg gttcaccatc tccagagaca attccaagaa cacgctgtat    240
ctgcaaatga cagcctgag agccgaggac acggccgtgt attactgtgc gagagtgtgg    300
ggcggcgtgc gctttgacgt ctggggccaa ggaaccctgg tcaccgtctc ctca         354

SEQ ID NO: 102         moltype = DNA  length = 642
FEATURE                Location/Qualifiers
source                 1..642
                       mol_type = other DNA
                       organism = synthetic construct
SEQUENCE: 102
gacatccaga tgacccagtc tccatcctcc ctgtctgcat ctgtaggaga cagagtcacc     60
atcacttgcc gggcaagtca gagcattagc acctatttaa actggtatca gcagaaacca    120
gggaaagctc ctaagctcct gatctatgtg gcatccatct tgcagagtgg tgtcccatca    180
cgcttcagtg gcagtggatc tgggacagat ttcactctca ccatcagcag tctgcaacct    240
gaagatttcg caacttacta ctgtcaacag agttccagca cgccttggac tttcggcgga    300
gggaccaagg tggagatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642

SEQ ID NO: 103         moltype = DNA  length = 321
FEATURE                Location/Qualifiers
source                 1..321
                       mol_type = other DNA
                       organism = synthetic construct
SEQUENCE: 103
gacatccaga tgacccagtc tccatcctcc ctgtctgcat ctgtaggaga cagagtcacc     60
atcacttgcc gggcaagtca gagcattagc acctatttaa actggtatca gcagaaacca    120
gggaaagctc ctaagctcct gatctatgtg gcatccatct tgcagagtgg tgtcccatca    180
cgcttcagtg gcagtggatc tgggacagat ttcactctca ccatcagcag tctgcaacct    240
gaagatttcg caacttacta ctgtcaacag agttccagca cgccttggac tttcggcgga    300
gggaccaagg tggagatcaa a                                              321
```

ANTI-PAPP-A ANTIBODIES AND METHODS OF USE THEREOF

CROSS REFERENCE TO RELATED APPLICATIONS

This application claims the benefit of U.S. Provisional Application No. 63/383,875, filed Nov. 15, 2022, which is hereby incorporated in its entirety by reference.

SEQUENCE LISTING

The instant application contains a Sequence Listing which is hereby incorporated by reference in its entirety. Said XML copy, created on Jan. 31, 2024, is named CLS-102US ST26.xml, and is 112,924 bytes in size.

BACKGROUND

Autosomal dominant polycystic kidney disease (ADPKD) is a rare disease with unmet medical need. There are approximately 166,000 patients suffering from ADPKD in the US alone. ADPKD is a major cause of morbidity and accounts for about 5-10% of deaths associated with End-Stage Renal Disease (ESRD). Currently, only one approved therapeutic, Tolvaptan, is available. However, Tolvaptan has significant side effects and is prescribed under an FDA mandated Risk Evaluation and Mitigation Strategy (REMS) to mitigate the risk of serious and potentially fatal liver injury due to administration. Thus, additional therapeutics to treat kidney diseases including ADPKD are needed.

SUMMARY

In some aspects, provided herein are isolated human antibodies that binds to human Pregnancy Associated Plasma Protein A (PAPP-A) (SEQ ID NO: 79), wherein the antibody comprises a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein:
CDR-H1 comprises the sequence SYAMH (SEQ ID NO: 3);
CDR-H2 comprises the sequence VISYDGSIKYYA-DAVKG (SEQ ID NO: 4);
CDR-H3 comprises the sequence HNRIYSWGWHTFDI (SEQ ID NO: 5);
CDR-L1 comprises the sequence RASQDISIYLN (SEQ ID NO: 8);
CDR-L2 comprises the sequence GASSLQS (SEQ ID NO: 9); and
CDR-L3 comprises the sequence QQADAGPWK (SEQ ID NO: 10).

In some embodiments, the VH sequence comprises the VH sequence set forth in SEQ ID NO: 2.
In some embodiments, the VL sequence comprises the VL sequence set forth in SEQ ID NO: 7.
In some embodiments, the VH sequence comprises the VH sequence set forth in SEQ ID NO: 2 and the VL sequence comprises the VL sequence set forth in SEQ ID NO: 7.
In some embodiments, the antibody comprises a heavy chain comprising the sequence set forth in SEQ ID NO: 1.
In some embodiments, the antibody comprises a light chain comprising the sequence set forth in SEQ ID NO: 6.

In some embodiments, the antibody comprises a heavy chain comprising the sequence set forth in SEQ ID NO: 1; and a light chain comprising the sequence set forth in SEQ ID NO: 6.

In another aspect, provided herein are isolated human antibodies that binds to human Pregnancy Associated Plasma Protein A (PAPP-A) (SEQ ID NO: 79), wherein the antibody comprises two variable heavy chain (VH) sequences and two variable light chain (VL) sequences, wherein the VH sequences comprise the VH sequence set forth in SEQ ID NO: 2, and the VL sequences comprise the VL sequence set forth in SEQ ID NO: 7.

In another aspect, provided herein are isolated human antibodies that binds to human Pregnancy Associated Plasma Protein A (PAPP-A) (SEQ ID NO: 79), wherein the antibody comprises a human IgG1 Fc region, two heavy chains comprising the sequence set forth in SEQ ID NO: 1, and two light chains comprising the sequence set forth in SEQ ID NO: 6.

In some aspects, provided herein are isolated antibodies that bind to Pregnancy Associated Plasma Protein A (PAPP-A) (SEQ ID NO: 79).

In some embodiments, the antibody comprises a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein:
CDR-H1 comprises the sequence $X_1YX_2MX_3$ (SEQ ID NO: 73), wherein $X_1$ is S or T; $X_2$ is A or G; and $X_3$ is H or S;
CDR-H2 comprises the sequence $X_1IX_2X_3X_4X_5X_6X_7X_8YYADX_9VKG$ (SEQ ID NO: 74), wherein $X_1$ is V or A; $X_2$ is S, Y, or R; $X_3$ is Y or M; $X_4$ is D or T; $X_5$ is G or V; $X_6$ is S, R, G, or Q; $X_7$ is I, R, N, or E; $X_8$ is K or T; and $X_9$ is A or S;
CDR-H3 comprises the sequence $HX_1RIX_2X_3WGX_4HTFDI$ (SEQ ID NO: 75), wherein $X_1$ is N or E; $X_2$ is Y or P; $X_3$ is S or P; and $X_4$ is W or F; the sequence ADMHRFDV (SEQ ID NO: 45), the sequence VWGGVRFDV (SEQ ID NO: 55), or the sequence YKPMPFDV (SEQ ID NOs: 25 or 35);
CDR-L1 comprises the sequence $RASQX_1IX_2X_3YLN$ (SEQ ID NO: 76), wherein $X_1$ is D or S; $X_2$ is S or I; and $X_3$ is I, S, T, or R;
CDR-L2 comprises the sequence $X_1ASX_2LQS$ (SEQ ID NO: 77), wherein $X_1$ is G, V, E, or A; and $X_2$ is S or I; and
CDR-L3 comprises the sequence $X_1QX_2X_3X_4X_5PX_6X_7$ (SEQ ID NO: 78), wherein $X_1$ is Q or G; $X_2$ is A or S; $X_3$ is D, Y, S, or H; $X_4$ is A, S, G, Y, or P; $X_5$ is G, P, or T; $X_6$ is W, Y, or F; and $X_7$ is K, T or P.

In some embodiments, the VH sequence comprises a sequence selected from the sequences set forth in SEQ ID NOs: 2, 12, 22, 32, 42, or 52.
In some embodiments, the VL sequence comprises a sequence selected from the sequences set forth in SEQ ID NOs: 7, 17, 27, 37, 47, or 57.
In some embodiments, the VH sequence comprises the VH sequence set forth in SEQ ID NOs: 2, 12, 22, 32, 42, or 52 and the VL sequence comprises the VL sequence set forth in SEQ ID NOs: 7, 17, 27, 37, 47, or 57.
In some embodiments, the antibody comprises a heavy chain sequence selected from the sequences set forth in SEQ ID NOs: 1, 11, 21, 31, 41, or 51.

In some embodiments, the antibody comprises a light chain sequence selected from the sequences set forth in SEQ ID NOs: 6, 16, 26, 36, 46, or 56.

In some embodiments, the antibody comprises a heavy chain sequence selected from the sequences set forth in SEQ ID NOs: 1, 11, 21, 31, 41, or 51; and a light chain sequence selected from the sequences set forth in SEQ ID NOs: 6, 16, 26, 36, 46, or 56.

In some embodiments, the antibody comprises two heavy chain sequences comprising a sequence selected from the sequences set forth in SEQ ID NOs: 1, 11, 21, 31, 41, or 51; and two light chain sequences comprising a sequence selected from the sequences set forth in SEQ ID NOs: 6, 16, 26, 36, 46, or 56.

In some embodiments, the CDR-H3 comprises HNRIYSWGWHTFDI (SEQ ID NO: 5) or HERIPPWGFHTFDI (SEQ ID NO: 15).

In some embodiments, the
CDR-H1 comprises the sequence as set forth in SEQ ID NO: 3;
CDR-H2 comprises the sequence as set forth in SEQ ID NO: 4;
CDR-H3 comprises the sequence as set forth in SEQ ID NO: 5;
CDR-L1 comprises the sequence as set forth in SEQ ID NO: 8;
CDR-L2 comprises the sequence as set forth in SEQ ID NO: 9; and
CDR-L3 comprises the sequence as set forth in SEQ ID NO: 10.

In some embodiments, the VH sequence comprises the VH sequence set forth in SEQ ID NO: 2.

In some embodiments, the VL sequence comprises the VL sequence set forth in SEQ ID NO: 7.

In some embodiments, the VH sequence comprises the VH sequence set forth in SEQ ID NO: 2 and the VL sequence comprises the VL sequence set forth in SEQ ID NO: 7.

In some embodiments, the antibody comprises a heavy chain comprising the sequence set forth in SEQ ID NO: 1.

In some embodiments, the antibody comprises a light chain comprising the sequence set forth in SEQ ID NO: 6.

In some embodiments, the antibody comprises a heavy chain comprising the sequence set forth in SEQ ID NO: 1; and a light chain comprising the sequence set forth in SEQ ID NO: 6.

In some embodiments, the
CDR-H1 comprises the sequence as set forth in SEQ ID NO: 13;
CDR-H2 comprises the sequence as set forth in SEQ ID NO: 14;
CDR-H3 comprises the sequence as set forth in SEQ ID NO: 15;
CDR-L1 comprises the sequence as set forth in SEQ ID NO: 18;
CDR-L2 comprises the sequence as set forth in SEQ ID NO: 19; and
CDR-L3 comprises the sequence as set forth in SEQ ID NO: 20.

In some embodiments, the VH sequence comprises the VH sequence set forth in SEQ ID NO: 12.

In some embodiments, the VL sequence comprises the VL sequence set forth in SEQ ID NO: 17.

In some embodiments, the VH sequence comprises the VH sequence set forth in SEQ ID NO: 12 and the VL sequence comprises the VL sequence set forth in SEQ ID NO: 17.

In some embodiments, the antibody comprises a heavy chain comprising the sequence set forth in SEQ ID NO: 11.

In some embodiments, the antibody comprises a light chain comprising the sequence set forth in SEQ ID NO: 16.

In some embodiments, the antibody comprises a heavy chain comprising the sequence set forth in SEQ ID NO: 11; and a light chain comprising the sequence set forth in SEQ ID NO: 16

In some embodiments, the
CDR-H1 comprises the sequence as set forth in SEQ ID NO: 23;
CDR-H2 comprises the sequence as set forth in SEQ ID NO: 24;
CDR-H3 comprises the sequence as set forth in SEQ ID NO: 25;
CDR-L1 comprises the sequence as set forth in SEQ ID NO: 28;
CDR-L2 comprises the sequence as set forth in SEQ ID NO: 29; and
CDR-L3 comprises the sequence as set forth in SEQ ID NO: 30.

In some embodiments, the VH sequence comprises the VH sequence set forth in SEQ ID NO: 22.

In some embodiments, the VL sequence comprises the VL sequence set forth in SEQ ID NO: 27.

In some embodiments, the VH sequence comprises the VH sequence set forth in SEQ ID NO: 22 and the VL sequence comprises the VL sequence set forth in SEQ ID NO: 27.

In some embodiments, the antibody comprises a heavy chain comprising the sequence set forth in SEQ ID NO: 21.

In some embodiments, the antibody comprises a light chain comprising the sequence set forth in SEQ ID NO: 26.

In some embodiments, the antibody comprises a heavy chain comprising the sequence set forth in SEQ ID NO: 21; and a light chain comprising the sequence set forth in SEQ ID NO: 26.

In some embodiments, the
CDR-H1 comprises the sequence as set forth in SEQ ID NO: 33;
CDR-H2 comprises the sequence as set forth in SEQ ID NO: 34;
CDR-H3 comprises the sequence as set forth in SEQ ID NO: 35;
CDR-L1 comprises the sequence as set forth in SEQ ID NO: 38;
CDR-L2 comprises the sequence as set forth in SEQ ID NO: 39; and
CDR-L3 comprises the sequence as set forth in SEQ ID NO: 40.

In some embodiments, the VH sequence comprises the VH sequence set forth in SEQ ID NO: 32.

In some embodiments, the VL sequence comprises the VL sequence set forth in SEQ ID NO: 37.

In some embodiments, the VH sequence comprises the VH sequence set forth in SEQ ID NO: 32 and the VL sequence comprises the VL sequence set forth in SEQ ID NO: 37.

In some embodiments, the antibody comprises a heavy chain comprising the sequence set forth in SEQ ID NO: 31.

In some embodiments, the antibody comprises a light chain comprising the sequence set forth in SEQ ID NO: 36.

In some embodiments, the antibody comprises a heavy chain comprising the sequence set forth in SEQ ID NO: 31; and a light chain comprising the sequence set forth in SEQ ID NO: 36.

In some embodiments, the
CDR-H1 comprises the sequence as set forth in SEQ ID NO: 43;
CDR-H2 comprises the sequence as set forth in SEQ ID NO: 44;
CDR-H3 comprises the sequence as set forth in SEQ ID NO: 45;
CDR-L1 comprises the sequence as set forth in SEQ ID NO: 48;
CDR-L2 comprises the sequence as set forth in SEQ ID NO: 49; and
CDR-L3 comprises the sequence as set forth in SEQ ID NO: 50.

In some embodiments, the VH sequence comprises the VH sequence set forth in SEQ ID NO: 42.

In some embodiments, the VL sequence comprises the VL sequence set forth in SEQ ID NO: 47.

In some embodiments, the VH sequence comprises the VH sequence set forth in SEQ ID NO: 42 and the VL sequence comprises the VL sequence set forth in SEQ ID NO: 47.

In some embodiments, the antibody comprises a heavy chain comprising the sequence set forth in SEQ ID NO: 41.

In some embodiments, the antibody comprises a light chain comprising the sequence set forth in SEQ ID NO: 46.

In some embodiments, the antibody comprises a heavy chain comprising the sequence set forth in SEQ ID NO: 41; and a light chain comprising the sequence set forth in SEQ ID NO: 46.

In some embodiments, the
CDR-H1 comprises the sequence as set forth in SEQ ID NO: 53;
CDR-H2 comprises the sequence as set forth in SEQ ID NO: 54;
CDR-H3 comprises the sequence as set forth in SEQ ID NO: 55;
CDR-L1 comprises the sequence as set forth in SEQ ID NO: 58;
CDR-L2 comprises the sequence as set forth in SEQ ID NO: 59; and
CDR-L3 comprises the sequence as set forth in SEQ ID NO: 60.

In some embodiments, the VH sequence comprises the VH sequence set forth in SEQ ID NO: 52.

In some embodiments, the VL sequence comprises the VL sequence set forth in SEQ ID NO: 57.

In some embodiments, the VH sequence comprises the VH sequence set forth in SEQ ID NO: 52 and the VL sequence comprises the VL sequence set forth in SEQ ID NO: 57.

In some embodiments, the antibody comprises a heavy chain comprising the sequence set forth in SEQ ID NO: 51.

In some embodiments, the antibody comprises a light chain comprising the sequence set forth in SEQ ID NO: 56.

In some embodiments, the antibody comprises a heavy chain comprising the sequence set forth in SEQ ID NO: 51; and a light chain comprising the sequence set forth in SEQ ID NO: 56.

In some embodiments, the antibody comprises a variable heavy chain (VH) sequence comprising three heavy chain CDR sequences, CDR-H1, CDR-H2, and CDR-H3, wherein the CDR-H1, CDR-H2, and CDR-H3 comprises the CDRs of one of the variable heavy (VH) chain sequences set forth in SEQ ID NOs: 2, 12, 22, 32, 42, or 52, as defined by Kabat, AbM, IMGT, or Chothia numbering schemes.

In some embodiments, the antibody comprises a variable light chain (VL) sequence comprising three light chain CDR sequences, CDR-L1, CDR-L2, and CDR-L3, wherein the CDR-L1, CDR-L2, and CDR-L3 comprises the CDRs of one of the variable light (VL) chain sequences set forth in SEQ ID NOs: 7, 17, 27, 37, 47, or 57, as defined by Kabat, AbM, IMGT, or Chothia numbering schemes.

In some embodiments, the antibody comprises a chimeric, human, or humanized antibody.

In some embodiments, the antibody is a monoclonal antibody.

In some embodiments, the antibody is a humanized antibody.

In some embodiments, the antibody is a human antibody.

In some embodiments, the antibody comprises an Fc region.

In some embodiments, the Fc region comprises a human Fc region.

In some embodiments, the human Fc region comprises a human IgG1 Fc region.

In some embodiments, the Fc region comprises an L234A/L235A mutation, according to the EU numbering system.

In another aspect, provided herein is an isolated human antibody that binds to Pregnancy Associated Plasma Protein A (PAPP-A) (SEQ ID NO: 79), wherein the antibody comprises a human IgG1 Fc region, two heavy chains comprising the sequence set forth in SEQ ID NO: 1, and two light chains comprising the sequence set forth in SEQ ID NO: 6.

In another aspect, provided herein is an isolated human antibody that binds to Pregnancy Associated Plasma Protein A (PAPP-A) (SEQ ID NO: 79), wherein the antibody comprises a human IgG1 Fc region, two heavy chains comprising the sequence set forth in SEQ ID NO: 11, and two light chains comprising the sequence set forth in SEQ ID NO: 16.

In another aspect, provided herein is an isolated human antibody that binds to Pregnancy Associated Plasma Protein A (PAPP-A) (SEQ ID NO: 79), wherein the antibody comprises a human IgG1 Fc region, two heavy chains comprising the sequence set forth in SEQ ID NO: 21, and two light chains comprising the sequence set forth in SEQ ID NO: 26.

In another aspect, provided herein is an isolated human antibody that binds to Pregnancy Associated Plasma Protein A (PAPP-A) (SEQ ID NO: 79), wherein the antibody comprises a human IgG1 Fc region, two heavy chains comprising the sequence set forth in SEQ ID NO: 31, and two light chains comprising the sequence set forth in SEQ ID NO: 36.

In another aspect, provided herein is an isolated human antibody that binds to Pregnancy Associated Plasma Protein A (PAPP-A) (SEQ ID NO: 79), wherein the antibody comprises a human IgG1 Fc region, two heavy chains comprising the sequence set forth in SEQ ID NO: 41, and two light chains comprising the sequence set forth in SEQ ID NO: 46.

In another aspect, provided herein is an isolated human antibody that binds to Pregnancy Associated Plasma Protein A (PAPP-A) (SEQ ID NO: 79), wherein the antibody comprises a human IgG1 Fc region, two heavy chains comprising the sequence set forth in SEQ ID NO: 51, and two light chains comprising the sequence set forth in SEQ ID NO: 56.

In some embodiments, the antibody binds to human PAPP-A with a $K_D$ of less than or equal to about 1, 1.5, 2, 2.5, 10, 25, 50, 75, or $100 \times 10^{-12}$ M, as measured by surface plasmon resonance (SPR) assay.

In some embodiments, the antibody has enzyme blocking or neutralizing activity, optionally wherein the antibody has metalloprotease blocking activity.

In some embodiments, the antibody blocks PAPP-A cleavage of IGF-binding proteins.

The isolated antibody as disclosed herein for use as a medicament.

The isolated antibody as disclosed herein for use in the treatment of a PAPP-A associated disorder.

In another aspect, provided herein are isolated polynucleotides or sets of polynucleotides encoding the antibody of any of the above claims, a VH thereof, a VL thereof, a light chain thereof, a heavy chain thereof, or an antigen-binding portion thereof; optionally the isolated polynucleotide or set of polynucleotides is cDNA.

In another aspect, provided herein are vectors or sets of vectors comprising the polynucleotide or set of polynucleotides as disclosed herein.

In another aspect, provided herein are host cells comprising the polynucleotide or set of polynucleotides as disclosed herein or the vector or set of vectors as disclosed herein.

In another aspect, provided herein are methods of producing an antibody comprising expressing the antibody with the host cell as disclosed herein and isolating the expressed antibody.

In another aspect, provided herein are pharmaceutical compositions comprising the isolated antibody as disclosed herein and a pharmaceutically acceptable excipient.

In another aspect, provided herein are kits comprising the isolated antibody as disclosed herein or the pharmaceutical composition as disclosed herein and instructions for use.

In another aspect, provided herein are methods of treating a PAPP-A associated disorder in a subject comprising administering to the subject a composition comprising an anti-PAPP-A antibody.

In some embodiments, the PAPP-A associated disorder is kidney disease, polycystic kidney disease, or autosomal dominant polycystic kidney disease (ADPKD).

BRIEF DESCRIPTION OF THE SEVERAL VIEWS OF THE DRAWINGS

These and other features, aspects, and advantages of the present disclosure will become better understood with regard to the following description, and accompanying drawings, where.

DETAILED DESCRIPTION

Definitions

Figure 1:
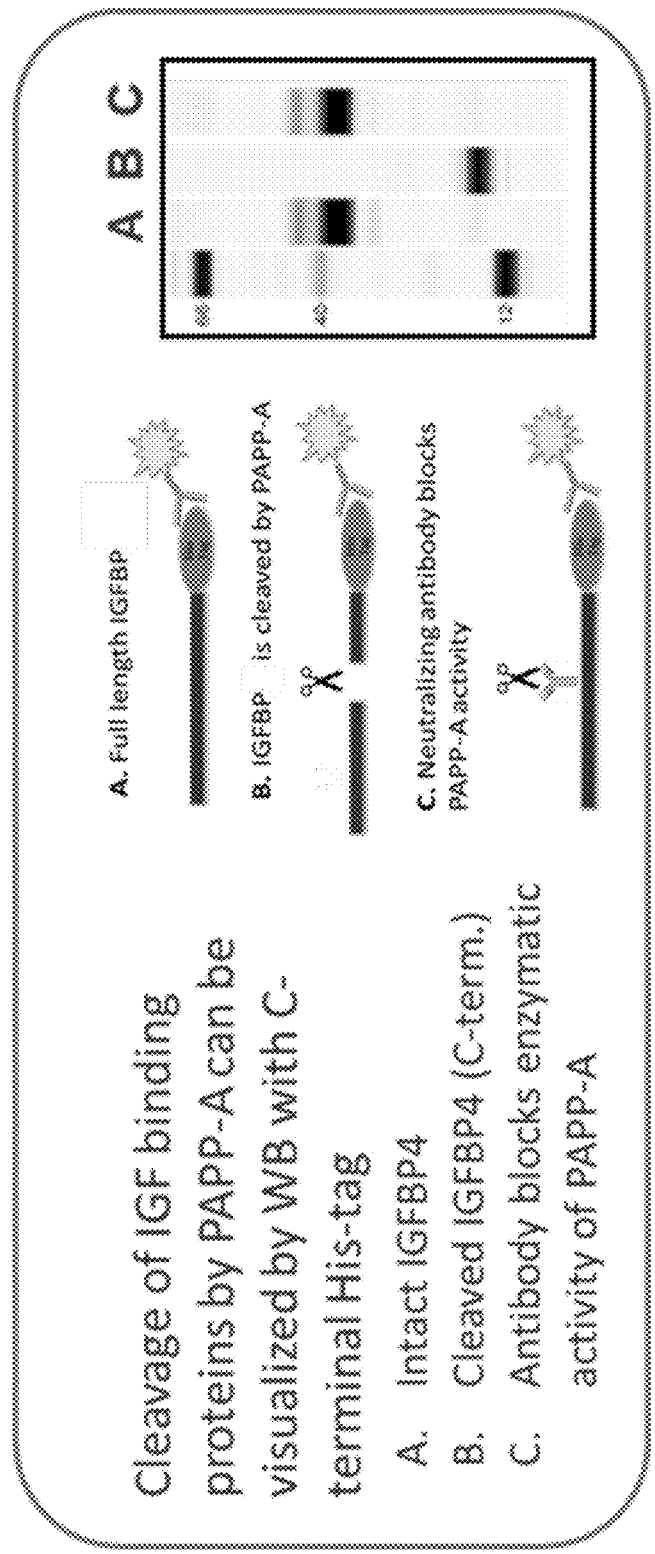
FIG. 1. A graphic depiction of the method used to assess the in vitro analysis of PAPP-A activity as measured by cleavage of IGF binding protein 4 (IGFBP4). The resulting western blot shows the uncut and cleaved IGFBP bands and was quantified using Compass for SW software (Biotechne®).

Terms used in the claims and specification are defined as set forth below unless otherwise specified.

The term "ameliorating" refers to any therapeutically beneficial result in the treatment of a disease state, e.g., a kidney disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (nebi.nlm.nih.gov/).

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise. Thus, for example, reference to "a compound" includes a single compound as well as one or more of the same or different compounds; reference to "a pharmaceutically acceptable carrier" means a single pharmaceutically acceptable carrier as well as one or more pharmaceutically acceptable carriers, and the like.

The term "ADPKD" as used herein, defines autosomal dominant polycystic kidney disease.

The term "APC" as used herein, defines allophycocyanin.

The term "scFv," as used herein, defines a single chain fragment variable, a fusion protein of the variable regions of the heavy (VH) and light chains (VL) of immunoglobulins, connected with a short linker peptide. These chimeric proteins are used in yeast display technology.

The term "Fc region" as used herein, defines a portion of IgG (IgG Fc) that interacts with effector proteins, including Fcγ receptors.

The term "GFR" as used herein, defines glomerular filtration rate.

The term "ICH" as used herein defines the International Conference of Harmonization, specifically the guidelines for photostability.

The term "neutralizing" as used herein, defines the inhibition of an enzymatic target protein by an antibody.

The term "NHP" as used herein, defines a non-human primate, specifically the cynomolgus monkey or macaque.

The term "PAPP-A" as used herein, defines the pregnancy associated plasma protein-A that is produced by the placenta and is necessary for the implantation process and to maintain the placenta during pregnancy.

The term "SPR" as used herein, defines surface plasmon resonance, an optical technique utilized for detecting interactions between two molecules.

The term "t-GFR" as used herein, defines transdermal glomerular filtration rate.

The term "TKV" as used herein, defines total kidney volume.

The term "WB" as used herein, defines western blot.

Antibodies

Structure

The present application provides antibodies and compositions comprising an antibody which binds Pregnancy Associated Plasma Protein A (PAPP-A). Such antibodies including antibodies that block, inhibit, or reduce PAPP-A enzymatic activity.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies.

The recognized immunoglobulin genes include the kappa, lambda, alpha, gamma, delta, epsilon and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

An exemplary immunoglobulin (antibody) structural unit is composed of two pairs of polypeptide chains, each pair having one "light" (about 25 kD) and one "heavy" chain (about 50-70 kD), e.g., a homodimer of a paired light chain and heavy chain. In other words, the exemplary antibody comprises two heavy chains and two light chains. The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises of the VH, CH1, CH2 and CH3 domains respectively from the N to C-terminus. The light chain comprises of the VL and CL domains from N to C terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain found in an antibody provided herein, is from or derived from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

In some embodiments, the antibodies provided herein comprise a heavy chain. In one embodiment, the heavy chain is an IgA. In one embodiment, the heavy chain is an IgD. In one embodiment, the heavy chain is an IgE. In one embodiment, the heavy chain is an IgG. In one embodiment, the heavy chain is an IgM. In one embodiment, the heavy chain is an IgG1. In one embodiment, the heavy chain is an IgG2. In one embodiment, the heavy chain is an IgG3. In one embodiment, the heavy chain is an IgG4. In one embodiment, the heavy chain is an IgA1. In one embodiment, the heavy chain is an IgA2.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen-binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia"

numbering scheme); MacCallum et al., 1996, *J. Mol. Biol.* 262:732-745 ("Contact" numbering scheme); Lefranc et al., *Dev. Comp. Immunol.,* 2003, 27:55-77 ("IMGT" numbering scheme); and Honegger and Pluckthun, *J. Mol. Biol.,* 2001, 309:657-70 ("AHo" numbering scheme); each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at bioinf.org.uk/abs/abnum/, and described in Abhinandan and Martin, *Immunology,* 2008, 45:3832-3839, incorporated by reference in its entirety.

TABLE 1

Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H66 | H52-H56 |
| H3 | H99-H112 | H95-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

As used herein, the term "single-chain" refers to a molecule comprising amino acid monomers linearly linked by peptide bonds. In a particular such embodiment, the C-terminus of the Fab light chain is connected to the N-terminus of the Fab heavy chain in the single-chain Fab molecule. As described in more detail herein, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain.

The "Fab fragment" (also referred to as fragment antigen-binding) contains the constant domain (CL) of the light chain and the first constant domain (CH1) of the heavy chain along with the variable domains VL and VH on the light and heavy chains respectively. The variable domains comprise the complementarily determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with β-mercaptoethanol.

The "Single-chain Fv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in *The Pharmacology of Monoclonal Antibodies,* vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "epitope" means a portion of an antigen that specifically binds to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to PAPP-A variants with different point-mutations, or to chimeric PAPP-A variants.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

"Effector functions" refer to those biological activities mediated by the Fc region of an antibody, which activities may vary depending on the antibody isotype. Examples of antibody effector functions include C1q binding to activate complement dependent cytotoxicity (CDC), Fc receptor binding to activate antibody-dependent cellular cytotoxicity (ADCC), and antibody dependent cellular phagocytosis (ADCP), receptor ligand blocking, agonism, or antagonism. An active Fc region is one that is capable of Fc-based effector functions such as ADCC, CDC, and/or ADCP.

Anti-PAPP-A antibodies can include those described herein such as the clones set forth in the tables. In some embodiments, the antibody comprises an alternative scaffold. In some embodiments, the antibody consists of an alternative scaffold. In some embodiments, the antibody consists essentially of an alternative scaffold. In some embodiments, the antibody comprises an antibody fragment. In some embodiments, the antibody consists of an antibody fragment. In some embodiments, the antibody consists essentially of an antibody fragment. A "PAPP-A antibody," "anti-PAPP-A antibody," or "PAPP-A-specific antibody" is an antibody, as provided herein, which specifically binds to the antigen PAPP-A. In some embodiments, the antibody binds the extracellular domain of PAPP-A. In certain embodiments, a PAPP-A antibody provided herein binds to an epitope of PAPP-A that is conserved between or among PAPP-A proteins from different species.

The term "chimeric antibody" or "chimera antibody" refers to an antibody in which a portion of the heavy and/or light chain is derived from a particular source or species, while the remainder of the heavy and/or light chain is derived from a different source or species.

In some embodiments, the antibody comprises a mouse PAPP-A antibody. In some embodiments, the antibody comprises a chimeric PAPP-A antibody. In some embodiments, the antibody comprises a humanized PAPP-A antibody. In some embodiments, the antibody comprises a human PAPP-A antibody.

In one embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies. In one embodiment, all of the variable and constant domains are derived from human immunoglobulin sequences (a fully human antibody). These antibodies may be prepared in a variety of ways including through the immunization with an antigen of interest of a mouse that is genetically modified to express antibodies derived from human heavy and/or light chain-encoding genes.

In some embodiments, the antibodies provided herein comprise an antibody fragment. In some embodiments, the antibodies provided herein consist of an antibody fragment. In some embodiments, the antibodies provided herein consist essentially of an antibody fragment. In some embodiments, the antibody fragment is an Fv fragment. In some embodiments, the antibody fragment is a Fab fragment. In some embodiments, the antibody fragment is a F(ab')$_2$ fragment. In some embodiments, the antibody fragment is a Fab' fragment. In some embodiments, the antibody fragment is an scFv (sFv) fragment. In some embodiments, the antibody fragment is an scFv-Fc fragment. In some embodiments, the antibody fragment is a fragment of a single domain antibody.

In some aspects, provided herein are isolated polynucleotides or sets of polynucleotides encoding the antibody of any of the above claims, a VH thereof, a VL thereof, a light chain thereof, a heavy chain thereof, or an antigen-binding portion thereof; optionally the isolated polynucleotide or set of polynucleotides is cDNA. Nucleotide sequences of the VH, VL, heavy and light chain sequences of the PAPP-A antibodies are provided in SEQ ID NOs: 80-103. For example, heavy chain sequences of the PAPP-A antibodies disclosed herein are provided as the sequences set forth as SEQ ID NOs: 80, 84, 88, 92, 96, and 100. Variable heavy chain sequences of the PAPP-A antibodies disclosed herein are provided as the sequences set forth as SEQ ID NOs: 81, 85, 89, 93, 97, and 101. Light chain sequences of the PAPP-A antibodies disclosed herein are provided as the sequences set forth as SEQ ID NOs: 82, 86, 90, 94, 98, and 102. Variable light chain sequences of the PAPP-A antibodies disclosed herein are provided as the sequences set forth as SEQ ID NOs: 83, 87, 91, 95, 99 and 103.

In some embodiments, a PAPP-A antibody comprises a variable heavy (VH) chain nucleotide sequence comprising the sequence set forth in any one of SEQ ID NOs: 81, 85, 89, 93, 97, and 101. In some embodiments, a PAPP-A antibody comprises a variable light (VL) chain nucleotide sequence comprising the sequence set forth in any one of SEQ ID NOs: 83, 87, 91, 95, 99 and 103. In some embodiments, a PAPP-A antibody comprises a heavy chain nucleotide sequence comprising the sequence set forth in any one of SEQ ID NOs: 80, 84, 88, 92, 96, and 100. In some embodiments, a PAPP-A antibody comprises a light VL chain nucleotide sequence comprising the sequence set forth in any one of SEQ ID NOs: 82, 86, 90, 94, 98, and 102.

CDRs

In some embodiments, an isolated antibody that binds to human PAPP-A (SEQ ID NO: 79), comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein: CDR-H1 comprises the sequence $X_1YX_2MX_3$ (SEQ ID NO: 73), wherein $X_1$ is S or T; $X_2$ is G or A; and $X_3$ is S or H; CDR-H2 comprises the sequence $X_1IX_2X_3X_4X_5X_6X_7X_8YYADX_9VKG$ (SEQ ID NO: 74), wherein $X_1$ is V or A; $X_2$ is Y, S, or R; $X_3$ is Y or M; $X_4$ is D or T; $X_5$ is G or V; $X_6$ is R, G, S, or Q; $X_7$ is R, I, N, or E; $X_8$ is K or T; and $X_9$ is S or A; CDR-H3 comprises the sequence $HX_1RIX_2X_3WGX_4HTFDI$ (SEQ ID NO: 75), wherein $X_1$ is E or N; $X_2$ is P or Y; $X_3$ is P or S; and $X_4$ is F or W; the sequence ADMHRFDV (SEQ ID NO: 45), the sequence VWGGVRFDV (SEQ ID NO: 55), or the sequence YKPMPFDV (SEQ ID NO: 25 or SEQ ID NO: 35); CDR-L1 comprises the sequence $RASQX_1IX_2X_3YLN$ (SEQ ID NO: 76), wherein $X_1$ is D or S; $X_2$ is I or S; and $X_3$ is S, T, I, or R; CDR-L2 comprises the sequence $X_1ASX_2LQS$ (SEQ ID NO: 77), wherein $X_1$ is V, G, E, or A; and $X_2$ is S or I; and CDR-L3 comprises the sequence $X_1QX_2X_3X_4X_5PX_6X_7$ (SEQ ID NO: 78), wherein $X_1$ is Q or G; $X_2$ is S or A; $X_3$ is Y, S, D, or H; $X_4$ is S, G, A, Y, or P; $X_5$ is P, T, or G; $X_6$ is Y, W, or F; and $X_7$ is K, T, or P.

In some embodiments, CDR-H3 comprises the sequence HNRIYSWGWHTFDI (SEQ ID NO: 5). In some embodiments, CDR-H3 comprises the sequence HERIPPWGFHTFDI (SEQ ID NO: 15). In some embodiments, CDR-H3 comprises the sequence YKPMPFDV (SEQ ID NO: 25 or 35). In some embodiments, CDR-H3 comprises the sequence ADMHRFDV (SEQ ID NO: 45) In some embodiments, CDR-H3 comprises the sequence the sequence VWGGVRFDV (SEQ ID NO: 55).

In some embodiments, an antibody provided herein comprises a CDR-H3 of SEQ ID NO: 5, a CDR-H2 of SEQ ID NO: 4, a CDR-H1 of SEQ ID NO: 3, a CDR-L3 of SEQ ID NO: 10, a CDR-L2 of SEQ ID NO: 9, and a CDR-L1 of SEQ ID NO: 8. In some embodiments, the CDR-H3 has at least about 50%, 75%, 80%, 85%, 90%, or 95% identity with a CDR-H3 of SEQ ID NO: 5, the CDR-H2 has at least about 50%, 75%, 80%, 85%, 90%, or 95% identity with a CDR-H2 of SEQ ID NO: 4, the CDR-H1 has at least about 50%, 75%, 80%, 85%, 90%, or 95% identity with a CDR-H1 of SEQ ID NO: 3, the CDR-L3 has at least about 50%, 75%, 80%, 85%, 90%, or 95% identity with a CDR-L3 of SEQ ID NO: 10, the CDR-L2 has at least about 50%, 75%, 80%, 85%, 90%, or 95% identity with a CDR-L2 of SEQ ID NO: 9, and the CDR-L1 has at least about 50%, 75%, 80%, 85%, 90%, or 95% identity with a CDR-L1 of SEQ ID NO: 8. In some embodiments, the CDR-H3 is a CDR-H3 of SEQ ID NO: 5, with up to 1, 2, 3, 4, 5, 6, 7, or 8 amino acid substitutions; the CDR-H2 is a CDR-H2 of SEQ ID NO: 4, with up to 1, 2, 3, 4, 5, 6, 7, or 8 amino acid substitutions; the CDR-H1 is a CDR-H1 of SEQ ID NO: 3, with up to 1, 2, 3, 4, or 5 amino acid substitutions; the CDR-L3 is a CDR-L3 of SEQ ID NO: 10, with up to 1, 2, 3, 4, or 5 amino acid substitutions; the CDR-L2 is a CDR-L2 of SEQ ID NO: 9, with up to 1, 2, 3, or 4 amino acid substitutions; and the CDR-L1 is a CDR-L1 of SEQ ID NO: 8 with up to 1, 2, 3, 4, 5, or 6 amino acid substitutions.

In some embodiments, an antibody provided herein comprises a CDR-H3 of SEQ ID NO: 15, a CDR-H2 of SEQ ID NO: 14, a CDR-H1 of SEQ ID NO: 13, a CDR-L3 of SEQ ID NO: 20, a CDR-L2 of SEQ ID NO: 19, and a CDR-L1 of SEQ ID NO: 18. In some embodiments, the CDR-H3 has at least about 50%, 75%, 80%, 85%, 90%, or 95% identity with a CDR-H3 of SEQ ID NO: 15, the CDR-H2 has at least about 50%, 75%, 80%, 85%, 90%, or 95% identity with a CDR-H2 of SEQ ID NO: 14, the CDR-H1 has at least about 50%, 75%, 80%, 85%, 90%, or 95% identity with a CDR-H1 of SEQ ID NO: 13, the CDR-L3 has at least about 50%, 75%, 80%, 85%, 90%, or 95% identity with a CDR-L3 of SEQ ID NO: 20, the CDR-L2 has at least about 50%, 75%, 80%, 85%, 90%, or 95% identity with a CDR-L2 of SEQ ID NO: 19, and the CDR-L1 has at least about 50%, 75%, 80%, 85%, 90%, or 95% identity with a CDR-L1 of SEQ ID NO: 18. In some embodiments, the CDR-H3 is a CDR-H3 of SEQ ID NO: 15, with up to 1, 2, 3, 4, 5, 6, 7, or 8 amino acid substitutions; the CDR-H2 is a CDR-H2 of SEQ ID NO: 14, with up to 1, 2, 3, 4, 5, 6, 7, or 8 amino acid substitutions; the CDR-H1 is a CDR-H1 of SEQ ID NO: 13, with up to 1, 2, 3, 4, or 5 amino acid substitutions; the CDR-L3 is a CDR-L3 of SEQ ID NO: 20, with up to 1, 2, 3, 4, or 5 amino acid substitutions; the CDR-L2 is a CDR-L2 of SEQ ID NO: 19, with up to 1, 2, 3, or 4 amino acid substitutions; and the CDR-L1 is a CDR-L1 of SEQ ID NO: 18 with up to 1, 2, 3, 4, 5, or 6 amino acid substitutions.

In some embodiments, an antibody provided herein comprises a CDR-H3 of SEQ ID NO: 25, a CDR-H2 of SEQ ID NO: 24, a CDR-H1 of SEQ ID NO: 23, a CDR-L3 of SEQ ID NO: 30, a CDR-L2 of SEQ ID NO: 29, and a CDR-L1 of SEQ ID NO: 28. In some embodiments, the CDR-H3 has at least about 50%, 75%, 80%, 85%, 90%, or 95% identity with a CDR-H3 of SEQ ID NO: 25, the CDR-H2 has at least about 50%, 75%, 80%, 85%, 90%, or 95% identity with a CDR-H2 of SEQ ID NO: 24, the CDR-H1 has at least about 50%, 75%, 80%, 85%, 90%, or 95% identity with a CDR-H1 of SEQ ID NO: 23, the CDR-L3 has at least about 50%, 75%, 80%, 85%, 90%, or 95% identity with a CDR-L3 of SEQ ID NO: 30, the CDR-L2 has at least about 50%, 75%, 80%, 85%, 90%, or 95% identity with a CDR-L2 of SEQ ID NO: 29, and the CDR-L1 has at least about 50%, 75%, 80%, 85%, 90%, or 95% identity with a CDR-L1 of SEQ ID NO: 28. In some embodiments, the CDR-H3 is a CDR-H3 of SEQ ID NO: 25, with up to 1, 2, 3, 4, 5, 6, 7, or 8 amino acid substitutions; the CDR-H2 is a CDR-H2 of SEQ ID NO: 24, with up to 1, 2, 3, 4, 5, 6, 7, or 8 amino acid substitutions; the CDR-H1 is a CDR-H1 of SEQ ID NO: 23, with up to 1, 2, 3, 4, or 5 amino acid substitutions; the CDR-L3 is a CDR-L3 of SEQ ID NO: 30, with up to 1, 2, 3, 4, or 5 amino acid substitutions; the CDR-L2 is a CDR-L2 of SEQ ID NO: 29, with up to 1, 2, 3, or 4 amino acid substitutions; and the CDR-L1 is a CDR-L1 of SEQ ID NO: 28 with up to 1, 2, 3, 4, 5, or 6 amino acid substitutions.

In some embodiments, an antibody provided herein comprises a CDR-H3 of SEQ ID NO: 35, a CDR-H2 of SEQ ID NO: 34, a CDR-H1 of SEQ ID NO: 33, a CDR-L3 of SEQ ID NO: 40, a CDR-L2 of SEQ ID NO: 39, and a CDR-L1 of SEQ ID NO: 38. In some embodiments, the CDR-H3 has at least about 50%, 75%, 80%, 85%, 90%, or 95% identity with a CDR-H3 of SEQ ID NO: 35, the CDR-H2 has at least about 50%, 75%, 80%, 85%, 90%, or 95% identity with a CDR-H2 of SEQ ID NO: 34, the CDR-H1 has at least about 50%, 75%, 80%, 85%, 90%, or 95% identity with a CDR-H1 of SEQ ID NO: 33, the CDR-L3 has at least about 50%, 75%, 80%, 85%, 90%, or 95% identity with a CDR-L3 of SEQ ID NO: 40, the CDR-L2 has at least about 50%, 75%, 80%, 85%, 90%, or 95% identity with a CDR-L2 of SEQ ID NO: 39, and the CDR-L1 has at least about 50%, 75%, 80%, 85%, 90%, or 95% identity with a CDR-L1 of SEQ ID NO: 38. In some embodiments, the CDR-H3 is a CDR-H3 of SEQ ID NO: 35, with up to 1, 2, 3, 4, 5, 6, 7, or 8 amino acid substitutions; the CDR-H2 is a CDR-H2 of SEQ ID NO: 34, with up to 1, 2, 3, 4, 5, 6, 7, or 8 amino acid substitutions; the CDR-H1 is a CDR-H1 of SEQ ID NO: 33, with up to 1, 2, 3, 4, or 5 amino acid substitutions; the CDR-L3 is a CDR-L3 of SEQ ID NO: 40, with up to 1, 2, 3, 4, or 5 amino acid substitutions; the CDR-L2 is a CDR-L2 of SEQ ID NO: 39, with up to 1, 2, 3, or 4 amino acid substitutions; and the CDR-L1 is a CDR-L1 of SEQ ID NO: 38 with up to 1, 2, 3, 4, 5, or 6 amino acid substitutions.

In some embodiments, an antibody provided herein comprises a CDR-H3 of SEQ ID NO: 45, a CDR-H2 of SEQ ID NO: 44, a CDR-H1 of SEQ ID NO: 43, a CDR-L3 of SEQ ID NO: 50, a CDR-L2 of SEQ ID NO: 49, and a CDR-L1 of SEQ ID NO: 48. In some embodiments, the CDR-H3 has at least about 50%, 75%, 80%, 85%, 90%, or 95% identity with a CDR-H3 of SEQ ID NO: 45, the CDR-H2 has at least about 50%, 75%, 80%, 85%, 90%, or 95% identity with a CDR-H2 of SEQ ID NO: 44, the CDR-H1 has at least about 50%, 75%, 80%, 85%, 90%, or 95% identity with a CDR-H1 of SEQ ID NO: 43, the CDR-L3 has at least about 50%, 75%, 80%, 85%, 90%, or 95% identity with a CDR-L3 of SEQ ID NO: 50, the CDR-L2 has at least about 50%, 75%, 80%, 85%, 90%, or 95% identity with a CDR-L2 of SEQ ID NO: 49, and the CDR-L1 has at least about 50%, 75%, 80%, 85%, 90%, or 95% identity with a CDR-L1 of SEQ ID NO: 48. In some embodiments, the CDR-H3 is a CDR-H3 of SEQ ID NO: 45, with up to 1, 2, 3, 4, 5, 6, 7, or 8 amino acid substitutions; the CDR-H2 is a CDR-H2 of SEQ ID NO: 44, with up to 1, 2, 3, 4, 5, 6, 7, or 8 amino acid substitutions; the CDR-H1 is a CDR-H1 of SEQ ID NO: 43, with up to 1, 2, 3, 4, or 5 amino acid substitutions; the CDR-L3 is a CDR-L3 of SEQ ID NO: 50, with up to 1, 2, 3, 4, or 5 amino acid substitutions; the CDR-L2 is a CDR-L2 of SEQ ID NO: 49, with up to 1, 2, 3, or 4 amino acid substitutions; and the CDR-L1 is a CDR-L1 of SEQ ID NO: 48 with up to 1, 2, 3, 4, 5, or 6 amino acid substitutions.

In some embodiments, an antibody provided herein comprises a CDR-H3 of SEQ ID NO: 55, a CDR-H2 of SEQ ID NO: 54, a CDR-H1 of SEQ ID NO: 53, a CDR-L3 of SEQ ID NO: 60, a CDR-L2 of SEQ ID NO: 59, and a CDR-L1 of SEQ ID NO: 58. In some embodiments, the CDR-H3 has at least about 50%, 75%, 80%, 85%, 90%, or 95% identity with a CDR-H3 of SEQ ID NO: 55, the CDR-H2 has at least about 50%, 75%, 80%, 85%, 90%, or 95% identity with a CDR-H2 of SEQ ID NO: 54, the CDR-H1 has at least about 50%, 75%, 80%, 85%, 90%, or 95% identity with a CDR-H1 of SEQ ID NO: 53, the CDR-L3 has at least about 50%, 75%, 80%, 85%, 90%, or 95% identity with a CDR-L3 of SEQ ID NO: 60, the CDR-L2 has at least about 50%, 75%, 80%, 85%, 90%, or 95% identity with a CDR-L2 of SEQ ID NO: 59, and the CDR-L1 has at least about 50%, 75%, 80%, 85%, 90%, or 95% identity with a CDR-L1 of SEQ ID NO: 58. In some embodiments, the CDR-H3 is a CDR-H3 of SEQ ID NO: 55, with up to 1, 2, 3, 4, 5, 6, 7, or 8 amino acid substitutions; the CDR-H2 is a CDR-H2 of SEQ ID NO: 54, with up to 1, 2, 3, 4, 5, 6, 7, or 8 amino acid substitutions; the CDR-H1 is a CDR-H1 of SEQ ID NO: 53, with up to 1, 2, 3, 4, or 5 amino acid substitutions; the CDR-L3 is a CDR-L3 of SEQ ID NO: 60, with up to 1, 2, 3, 4, or 5 amino acid substitutions; the CDR-L2 is a CDR-L2 of SEQ ID NO: 59, with up to 1, 2, 3, or 4 amino acid substitutions; and the CDR-L1 is a CDR-L1 of SEQ ID NO: 58 with up to 1, 2, 3, 4, 5, or 6 amino acid substitutions.

In some aspects, the amino acid substitutions are conservative amino acid substitutions. In some embodiments, the antibodies described herein are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO: 5, 15, 25, 35, 45, or 55. In some aspects, the CDR-H3 has at least about 50%, 75%, 80%, 85%, 90%, or 95% identity with a CDR-H3 of SEQ ID NO: 5, 15, 25, 35, 45, or 55. In some embodiments, the CDR-H3 is a CDR-H3 selected of SEQ ID NO: 5, 15, 25, 35, 45, or 55, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-H2 of SEQ ID NO: 4, 14, 24, 34, 44, or 54. In some aspects, the CDR-H2 has at least about 50%, 75%, 80%, 85%, 90%, or 95% identity with a CDR-H2 of SEQ ID NO: 4, 14, 24, 34, 44, or 54. In some embodiments, the CDR-H2 is a CDR-H2 of SEQ ID NO: 4, 14, 24, 34, 44, or 54, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-H1 of SEQ ID NO: 3, 13, 23, 33, 43, or 53. In some aspects, the CDR-H1 has at least about 50%, 75%, 80%, 85%, 90%, or 95% identity with a CDR-H1 of SEQ ID NO: 3, 13, 23, 33, 43, or 53. In some embodiments, the CDR-H1 is a CDR-H1 of SEQ ID NO: 3, 13, 23, 33, 43, or 53, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-H3 of SEQ ID NO: 5, 15, 25, 35, 45, or 55, a CDR-H2 of SEQ ID NO: 4, 14, 24, 34, 44, or 54, and a CDR-H1 of SEQ ID NO: 3, 13, 23, 33, 43, or 53. In some embodiments, the CDR-H3 has at least about 50%, 75%, 80%, 85%, 90%, or 95% identity with a CDR-H3 of SEQ ID NO: 5, 15, 25, 35, 45, or 55, the CDR-H2 has at least about 50%, 75%, 80%, 85%, 90%, or 95% identity with a CDR-H2 of SEQ ID NO: 4, 14, 24, 34, 44, or 54, and the CDR-H1 has at least about 50%, 75%, 80%, 85%, 90%, or 95% identity with a CDR-H1 of SEQ ID NO3, 13, 23, 33, 43, or 53. In some embodiments, the CDR-H3 is a CDR-H3 of SEQ ID NO: 5, 15, 25, 35, 45, or 55, with up to 1, 2, 3, 4, 5, 6, 7, or 8 amino acid substitutions; the CDR-H2 is a CDR-H2 of SEQ ID NO: 34, 14, 24, 34, 44, or 54, with up to 1, 2, 3, 4, 5, 6, 7, or 8 amino acid substitutions; and the CDR-H1 is a CDR-H1 of SEQ ID NO: 3, 13, 23, 33, 43, or 53, with up to 1, 2, 3, 4, or 5 amino acid substitutions. In some aspects, the amino acid substitutions are conservative amino acid substitutions.

In some embodiments, an antibody provided herein comprises a CDR-L3 of SEQ ID NO: 10, 20, 30, 40, 50, or 60. In some aspects, the CDR-L3 has at least about 50%, 75%, 80%, 85%, 90%, or 95% identity with a CDR-L3 of SEQ ID NO: 10, 20, 30, 40, 50, or 60. In some embodiments, the CDR-L3 is a CDR-L3 of SEQ ID NO: 10, 20, 30, 40, 50, or 60, with up to 1, 2, 3, 4, 5, 6, 7, or 8 amino acid substitutions. In some aspects, the amino acid substitutions are conservative amino acid substitutions.

In some embodiments, an antibody provided herein comprises a CDR-L2 of SEQ ID NO: 9, 19, 29, 39, 49, or 59. In some aspects, the CDR-L2 has at least about 50%, 75%, 80%, 85%, 90%, or 95% identity with a CDR-L2 of SEQ ID NO: 9, 19, 29, 39, 49, or 59. In some embodiments, the CDR-L2 is a CDR-L2 of SEQ ID NO: 9, 19, 29, 39, 49, or 59, with up to 1, 2, 3, 4, 5, 6 or 7 amino acid substitutions. In some aspects, the amino acid substitutions are conservative amino acid substitutions.

In some embodiments, an antibody provided herein comprises a CDR-L1 of SEQ ID NO: 8, 18, 28, 38, 48, or 58. In some aspects, the CDR-L1 has at least about 50%, 75%, 80%, 85%, 90%, or 95% identity with a CDR-L1 of SEQ ID NO: 8, 18, 28, 38, 48, or 58. In some embodiments, the CDR-L1 is a CDR-L1 of SEQ ID NO: 8, 18, 28, 38, 48, or 58, with up to 1, 2, 3, 4, 5, 6, or 7 amino acid substitutions.

In some aspects, the amino acid substitutions are conservative amino acid substitutions. In some embodiments, an antibody provided herein comprises a CDR-L3 of SEQ ID NO: 10, 20, 30, 40, 50, or 60, and a CDR-L2 of SEQ ID NO9, 19, 29, 39, 49, or 59. In some embodiments, an antibody provided herein comprises a CDR-L3 of SEQ ID NO: 10, 20, 30, 40, 50, or 60, a CDR-L2 of SEQ ID NO: 9, 19, 29, 39, 49, or 59, and a CDR-L1 of SEQ ID NO: 8, 18, 28, 38, 48, or 58. In some embodiments, the CDR-L3 has at least about 50%, 75%, 80%, 85%, 90%, or 95% identity with a CDR-L3 of SEQ ID NO: 10, 20, 30, 40, 50, or 60, the CDR-L2 has at least about 50%, 75%, 80%, 85%, 90%, or 95% identity with a CDR-L2 of SEQ ID NO: 9, 19, 29, 39, 49, or 59, and the CDR-L1 has at least about 50%, 75%, 80%, 85%, 90%, or 95% identity with a CDR-L1 of SEQ ID NO: 8, 18, 28, 38, 48, or 58. In some embodiments, the CDR-L3 is a CDR-L3 of SEQ ID NO: 10, 20, 30, 40, 50, or 60, with up to 1, 2, 3, 4, or 5 amino acid substitutions; the CDR-L2 is a CDR-L2 of SEQ ID NO: 9, 19, 29, 39, 49, or 59, with up to 1, 2, 3, or 4 amino acid substitutions; and the CDR-L1 is a CDR-L1 of SEQ ID NO: 8, 18, 28, 38, 48, or 58, with up to 1, 2, 3, 4, 5, or 6 amino acid substitutions. In some aspects, the amino acid substitutions are conservative amino acid substitutions.

In some embodiments, an antibody provided herein comprises one to three CDRs of a $V_H$ domain selected from SEQ ID NOs: 2, 12, 22, 32, 42, or 52. In some embodiments, an antibody provided herein comprises two to three CDRs of a $V_H$ domain selected from SEQ ID NOs: 2, 12, 22, 32, 42, or 52. In some embodiments, an antibody provided herein comprises three CDRs of a VH domain selected from SEQ ID NOs: 2, 12, 22, 32, 42, or 52. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDR-H1 is a CDR-H1 of a VH domain selected from SEQ ID NOs: 2, 12, 22, 32, 42, or 52, with up to 1, 2, 3, 4, or 5 amino acid substitutions. In some embodiments, the CDR-H2 is a CDR-H2 of a VH domain selected from SEQ ID NOs: 2, 12, 22, 32, 42, or 52, with up to 1, 2, 3, 4, 5, 6, 7, or 8 amino acid substitutions. In some embodiments, the CDR-H3 is a CDR-H3 of a VH domain selected from SEQ ID NOs: 2, 12, 22, 32, 42, or 52, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VL domain selected from SEQ ID NOs: 7, 17, 27, 37, 47, or 57. In some embodiments, an antibody provided herein comprises two to three CDRs of a VL domain selected from SEQ ID NOs: 7, 17, 27, 37, 47, or 57. In some embodiments, an antibody provided herein comprises three CDRs of a VL domain selected from SEQ ID NOs: 7, 17, 27, 37, 47, or 57. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDR-L1 is a CDR-L1 of a VL domain selected from SEQ ID NOs: 7, 17, 27, 37, 47, or 57, with up to 1, 2, 3, 4, or 5 amino acid substitutions. In some embodiments, the CDR-L2 is a CDR-L2 of a VL domain selected from SEQ ID NOs: 7, 17, 27, 37, 47, or 57 with up to 1, 2, 3, 4, 5, 6, or 7 amino acid substitutions. In some embodiments, the CDR-L3 is a CDR-L3 of a VL domain selected from SEQ ID NOs: 7, 17, 27, 37, 47, or 57 with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VH domain selected from SEQ ID NOs: 2, 12, 22, 32, 42, or 52, and one to three CDRs of a VL domain selected from SEQ ID NOs: 7, 17, 27, 37, 47, or 57. In some embodiments, an antibody provided herein comprises two to three CDRs of a VH domain selected from SEQ ID NOs: 2, 12, 22, 32, 42, or 52, and two to three CDRs of a VL domain selected from SEQ ID NOs: 7, 17, 27, 37, 47, or 57. In some embodiments, an antibody provided herein comprises three CDRs of a VH domain selected from SEQ ID NOs: 2, 12, 22, 32, 42, or 52, and three CDRs of a VL domain selected from SEQ ID NOs: 7, 17, 27, 37, 47, or 57. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

$V_H$ Domains

In some embodiments, an antibody provided herein comprises a $V_H$ sequence selected from SEQ ID NOs: 2, 12, 22, 32, 42, or 52. In some embodiments, an antibody provided herein comprises a $V_H$ sequence of SEQ ID NO: 2. In some embodiments, an antibody provided herein comprises a $V_H$ sequence of SEQ ID NO: 12. In some embodiments, an antibody provided herein comprises a $V_H$ sequence of SEQ ID NO: 22. In some embodiments, an antibody provided herein comprises a $V_H$ sequence of SEQ ID NO: 32. In some embodiments, an antibody provided herein comprises a $V_H$ sequence of SEQ ID NO: 42. In some embodiments, an antibody provided herein comprises a $V_H$ sequence of SEQ ID NO: 52

In some embodiments, the $V_H$ sequence has at least 70%, 80%, or 90% identity with SEQ ID NO: 2, wherein any variation from SEQ ID NO: 2 does not occur within CDR-H1, CDR-H2, or CDR-H3. In some embodiments, the $V_H$ sequence has at least 70%, 80%, or 90% identity with SEQ ID NO: 12, wherein any variation from SEQ ID NO: 12 does not occur within CDR-H1, CDR-H2, or CDR-H3. In some embodiments, the $V_H$ sequence has at least 70%, 80%, or 90% identity with SEQ ID NO: 22, wherein any variation from SEQ ID NO: 22 does not occur within CDR-H1, CDR-H2, or CDR-H3. In some embodiments, the $V_H$ sequence has at least 70%, 80%, or 90% identity with SEQ ID NO: 32, wherein any variation from SEQ ID NO: 32 does not occur within CDR-H1, CDR-H2, or CDR-H3. In some embodiments, the $V_H$ sequence has at least 70%, 80%, or 90% identity with SEQ ID NO: 42, wherein any variation from SEQ ID NO: 42 does not occur within CDR-H1, CDR-H2, or CDR-H3. In some embodiments, the $V_H$ sequence has at least 70%, 80%, or 90% identity with SEQ ID NO: 52, wherein any variation from SEQ ID NO: 52 does not occur within CDR-H1, CDR-H2, or CDR-H3.

In some embodiments, an antibody provided herein comprises a $V_H$ sequence having at least about 50%, 60%, 70%, 80%, 90%, 95%, or 99% identity to SEQ ID NO: 2. In some embodiments, an antibody provided herein comprises a $V_H$ sequence having at least about 50%, 60%, 70%, 80%, 90%, 95%, or 99% identity to SEQ ID NO: 12. In some embodiments, an antibody provided herein comprises a $V_H$ sequence having at least about 50%, 60%, 70%, 80%, 90%, 95%, or 99% identity to SEQ ID NO: 22. In some embodiments, an antibody provided herein comprises a $V_H$ sequence having at least about 50%, 60%, 70%, 80%, 90%, 95%, or 99% identity to SEQ ID NO: 32. In some embodiments, an antibody provided herein comprises a $V_H$ sequence having at least about 50%, 60%, 70%, 80%, 90%, 95%, or 99% identity to SEQ ID NO: 42. In some embodiments, an antibody provided herein comprises a $V_H$ sequence having at least about 50%, 60%, 70%, 80%, 90%, 95%, or 99% identity to SEQ ID NO: 52.

In some embodiments, an antibody provided herein comprises a $V_H$ sequence having at least about 50%, 60%, 70%, 80%, 90%, 95%, or 99% identity to an illustrative $V_H$ sequence provided in SEQ ID NOs: 2, 12, 22, 32, 42, or 52. In some embodiments, an antibody provided herein comprises a $V_H$ sequence provided in SEQ ID NOs: 2, 12, 22, 32, 42, or 52, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

$V_L$ Domains

In some embodiments, an antibody provided herein comprises a $V_L$ sequence selected from SEQ ID NOs: 7, 17, 27, 37, 47, or 57. In some embodiments, an antibody provided herein comprises a $V_L$ sequence of SEQ ID NO: 7. In some embodiments, an antibody provided herein comprises a $V_L$ sequence of SEQ ID NO: 17. In some embodiments, an antibody provided herein comprises a $V_L$ sequence of SEQ ID NO: 27. In some embodiments, an antibody provided herein comprises a $V_L$ sequence of SEQ ID NO: 37. In some embodiments, an antibody provided herein comprises a $V_L$ sequence of SEQ ID NO: 47. In some embodiments, an antibody provided herein comprises a $V_L$ sequence of SEQ ID NO: 57.

In some embodiments, the $V_L$ sequence has at least 70%, 80%, or 90% identity with SEQ ID NO: 7, wherein any variation from SEQ ID NO: 7 does not occur within CDR-L1, CDR-L2, or CDR-L3. In some embodiments, the $V_L$ sequence has at least 70%, 80%, or 90% identity with SEQ ID NO: 17, wherein any variation from SEQ ID NO: 17 does not occur within CDR-L1, CDR-L2, or CDR-L3. In some embodiments, the $V_L$ sequence has at least 70%, 80%, or 90% identity with SEQ ID NO: 27, wherein any variation from SEQ ID NO: 27 does not occur within CDR-L1, CDR-L2, or CDR-L3. In some embodiments, the $V_L$ sequence has at least 70%, 80%, or 90% identity with SEQ ID NO: 37, wherein any variation from SEQ ID NO: 37 does not occur within CDR-L1, CDR-L2, or CDR-L3. In some embodiments, the $V_L$ sequence has at least 70%, 80%, or 90% identity with SEQ ID NO: 47, wherein any variation from SEQ ID NO: 47 does not occur within CDR-L1, CDR-L2, or CDR-L3. In some embodiments, the $V_L$ sequence has at least 70%, 80%, or 90% identity with SEQ ID NO: 57, wherein any variation from SEQ ID NO: 57 does not occur within CDR-L1, CDR-L2, or CDR-L3.

In some embodiments, an antibody provided herein comprises a $V_L$ sequence having at least about 50%, 60%, 70%, 80%, 90%, 95%, or 99% identity to SEQ ID NO: 7. In some embodiments, an antibody provided herein comprises a $V_L$ sequence having at least about 50%, 60%, 70%, 80%, 90%, 95%, or 99% identity to SEQ ID NO: 17. In some embodiments, an antibody provided herein comprises a $V_L$ sequence having at least about 50%, 60%, 70%, 80%, 90%, 95%, or 99% identity to SEQ ID NO: 27. In some embodiments, an antibody provided herein comprises a $V_L$ sequence having at least about 50%, 60%, 70%, 80%, 90%, 95%, or 99% identity to SEQ ID NO: 37. In some embodiments, an antibody provided herein comprises a $V_L$ sequence having at least about 50%, 60%, 70%, 80%, 90%, 95%, or 99% identity to SEQ ID NO: 47. In some embodiments, an antibody provided herein comprises a $V_L$ sequence having at least about 50%, 60%, 70%, 80%, 90%, 95%, or 99% identity to SEQ ID NO: 57.

In some embodiments, an antibody provided herein comprises a $V_L$ sequence having at least about 50%, 60%, 70%, 80%, 90%, 95%, or 99% identity to an illustrative $V_L$ sequence provided in SEQ ID NOs: 7, 17, 27, 37, 47, or 57. In some embodiments, an antibody provided herein comprises a $V_L$ sequence provided in SEQ ID NOs: 7, 17, 27, 37, 47, or 57, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

$V_H$-$V_L$ Combinations

In some embodiments, an antibody provided herein comprises a $V_H$ sequence selected from SEQ ID NOs: 2, 12, 22, 32, 42, or 52; and a $V_L$ sequence selected from SEQ ID NOs: 7, 17, 27, 37, 47, or 57.

In some embodiments, an antibody provided herein comprises a $V_H$ sequence of SEQ ID NO: 2 and a $V_L$ sequence of SEQ ID NO: 7. In some embodiments, an antibody provided herein comprises a $V_H$ sequence of SEQ ID NO: 12 and a $V_L$ sequence of SEQ ID NO: 17. In some embodiments, an antibody provided herein comprises a $V_H$ sequence of SEQ ID NO: 22 and $V_L$ sequence of SEQ ID NO: 27. In some embodiments, an antibody provided herein comprises a $V_H$ sequence of SEQ ID NO: 32 and a $V_L$ sequence of SEQ ID NO: 37. In some embodiments, an antibody provided herein comprises a $V_H$ sequence of SEQ ID NO: 42 and a $V_L$ sequence of SEQ ID NO: 47. In some embodiments, an antibody provided herein comprises a $V_H$ sequence of SEQ ID NO: 52 and a $V_L$ sequence of SEQ ID NO: 57

In some embodiments, the $V_H$ sequence has at least 70%, 80%, or 90% identity with SEQ ID NO: 2 and wherein the variable region of the light chain has at least 70%, 80%, or 90% identity with SEQ ID NO: 7, wherein any variation from SEQ ID NO: 2 does not occur within CDR-H1, CDR-H2, or CDR-H3 and wherein any variation from SEQ ID NO: 7 does not occur within CDR-L1, CDR-L2, or CDR-L3. In some embodiments, the $V_H$ sequence has at least 70%, 80%, or 90% identity with SEQ ID NO: 12 and wherein the variable region of the light chain has at least 70%, 80%, or 90% identity with SEQ ID NO: 17, wherein any variation from SEQ ID NO: 12 does not occur within CDR-H1, CDR-H2, or CDR-H3 and wherein any variation from SEQ ID NO: 17 does not occur within CDR-L1, CDR-L2, or CDR-L3. In some embodiments, the $V_H$ sequence has at least 70%, 80%, or 90% identity with SEQ ID NO: 22 and wherein the variable region of the light chain has at least 70%, 80%, or 90% identity with SEQ ID NO: 27, wherein any variation from SEQ ID NO: 22 does not occur within CDR-H1, CDR-H2, or CDR-H3 and wherein any variation from SEQ ID NO: 27 does not occur within CDR-L1, CDR-L2, or CDR-L3. In some embodiments, the $V_H$ sequence has at least 70%, 80%, or 90% identity with SEQ ID NO: 32 and wherein the variable region of the light chain has at least 70%, 80%, or 90% identity with SEQ ID NO: 37, wherein any variation from SEQ ID NO: 32 does not occur within CDR-H1, CDR-H2, or CDR-H3 and wherein any variation from SEQ ID NO: 37 does not occur within CDR-L1, CDR-L2, or CDR-L3. In some embodiments, the $V_H$ sequence has at least 70%, 80%, or 90% identity with SEQ ID NO: 42 and wherein the variable region of the light chain has at least 70%, 80%, or 90% identity with SEQ ID NO: 47, wherein any variation from SEQ ID NO: 42 does not occur within CDR-H1, CDR-H2, or CDR-H3 and wherein any variation from SEQ ID NO: 47 does not occur within CDR-L1, CDR-L2, or CDR-L3. In some embodiments, the $V_H$ sequence has at least 70%, 80%, or 90% identity with SEQ ID NO: 52 and wherein the variable region of the light chain has at least 70%, 80%, or 90% identity with SEQ ID NO: 57, wherein any variation from SEQ ID NO: 52 does not occur within CDR-H1, CDR-H2, or CDR-H3 and wherein any variation from SEQ ID NO: 57 does not occur within CDR-L1, CDR-L2, or CDR-L3.

In certain aspects, any of SEQ ID NOs: 2, 12, 22, 32, 42, or 52 can be combined with any of SEQ ID NOs: 7, 17, 27, 37, 47, or 57. For example, SEQ ID NO: 2 can be combined with any of SEQ ID NO: 7, 17, 27, 37, 47, or 57. As another example, SEQ ID NO: 17 can be combined with any of SEQ ID NO: 2, 12, 22, 32, 42, or 52.

In some embodiments, an antibody provided herein comprises a $V_H$ sequence having at least about 50%, 60%, 70%, 80%, 90%, 95%, or 99% identity to an illustrative $V_H$ sequence provided in SEQ ID NOs: 2, 12, 22, 32, 42, or 52; and a $V_L$ sequence having at least about 50%, 60%, 70%, 80%, 90%, 95%, or 99% identity to an illustrative $V_L$ sequence provided in SEQ ID NOs: 7, 17, 27, 37, 47, or 57. In some embodiments, an antibody provided herein comprises a $V_H$ sequence provided in SEQ ID NOs: 2, 12, 22, 32, 42, or 52 with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a $V_L$ sequence provided in SEQ ID NOs: 7, 17, 27, 37, 47, or 57, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, the percent homology of the variable heavy or variable light chain is to be calculated outside the CDRs. For instance, the percent homology can be calculated in the framework regions In some embodiments, an antibody comprises a heavy chain provided in SEQ ID NOs: 1, 11, 21, 31 41, or 51.

In some embodiments, an antibody comprises a light chain provided in SEQ ID NOs: 6, 16, 26, 36, 46, or 56.

In certain aspects, any of SEQ ID NOs: 1, 11, 21, 31 41, or 51 can be combined with any of SEQ ID NOs: 6, 16, 26, 36, 46, or 56.

In some embodiments, an antibody provided herein comprises a heavy chain sequence having at least about 50%, 60%, 70%, 80%, 90%, 95%, or 99% identity to an illustrative heavy chain sequence provided in SEQ ID NOs: 1, 11, 21, 31 41, or 51; and a light chain sequence having at least about 50%, 60%, 70%, 80%, 90%, 95%, or 99% identity to an illustrative light chain sequence provided in SEQ ID NOs: 6, 16, 26, 36, 46, or 56. In some embodiments, an antibody provided herein comprises a heavy chain sequence provided in SEQ ID NOs: 1, 11, 21, 31 41, or 51 with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a light chain sequence provided in SEQ ID NOs: 6, 16, 26, 36, 46, or 56, with up to 1, 2, 3, 4, 5, 6, 7, 8, 9, 10, 11, 12, 13, 14, 15, 16, 17, 18, 19, 20, 21, 22, 23, 24, or 25 amino acid substitutions.

Fc Region

The term "Fc domain" or "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, MD, 1991. An "Fc polypeptide" of a dimeric Fc as used herein refers to one of the two polypeptides forming the dimeric Fc domain, i.e. a polypeptide comprising C-terminal constant regions of an immunoglobulin heavy chain, capable of stable self-association. For example, an Fc polypeptide of a dimeric IgG Fc comprises an IgG CH2 and an IgG CH3 constant domain sequence. An Fc can be of the class IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$.

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., Immuno Biology: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976); and Kim et al., J. Immunol. 24:249 (1994)).

In some embodiments, an antibody is an IgG1 antibody. Modifications in the CH2 domain can affect the binding of FcRs to the Fc. A number of amino acid modifications in the Fc region are known in the art for selectively altering the affinity of the Fc for different Fc-gamma (Fcγ) receptors. In one embodiment, the Fc comprises one or more modifications to promote selective binding of Fc-gamma receptors.

In some embodiments an antibody described herein comprises an Fc region comprising an L234A/L235A mutation, according to the EU numbering system.

In some embodiments the antibodies are monoclonal antibodies. In some embodiments the antibodies are produced by hybridomas. In other embodiments, the antibodies are produced by recombinant cells engineered to express the desired variable and constant domains. In some embodiments, antibodies are specific for surface antigens, such as PAPP-A protein. In particular embodiments, the therapeutic antibodies may have human or non-human primate IgG1 Fc portions.

Binding

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule. Crosslinking of an antigen target is a type of binding. In some embodiments, an anti-PAPP-A antibody crosslinks PAPP-A to PAPP-A on a PAPP-A+ cell.

"Affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

The term "$k_d$" (sec$^{-1}$), as used herein, refers to the dissociation rate constant of a particular antibody-antigen interaction. This value is also referred to as the $k_{off}$ value.

The term "$k_a$" (M$^{-1}$×sec$^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D=k_d/k_a$. In some embodiments, the affinity of an antibody is described in terms of the $K_D$ for an interaction between such antibody and its antigen. For clarity, as known in the art, a smaller $K_D$ value indicates a higher affinity interaction, while a larger $K_D$ value indicates a lower affinity interaction.

The term "$K_A$" (M$^{-1}$), as used herein, refers to the association equilibrium constant of a particular antibody-antigen interaction. $K_A=k_a/k_d$.

In some embodiments, an antibody provided herein binds human PAPP-A. In some embodiments, an antibody provided herein binds mouse PAPP-A. In some embodiments, an antibody provided herein binds rhesus macaque PAPP-A. In some embodiments, an antibody provided herein binds cynomolgus PAPP-A. In some embodiments, an antibody provided herein binds human, rhesus macaque, and/or cynomolgus PAPP-A.

In some embodiments, an antibody provided herein binds human PAPP-A with a $K_D$ of less than or equal to about 1, 1.1, 1.2, 1.3, 1.4, 1.5, 1.6, 1.7, 1.8, 1.9, 1.95, 2, 3, 4, 5, 6, 7, 8, 9, 10, 25, 50, 75, or 100×10$^{-12}$ M, as measured by surface plasmon resonance assay. In some embodiments, the $K_D$ of the antibody provided herein is between about 0.5-1, 0.25-0.75, 0.25-0.5, 0.5-0.75, 0.75-1, 0.75-2, 1.1-1.2, 1.2-1.3, 1.3-1.4, 1.4-1.5, 1.5-1.6, 1.6-1.7, 1.7-1.8, 1.8-1.9, 1.9-2, 1-2, 1-5, 2-7, 3-8, 3-5, 4-6, 5-7, 6-8, 7-9, 7-10, 5-10, 10-20, 20-30, 30-40, 40-50, 50-60, 60-70, 70-80, 80-90, or 90-100×10$^{-12}$ M, as measured by surface plasmon resonance assay.

In some embodiments, the antibody provided herein binds human PAPP-A with a $K_D$ of less than or equal to about 3, 2.5, 2.3, 2, 1.98, 1.95, 1.9, 1.85, 1.8, 1.75, 1.7, 1.65, 1.6, 1.55, 1.50, 1.45, or 1.4×10$^{-12}$ M, or less, as measured by surface plasmon resonance assay. In some embodiments, the antibody provided herein binds human PAPP-A with a $K_D$ between 2.5-2.3, 2.5-2.0, 2.0-1.9, 1.9-1.8, 1.8-1.7, 1.7-1.6, 1.6-1.5, or 1.9-1.5×10$^{-12}$ M as measured by surface plasmon resonance.

In some embodiments, the antibody provided herein inhibits PAPP-A proteolytic activity with an IC50 of less than or equal to 3.5, 3, 2.5, 2, 1.9, 1.8, 1.7, 1.6, 1.5, 1.4, 1.3, 1.2, 1.1, 0.9, 0.8, 0.7, 0.6, 0.5, 0.4, 0.3, 0.2, 0.1, 0.9, 0.8, 0.7, 0.6, 0.5, 0.4, 0.3, 0.2, 0.1, 0.09, 0.08, 0.07, 0.06, 0.05, or 0.04 nM as measured by measured by flow cytometry or western blotting. In some embodiments, the antibody provided herein inhibits PAPP-A proteolytic activity against IGFBP-2, IGFBP-4, or IGFBP-5.

To screen for antibodies which bind to an epitope on a target antigen bound by an antibody of interest (e.g., PAPP-A), a routine cross-blocking assay such as that described in *Antibodies, A Laboratory Manual*, Cold Spring Harbor Laboratory, Ed Harlow and David Lane (1988), can be performed. Alternatively, or additionally, epitope mapping can be performed by methods known in the art.

Function

In some embodiments, an antibody is an antagonistic antibody. An antagonistic antibody can block (e.g. decrease) one or more activities or functions of PAPP-A after the antibody binds to the PAPP-A protein. For example, the antagonist antibody may bind to and block binding of the PAPP-A enzyme to its substrate, preventing cleavage of the substrate.

Methods

Method of Treating PAPP-A Associated Disorders

In another aspect provided herein are methods of treating a PAPP-A associated disorder comprising administering to a subject an effective amount of a composition comprising an anti-PAPP-A antibody. In some embodiments, the PAPP-A associated disorder is kidney disease, for example, polycystic kidney disease, or autosomal dominant polycystic kidney disease (ADPKD).

In some embodiments, the kidney disease is polycystic kidney disease or autosomal dominant polycystic kidney disease (ADPKD).

In one embodiment, the subject is a human.

Pharmaceutical Compositions

Methods for treatment of PAPP-A associated disorders are also encompassed by the present disclosure. Said methods include administering a therapeutically effective amount of an anti-PAPP-A antibody or antigen-binding fragment. The PAPP-A antibody or antigen-binding fragment can be formulated in pharmaceutical compositions or as a medicament.

Kits and Articles of Manufacture

The present application provides kits comprising any one or more of the antibody compositions described herein. In some embodiments, the kits further contain a component selected from any of secondary antibodies, reagents for immunohistochemistry analysis, pharmaceutically acceptable excipient and instruction manual and any combination thereof. In one specific embodiment, the kit comprises a pharmaceutical composition comprising any one or more of the antibody compositions described herein, with one or more pharmaceutically acceptable excipients.

The present application also provides articles of manufacture comprising any one of the antibody compositions or kits described herein. Examples of an article of manufacture include vials.

EXAMPLES

Below are examples of specific embodiments for carrying out the present disclosure. The examples are offered for illustrative purposes only and are not intended to limit the scope of the present disclosure in any way. Efforts have been made to ensure accuracy with respect to numbers used (e.g., amounts, temperatures, etc.), but some experimental error and deviation should, of course, be allowed for.

The practice of the present disclosure will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* $3^{rd}$ Ed. (Plenum Press) Vols A and B (1992).

Example 1: Identifying Anti-PAPP-A Monoclonal Antibodies

Yeast display technology was used to identify antibodies specifically binding to PAPP-A. The objective of this work was to generate fully human antibodies that bind to and neutralize human and cynomolgus monkey (NHP) PAPP-A with high affinity and potency. Briefly, six human synthetic scFv (single chain fragment variable) antibody libraries were selected for binders to PAPP-A. Each library was composed of a single human VH germline, highly diverse HCDR3 fragment ranging in size from 7 to 18 amino-acids, and a diverse mix of VK germlines. Using a biotinylated PAPP-A protein as a target, the scFv fragments were selected using both magnetic and fluorescence activated cell sorting technologies. Selection outputs were analyzed by sequencing and categorized using GeneData Biologics® (GeneData, Lexington, MA, USA). Non-redundant clones were converted to IgG, expressed in EXPI293 (HEK293) cells (Gibco/Fisher) and screened for binding to PAPP-A. In total, 111 clones expressed as IgG demonstrated specific binding to human PAPP-A.

Example 2. Inhibition of PAPP-A Proteolytic Activity by Monoclonal Antibodies

By inhibiting the proteolytic activity of PAPP-A, IGF bioavailability and downstream signaling can be modulated. A graphic representation of the assay for inhibition of PAPP-A proteolytic activity, neutralizing PAPP-A activity is shown in FIG. 1.

Protein Expression

Full length PAPP-A protein was expressed for human, NHP and mouse in stably transduced HEK293 cell line and purified by heparin column chromatography. Human IGFBP-4 protein with N-terminal 6His tag and C-terminal Flag-tag was produced recombinantly by transient expression in HEK293 cells and purified by Ni-Sepharose column chromatography. Similarly, human IGFBP-2 and human IGFBP-5 proteins were expressed with a 6His tag and C-terminal Flag-tag and purified. Prior to initiating the studies, full-length PAPP-A protein activity was confirmed in preliminary assays.

Enzymatic Cleavage Experiments

For enzymatic cleavage reaction, IGFBP-2 and IGFBP-4 proteins were pre-incubated with human IGF-1 (Bio-techne®/R&D Systems, Minneapolis, MN, USA) for 30 minutes at 37° C. in enzymatic assay buffer consists of Dulbecco's modified Eagle medium (DMEM; ThermoFisher/Gibco, Waltham, MA, USA) with 1% bovine serum albumin (ThermoFisher/Invitrogen). IGFBP/IGF-1 proteins were then mixed with PAPP-A in enzymatic assay buffer and incubated for two to four hours at 37° C.

For enzymatic cleavage reactions with IGFBP-5, the proteins were directly mixed with PAPP-A without IGF-1 pre-incubation, as addition of IGF-1 inhibits proteolytic activity of PAPP-A for IGFBP-5. Final concentration in IGFBP-4 cleavage reactions were: 90 nM for IGFBP-4, 566 nM for IGF-1 and 0.5 nM for PAPP-A. The final concentration in IGFBP-5 cleavage reactions were: 80 nM for IGFBP-5, and 0.05 nM for PAPP-A. Final concentration in IGFBP-2 cleavage reactions were: 80 nM for IGFBP-2, 566 nM for IGF-1 and 5 nM for PAPP-A.

Dilutions of monoclonal antibodies were prepared in enzymatic assay buffer from stock solutions to a working 1× initial concentration of 30 µg/ml, (200 nM), and an 8-point 3× dilution series was performed. Each antibody concentration was tested three times. PAPP-A protein was pre-incubated with the dilution series of anti-PAPP-A antibody prior to adding to IGFBP mix.

Analysis of PAPP-A Activity

Proteins were resolved by capillary electrophoresis on a Wes™ instrument (Bio-Techne®/ProteinSimple, Minneapolis, MN, USA) using a capillary cartridge kit (Bio-Teche®/ProteinSimple), probed with a polyclonal murine anti-His Tag antibody (GeneScript, Piscataway, NJ, USA) and visualized with an anti-mouse detection module (Bio-Techne®/ProteinSimple).

The relative percentage of uncut and cleaved IGFBP bands were quantified using Compass for Simple Western software (Bio-techne®/ProteinSimple). The inhibitory activity of the monoclonal antibodies for each concentration tested (S=IGFBP+PAPP-A+antibody) was evaluated by normalizing to control lanes (A=IGFBP only, B=IGFBP+PAPP-A) using the following equation:

$$\% \text{ Inhibition} = \frac{(\% \text{ uncut}, S - \% \text{ uncut}, B)}{(\% \text{ uncut}, A - \% \text{ uncut}, B)} \times 100\%$$

The 111 antibody clones expressed as IgG that showed binding to PAPP-A were screened for their ability to inhibit PAPP-A proteolytic activity. 101 clones fully or partially block cleavage of IGFBP4, while 57 clones fully or partially blocked cleavage of both IGFBP4 and IGFBP2. However, only a subset of 16 clones could fully or partially block cleavage of all three IGFBPs (IGFBP4, IGFBP2 and IGFBP5). Of these 16 clones, four clones with the best inhibition (neutralization) potency were selected. The most active two clones were represented by Ab5 and Ab6 in the table below. Two other antibody clones, with slightly lower neutralization activity were subjected to affinity maturation by CDR mutagenesis. Affinity maturation provided a means of selecting antibodies with improved substrate binding and better neutralization activity. From each of the affinity matured clones, two antibodies were derived: Ab1 and Ab2 resulted from one clone, while the second clone resulted in Ab3 and Ab4, as screened below.

Due to the different amounts of PAPP-A protein necessary to complete cleavage of different IGFBPs, $IC_{50}$ values for the different inhibition assays could not be compared directly but were a relative guide to inhibitory activity. However, for most of the Abs tested $IC_{50}$ values in each of the cleavage assays were in the sub-nM range (Table U). Only Ab5 showed reduced activity against the proteolysis of IGFBP-4 and IGFBP-5 as compared to the other five antibodies.

TABLE U

Antibody-mediated inhibition of PAPP-A proteolytic activity ($IC_{50}$) against substrates as determined by western blotting

| Substrate | Ab1 | Ab2 | Ab3 | Ab4 | Ab5 | Ab6 |
| --- | --- | --- | --- | --- | --- | --- |
| IGFBP-2 | 0.37 nM | 0.34 nM | 0.26 nM | 0.31 nM | 0.11 nM | 0.18 nM |
| IGFBP-4 | 0.1 nM | 0.4 nM | 0.1 nM | 0.1 nM | 1.88 nM | 0.12 nM |
| IGFBP-5 | 0.07 nM | 0.04 nM | 0.18 nM | 0.31 nM | 3.02 nM | 0.09 nM |

Example 3: Determination of Substrate Affinity of Anti-PAPP-A Antibodies to PAPP-A To determine the substrate affinity of the tested anti-PAPP-A antibodies to PAPP-A, surface plasmon resonance (SPR) binding analysis was used. The substrate affinity ($K_D$) of the monoclonal antibodies to human, NHP and mouse PAPP-A protein was evaluated.

Preparation of Biosensor Surface

A goat antibody specific to the Fc region of human IgG (Thermo Fisher Scientific, Waltham, MA, USA) was used to capture the monoclonal antibodies. The Fc specific antibody was covalently immobilized on carboxymethyl dextran matrix of the Biacore™ CM5 biosensor chip (Cytiva Life Sciences, Marlborough, MA, USA) via amino groups using an amine coupling kit (Cytiva) and the immobilization wizard option of the Biacore™ (Cytiva) instrument's controlling software. Carboxyl groups of the dextran matrix on the chip were activated with 100 mM N-hydroxysuccinimide and 400 mM 1-ethyl-3-(3-dimethylaminopropyl) carbodiimide hydrochloride. Goat anti-human IgG Fc (25 µg/mL; Thermo Fisher), diluted in 10 mM sodium acetate, pH 4.5, was injected across the activated surface. Once the level of binding response reached the targeted value of 10000 Resonance Units (RU), unreacted groups were deactivated by injection of 1 M ethanolamine. Approximately 10,000 RU of goat anti-human IgG Fc was immobilized on the chip surface of the flow cells, while a modified control matrix surface with similarly conjugated goat anti-human IgG Fc antibody was used as a reference surface.

Binding of Recombinant PAPP-A, to Immobilized anti-PAPP-A Antibodies

Anti-PAPP-A monoclonal antibodies were diluted in the running buffer (HEPES buffered saline; HBS-P+, Cytiva) plus 0.1 mg/mL bovine serum albumin) to the concentration of 1 µg/mL were injected over the goat anti-human IgG Fc surface at a flow rate of 50 µL/minute for 25 seconds to achieve capture level of ~100 to 110 RU. The net difference in the baseline signal and the signal after the completion of the antibody injection was taken to represent the amount of bound monoclonal antibody.

Each antigen binding experiment consisted of antigen association and antigen dissociation phases. Aliquots of recombinant PAPP-A proteins were injected at different concentrations at a flow rate of 50 µL/minute, for five minutes over the captured monoclonal antibodies and the reference surface to determine association rates. Each PAPP-A protein was tested at the following concentrations: 0, 0.04, 0.12, 0.37, 1.11, 3.33, 10, and 30 nM. The dissociation phase of PAPP-A consisted of continued flow of (HEPES-buffered saline; HBS-EP+, plus 0.1 mg/mL bovine serum albumin) buffer, at 50 µL/minute at various dissociation times (due to slow off-rates, dissociation times of 1 hour were allowed for higher concentrations of 3.33, 10, and 30 nM PAPP-A and 5 minutes for lower concentrations of 0.04, 0.12, 0.37, and 1.11 nM PAPP-A). The instrument response was measured in RU and is proportionate to the mass of bound PAPP-A antigens.

Immobilized surfaces were regenerated with 10 mM glycine, pH 1.5 (two consecutive 25 µL injections at a flow rate of 50 µL/minute) before injection of the next sample. Each interaction between monoclonal antibodies and each of the PAPP-A antigens was run in triplicate. Finally, the reference surface response was subtracted from the reaction surface data to eliminate change in the refractive index and injection noise.

Determination of Association and Dissociation Rates

The association rate constants ($k_a$, units of $M^{-1} s^{-1}$) were derived by kinetic binding measurements at several antigen concentrations. Dissociation rate constants ($k_d$, $s^{-1}$) were determined by measuring changes in the amount of antigen bound to the monoclonal antibodies over time after the association phase was complete. Association and dissociation rate constants were calculated by the instrument evaluation software based on the values extracted from the data using a global fit analysis, which allowed identical values for each parameter in the data set, except for $R_{max}$ that were set locally due to variation in antibody capture level. To calculate the overall apparent dissociation constant ($K_D$) for the interaction between monoclonal antibody and PAPP-A species, the apparent dissociation rate constants ($k_d$) and the apparent association rate constant ($k_a$), were used in the following formula: $K_D = k_d/k_a$.

Using these parameters, the substrate affinity was calculated between each of the antibodies and recombinant PAPP-A from human, NHP and mouse. Where the data were designated as less than a specific amount, the data were below the resolution of the instrument. Of the six tested anti-PAPP-A monoclonal antibodies, Ab1 and Ab6 showed the most similar and greater affinities for human, NHP and mouse PAPP-A as compared to the other four antibodies (Table T).

µg/mL (2.5 nM) and a 9-point 2.5× dilution series was performed. Antibody titration began at 1 nM for human PAPP-A. All antibody concentrations were tested in triplicate.

Testing and Analysis of Phosphorylated AKT

Monoclonal antibody was added to human PAPP-A and incubated for 30 minutes at ambient temperature. IGFBP-4 protein was mixed with IGF-1 and incubated for 30 minutes at ambient temperature. The antibody/PAPP-A mix was added to the IGFBP-4/IGF-1 mix and incubated for five hours at 37° C. Final concentrations in the reaction were 1.05 nM for IGFBP-4, 4.2 nM for IGF-1 and 0.55 nM for human PAPP-A.

IGF-1/IGFBP-4/PAPP-A/antibody mix was added to serum-starved HEK293 cells and incubated for 20 minutes at 37° C. Media was removed and cells were lysed in MSD Tris Lysis buffer (Meso Scale Diagnostics, Rockville, MD, USA) and analyzed by Phospho(Ser473)/Total Akt Whole Cell Lysate kit (Meso Scale Diagnostics) according to the manufacturer's protocol.

The data in Table V below indicate similar $IC_{50}$ values for each of the monoclonal antibodies assessed in this phosphorylation assay. Analysis of the data demonstrated that all the monoclonal antibodies inhibited release of biologically active IGF-1 by neutralizing PAPP-A proteolytic activity from IGFBP-4.

TABLE T

Substrate affinity ($K_D$) of monoclonal antibodies to PAPP-A from three species as determined by surface plasmon resonance (SPR) binding analysis

| Species | Ab1 | Ab2 | Ab3 | Ab4 | Ab5 | Ab6 |
|---|---|---|---|---|---|---|
| Human | <2.3 pM | <1.0 pM | <1.5 pM | 25 pM | 93 pM | <1.2 pM |
| NHP | 17 pM | 24 pM | 7.2 pM | 35 PM | 460 pM | <1.0 pM |
| Mouse | <2.9 pM | 91 pM | 120 pM | 860 pM | 180 pM | <3.0 pM |

Example 4. Antibody-Mediated Inhibition of AKT Phosphorylation

To assess the effect of monoclonal antibody inhibition of PAPP-A cleavage of IGFBP-4, phosphorylated AKT in HEK293 cells was performed in the assays with human full-length PAPP-A protein.

TABLE V

Antibody-mediated inhibition of IGF-1-induced AKT phosphorylation ($IC_{50}$) in HEK293 cells

| Substrate | Ab1 | Ab2 | Ab3 | Ab4 | Ab5 | Ab6 |
|---|---|---|---|---|---|---|
| IGF-1: IGFBP-4, PAPP-A | 0.25 nM | 0.26 nM | 0.19 nM | 0.22 nM | 0.21 nM | 0.25 nM |

Preparation of Cells and Anti-PAPP-A Antibodies

HEK293 cells were plated in serum-free Eagle minimal essential medium overnight. The following day, enzymatic reactions were set-up. Dilutions of anti-PAPP-A monoclonal antibodies were prepared in 0.015% bovine serum albumin Dulbecco's phosphate buffered saline media from stock solutions to a working 1× initial concentration of 0.375

Example 5. Non-Specific Binding of Anti-PAPP-A Antibodies to HEK293 Cells

The assessment of the anti-PAPP-A monoclonal antibodies for non-specific binding is a routine part of pre-clinical assessment as non-specific binding of antibody can lead to undesired outcome in vivo, from poor PK (pharmacokinetics) to toxicology findings.

Non-Specific Binding of Anti-PAPP-A Antibodies to HEK293 Cells

Human embryonic kidney (HEK293) cells, which do not express PAPP-A, were grown in Dulbecco's modified Eagle medium plus 10% fetal bovine serum at 37° C. and 5% $CO_2$ and suspended in FACS buffer (Dulbecco's phosphate buffered saline plus 10% fetal bovine serum) at $1.0\times10^6$ cells/mL and 100 μL was aliquoted per well into a 96 well round bottom polypropylene plates (Falcon®, Fisher Scientific, Waltham, MA, USA). After centrifugation and removing supernatant, a solution of each anti-PAPP-A monoclonal antibody at 100 μg/mL in FACS buffer was added at 100 μL/well, a volume sufficient to resuspend the HEK293 cells. Following incubation on ice for 30 minutes, HEK293 cells were washed with FACS buffer to remove free antibody. A secondary AffiniPure™ Goat Anti-Human IgG, Fcγ fragment specific APC (allophycocyanin) conjugated antibody (Jackson Immunoresearch, West Grove, PA, USA), was diluted to 2 μg/mL and 100 μL per well was added. After incubation on ice for 30 minutes, HEK293 cells were washed with FACS buffer to remove free antibody.

Flow Cytometry Analysis of HEK293 Cells

Flow cytometry of prepared cells was conducted using a BD FACSCanto™ Flow Cytometry system (Becton Dickinson, Franklin Lakes, NJ, USA). Live singlets were gated from the l/d discriminator and FSC(H)/FSC(A). Additions to the cell type cytometry profiles when incubated in the presence of the anti-PAPP-A antibodies were considered as binding.

Three of the anti-PAPP-A antibodies, Ab4, Ab5 and Ab6 non-specifically bound HEK293 cells, while neither Ab1, Ab2 nor Ab3 non-specifically bound HEK293 cells (Table W). The cause of this interaction is not well understood. However, the non-specific binding to HEK293 cells by Ab4, Ab5 and Ab6 excluded these antibodies from further development.

TABLE W

Non-specific binding of anti-PAPP-A monoclonal antibodies to HEK293 cells as assessed by flow cytometry

| Cell type | Ab1 | Ab2 | Ab3 | Ab4 | Ab5 | Ab6 |
|---|---|---|---|---|---|---|
| HEK293 | − | − | − | + | + | + |

−: Similar profile to isotype
+: Binding at 100 μg/mL

Example 6. Antibody Stability Under Thermal Stress

The antibodies Ab1, Ab2 and Ab3 were subjected to elevated temperature in an accelerated stability study at high concentration over time. To assess accelerated stability, antibody samples were subjected to storage at 40° C. Samples of Ab1, Ab2 and Ab3 were dissolved at concentrations up to 100 mg/mL in 15 mM histidine, pH 6.0, and stored at elevated temperature for up to three weeks. Samples were subsequently stored at −80° C. until analysis by size exclusion chromatography (SEC). SEC was performed using an Agilent 1260 Infinity II HPLC system equipped with a diode array UV detector (Agilent Technologies, Palo Alto, CA, USA). The data was analysed using Agilent ChemStation software. The following chromatographic conditions were used in the analysis: Column: Waters™ Acquity UPLC Protein BEH SEC column (200 Å, 1.7 μm, 4.6×300 mm; Milford, MA, USA); run at ambient temperature with a flow rate of 0.3 mL/minute and an injection volume of 5 μL; mobile phase 100 mM disodium phosphate, 100 mM disodium sulphate, 1 mM sodium azide, pH 6.8; detection at 214 nm and a 15 minute run time.

Figure 2:
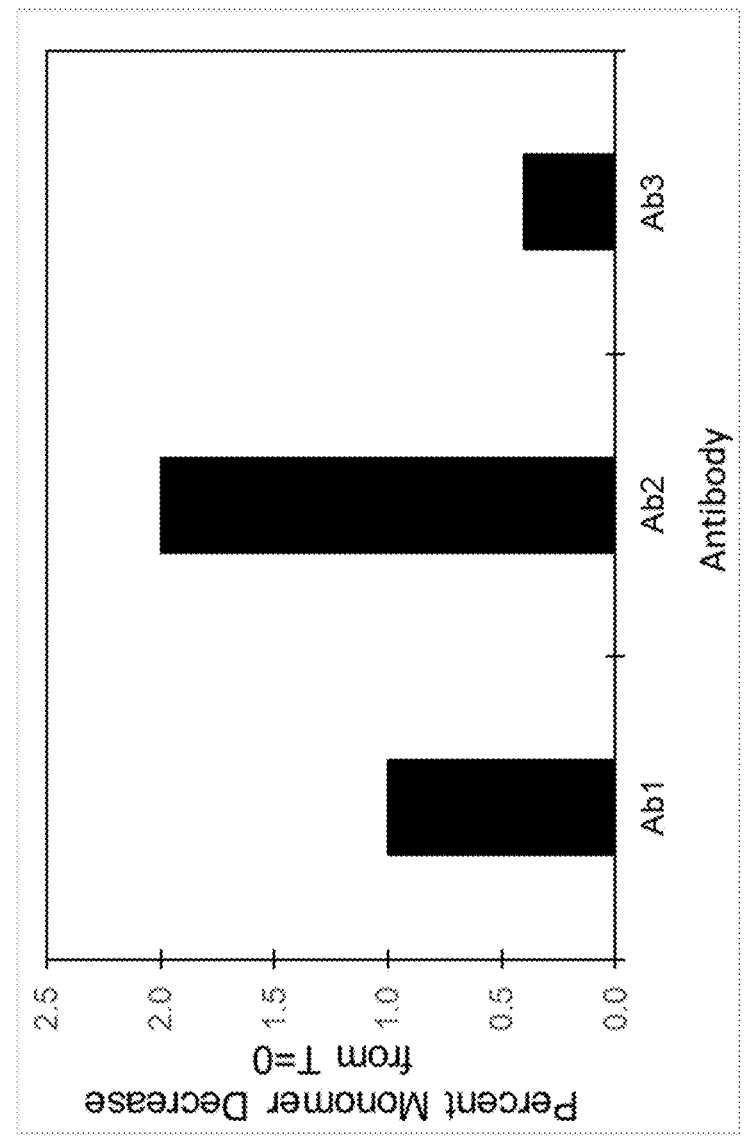
FIG. 2. Stability analysis of Ab1, Ab2, and Ab3 at elevated temperature. A decrease of percent monomers was observed following three weeks storage at 40° C.

The data for the analysed antibody monomers is shown in FIG. 2. A larger decrease in percent monomer was observed with Ab2, after incubation at 40° C. for three weeks as compared to Ab1 or Ab3. The reduced stability of Ab2 compared to Ab1 and Ab3 led to a decision not to select Ab2 as a clinical candidate.

Example 7. Liability Analysis

Forced degradation studies including heat, acid, base, broad spectrum Ultraviolet-Visible light stress, and chemical oxidation conditions were performed to detect sequence liabilities. A forced degradation multi-attribute method LC-MS automated workflow monitored changes and confirmed the trends of peptide level post-translational modifications indicative of critical quality attribute changes due to modifications such as: deamidation, oxidation, isomerization, and other peptide-level resolution chemical modifications.

Sample antibodies were prepared at 2.5 mg/mL in 25 mM phosphate buffer, pH 5.8. Heat stress was performed for one and three weeks at 40° C. and pH 9 stress was performed for 7 days. The peptides were separated using a Waters™ Acquity BEH C18 column (300 Å, 1.7 μm, 2.1 mm×150 mm). A complex gradient of increasing acetonitrile (0-60%) was applied over a period of 28 minutes at 55° C. with mobile phases containing 0.08% formic acid and 0.02% trifluoroacetic acid. A MaXis II TOF mass spectrometer (Bruker, Billerica, MA, USA) instrument was used for analysis of the peptides. Post-translational modifications of the samples were detected and quantified using Protein Metrics Byonic™ and Byologic® software (Protein Metrics/Dotmatics, San Diego, CA, USA). A broad search of all potential methionine oxidation, asparagine deamidation and succinimide formation was performed. All positive identified peptides were verified via tandem mass spectrometry fragmentation patterns, and XIC evaluated for proper retention time behaviour and window boundaries. Peptide level systematic analysis following thermal forced degradation stress depicted that there was a high level of oxidation only in Ab3. In Ab3, elevated levels of methionine (M102) oxidation in CDR3 of the heavy chain were noted. Methionine oxidation is a common post translational modification (PTM) that can impact the bioactivity of the antibody and potentially induce an immunogenic response. In neither Ab1 nor Ab2, was methionine residue oxidation observed. This data is consistent with reduced thermal stability of Ab3 and led to a decision not to continue with Ab3 as a clinical candidate.

In summary, testing of monoclonal antibodies Ab1, Ab2, and Ab3 under heat stress resulted in a determination of which antibody is suitable for further development. Only Ab1 did not show either decreased stability or protein sequence liability under enforced degradation conditions. This developability risk assessment data was consistent with selecting Ab1 as a clinical candidate and advancement into development. To conduct mouse in vivo studies, a mouse chimeric version of Ab1 was generated. This antibody, Ab7, comprised the variable domains identical to those of Ab1 (amino acids 1-123 for the heavy chain and amino acids 1-107 for the light chain) and mouse antibody constant regions (immunoglobulin heavy constant gamma 1 for the heavy chain and immunoglobulin kappa constant for the light chain).

Example 8. Efficacy of Anti-PAPP-A (Ab7) in pcy Mice

The objective of this study was to evaluate the therapeutic efficacy of the anti-PAPP-A (Ab7) antibody in reducing total kidney volume increase and ameliorating renal dysfunction in mice, using a non-orthologous model of ADPKD (autosomal dominant polycystic kidney disease) that carries a mutation in Nph3, a nephronophthisis gene causing renal cyst development and expansion that can be observed as early as 3 weeks of age.

Experimental Conditions

Mice (pcy) were treated either with Ab7 (anti-PAPP-A) at 10 mg/kg, IP injection, once a week, n=20) or Ab8 (isotype control antibody at 10 mg/kg, IP injection, once a week, n=22), starting at approximately 12 weeks of age and were dosed for approximately 22 weeks. Antibodies were dissolved before use in phosphate buffered saline and administered in a 10 mL/kg volume of administration.

Total kidney volume (TKV) was measured by magnetic resonance imaging (MRI) at baseline (before starting treatment), after 12 and 21 weeks of treatment. TKV, provided a metric of disease progression that was used to assess the efficacy of therapeutic regimens for ADPKD. In this study, the T2 weighted (T2W) MRI sequence was used for measuring the TKV. In-vivo MRI was performed on a 4.7 Tesla PharmaScan 47/16 system (Bruker, Billerica, MA, USA) with 38 mm $^1$H linear volume coil as transmitter-receiver. Mice were anesthetized with isoflurane (2-2.5%) in an oxygen-air mixture (1:1 ratio). T2-weighted (2D multi-slices Turbo SpinEcho RARE, TR/TE=2500/48 milliseconds; RARE Factor=8, Averages=15) images were acquired at 0.2×0.2 mm$^2$ in-plane, 0.8 mm slice thickness, 17-21 slices to cover the whole kidney volume. Image segmentation was performed manually by iterating through all the slices of an image volume and drawing a contour at the kidney boundary using the segment editor module in 3D slicer. The result of image segmentation was used for calculating the TKV by the following equation:

number of segmented voxels×size of voxel

TKVs were estimated longitudinally at baseline, 12 and 21 weeks of treatment (corresponding to 12-, 24- and 33-weeks old mice, respectively).

Glomerular filtration rate (GFR), a marker of kidney function, was determined by monitoring the transdermal GFR (t-GFR) using the FITC-sinistrin clearance method (MediBeacon®) at baseline (before starting treatment), after 12 and 18 weeks of treatment. Animals were shaved to remove the fur from the dorsal side (from top of the hind legs up to the neck, and across the ribs). A thin layer of depilation cream (Nair™) was applied to the shaved area and washed off after 2 minutes with warm water. For t-GFR device implantation, mice were anesthetized using isoflurane (induction 3% and maintenance 1.5%). The shaved area was cleaned using 70% ethanol and the t-GFR device was placed over the ribs and secured with silk tape (Cardinal Health, Dublin, OH, USA). A single intravenous injection (0.15 mg/gram body weight) of FITC-sinistrin (MediBeacon®, St Louis, MO, USA) was given retro-orbitally (5 µL/gram body weight) using a 0.5 mL insulin syringe. The injected mice recovered in the cage and data was recorded for 1.0-1.5 hours. The clearance of fluorescent labelled sinistrin recorded on the t-GFR device was analyzed by MediBeacon® studio 2 software. The software employed a 3-D compartment modelling technique to compute half-life of FITC-sinistrin, which was used to calculate GFR.

Effect of Anti-PAPP-A (Ab7) or Isotype Control (Ab8) on Kidney Size and Function of pcy Mice In this study, the ability of anti-PAPP-A (Ab7) to reduce total kidney volume increase and amelioration of renal function decline was assessed in the pcy mouse model of ADPKD. Total kidney volume was measured using MRI at baseline, 12 and 21 weeks of treatment (corresponding to 12-, 24- and 33-week old mice, respectively).

Figure 3:
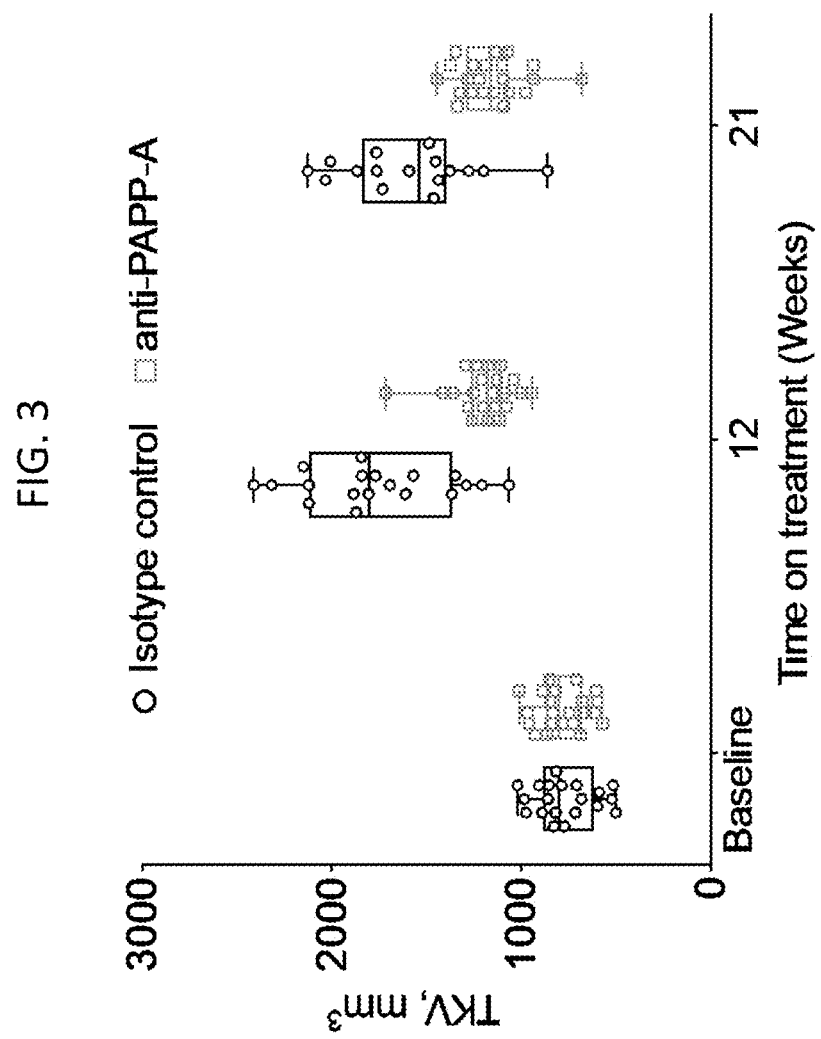
FIG. 3. Total Kidney volume (TKV) of pcy mice treated with Ab8 (isotype control) or Ab7 (anti-PAPP-A). TKV was estimated by MRI at baseline, 12 and 21 weeks of treatment. pcy mice were treated with 10 mg/kg of either Ab8 (isotype control, black circles) or Ab7 (anti-PAPP-A, grey squares). Data presented as box plots.

As shown in FIG. 3, average TKV increased in Ab8 (isotype control)-treated pcy mice from baseline to 12 weeks (769 mm$^3$ vs. 1753 mm$^3$, respectively) and plateaued at 21 weeks of treatment (1591 mm$^3$). These data indicated a significant increase in the TKV of the Ab8 (isotype control)-treated mice. Anti-PAPP-A (Ab7)-treatment reduced TKV increase both at 12 and 21 weeks of treatment (1200 mm$^3$ and 1159 mm$^3$, respectively) compared to isotype control (Ab8)-treated pcy mice. Compared to the Ab8 (isotype control) group, and adjusted for body weight, the mean TKV increase from baseline for the Ab7 (anti-PAPP-A)-treated group was reduced by an estimated average of 482 mm$^3$ and 461 mm$^3$, at 12 and 21 weeks of treatment, respectively. These data indicated a significant suppression of TKV increase from Ab7 (anti-PAPP-A)-treatment (Table R).

TABLE R

Estimated mean TKV (mm$^3$) changes from baseline in the anti-PAPP-A (Ab7) group, compared to isotype control (Ab8) in pcy mice (adjusted for body weight).

| Treatment duration | Ab8, isotype control (mm$^3$) | Ab7, anti-PAPP-A (mm$^3$) | Ab7 vs Ab8 (mm$^3$) | p-value |
|---|---|---|---|---|
| 12 weeks | 852 | 370 | −482 | <0.0001 |
| 21 weeks | 904 | 443 | −461 | <0.0001 |

Figure 4:
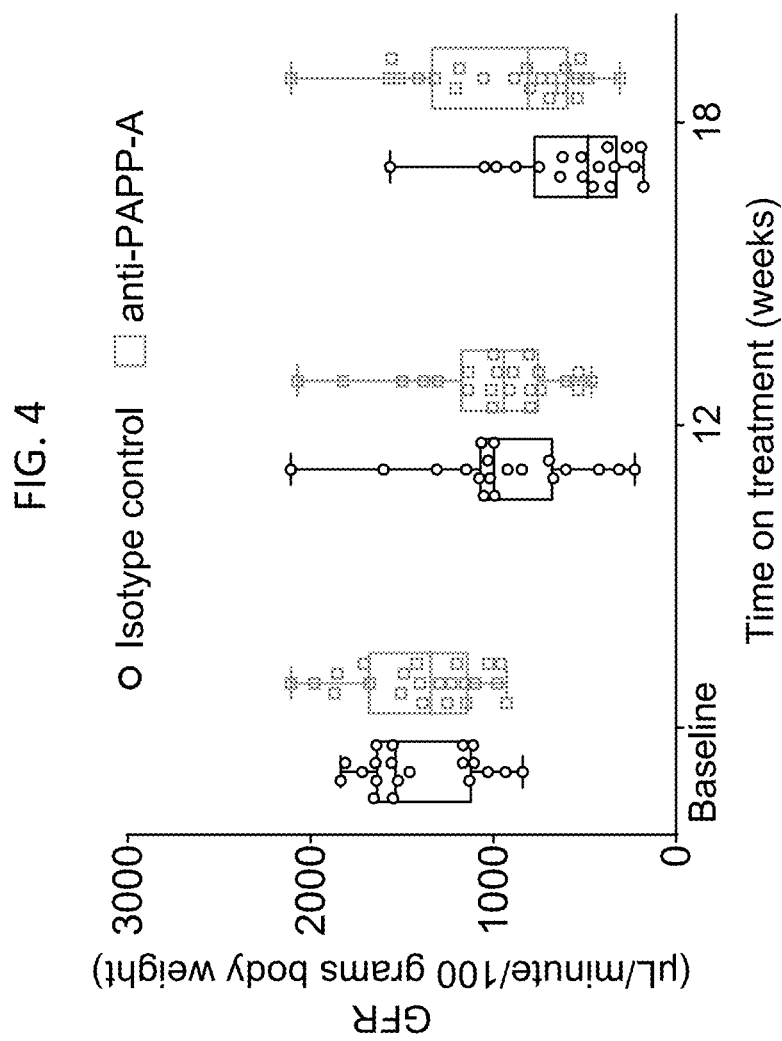
FIG. 4. Glomerular filtration rate (GFR) of pcy mice treated with Ab8 (isotype control) or Ab7 (anti-PAPP-A). Kidney function (GFR) was evaluated at baseline, 12 and 18 weeks of treatment using the FITC-sinistrin method (MediBeacon®). pcy mice were treated with 10 mg/kg of either Ab8 (isotype control, black circles) or Ab7 (anti-PAPP-A, grey squares). Data presented as box plots.

Kidney function, as measured by the t-GFR method, was evaluated at baseline, 12 and 18 weeks of treatment. At baseline, the average GFR was at similar levels for mice that were allocated to either Ab8 (isotype control)- or Ab7 (anti-PAPP-A)-treated groups: 1404 µL/minute/100 grams of body weight and 1395 µL/minute/100 grams body weight, respectively (FIG. 4). At 12 weeks of treatment, the average GFR of the Ab8 (isotype control) group was 953 µL/minute/100 grams body weight, while for the Ab7 (anti-PAPP-A) group was 1009 µL/minute/100 grams body weight. At 18 weeks of treatment, the average GFR of the Ab8 (isotype control) group declined to 574 µL/minute/100 grams body weight while for the Ab7 (anti-PAPP-A) group it was 963 µL/minute/100 grams body weight (FIG. 4). Compared to the isotype control group, the GFR decline from baseline for the Ab7-treated group was reduced by an estimated average of 399 µL/minute/100 grams body weight at 18 weeks of treatment, indicating a significant suppression of kidney function decline from the Ab7 (anti-PAPP-A) treatment (Table S).

TABLE S

Estimated mean GFR (μL/minute 100 grams body weight) changes from baseline in the anti-PAPP-A (Ab7) group, compared to isotype control (Ab8) in pcy mice.

| Treatment duration | Ab8, Isotype control, μL/minute 100 grams body weight | Ab7, anti-PAPP-A, μL/minute 100 grams body weight | Ab7 vs Ab 8, μL/minute 100 grams body weight | p-value |
|---|---|---|---|---|
| 18 | 433 | 832 | 399 | <0.0043 |

Example 9: Administration of PAPP-A Antibodies to Humans

An anti-PAPP-A antibody described herein is administered intravenously (IV) or subcutaneously (SC) to a human subject. The dosing regimen is as follows:
Group 1: Anti-PAPP-A antibody single dose on Day 1—30 mg IV infusion
Group 2: Anti-PAPP-A antibody single dose on Day 1—up to 100 mg IV infusion
Group 3: Anti-PAPP-A antibody single dose on Day 1—up to 100 mg SC injection
Group 4: Anti-PAPP-A antibody single dose on Day 1—up to 300 mg IV infusion
Group 5: Anti-PAPP-A antibody single dose on Day 1—up to 300 mg SC injection
Group 6: Anti-PAPP-A antibody single dose on Day 1—up to 900 mg IV infusion The anti-PAPP-A antibody can also be administered every two weeks for up to four doses by either SC or IV or as a single dose by either SC or IV.

The antibody is observed to be safe and tolerated by the subjects after administration.

Heavy Chain and Light Chain Antibody Sequences

The heavy (HC) and light chain (LC) amino acid sequences of the eight monoclonal antibodies from above: Ab1, Ab2, Ab3, Ab4, Ab5, Ab6, Ab7, and Ab8 are described below in Tables A-H. The first six anti-PAPP-A antibodies have the same heavy chain and light chain constant regions, while Ab7, also an anti-PAPP-A antibody, has murine-compatible constant regions. For Ab1-Ab6, the variable regions for both the heavy (VH) and variable light (VL) chains differ, particular for the complementarity-determining regions (CDRs). The CDRs were determined using Kabat nomenclature, with each of the CDRs shown by bold text and underline (CDR1, CDR2, and CDR3, respectively) in each variable region sequence. The CDRs are also listed separately in the tables. Consensus sequences of the CDRs based on Ab1 to Ab6 are provided in Table I.

To conduct mouse in vivo studies, a mouse chimeric version of Ab1 was generated and characterized. This antibody, Ab7, is comprised of the variable domains identical to those of Ab1 (amino acids 1-123 for the heavy chain and amino acids 1-107 for the light chain) and mouse antibody constant regions (immunoglobulin heavy constant gamma 1 for the heavy chain and immunoglobulin kappa constant for the light chain). Ab7 exhibited similar binding affinity of the PAPP-A substrate as Ab1, as demonstrated by SPD (see Example 2). An isotype control antibody (Ab8) was used in all in vivo studies. Ab8 is an anti-tetanus toxoid antibody with mouse immunoglobulin heavy constant gamma 1 and mouse immunoglobulin kappa constant. The sequences of these two antibodies are listed in Tables G and H.

TABLE A

Heavy and light chain amino acid sequences of anti-PAPP-A antibody 1 (Ab1)

| SEQ ID NO: | Clone Name | Antibody Region | Residue | Sequence |
|---|---|---|---|---|
| 1 | Ab1 | Heavy Chain | | EVQLVESGGGVVQPGRSLRLSCAASGFTFSSYAM HWVRQAPGKGLEWVAVISYDGSIKYYADAVKGRF TISRDNSKNTLYLQMNSLRAEDTAVYYCARHNRI YSWGWHTFDIWGQGTLVTVSSASTKGPSVFPLAP SSKSTSGGTAALGCLVKDYFPEPVTVSWNSGALT SGVHTFPAVLQSSGLYSLSSVVTVPSSSLGTQTY ICNVNHKPSNTKVDKKVEPKSCDKTHTCPPCPAP EAAGGPSVFLFPPKPKDTLMISRTPEVTCVVVDV SHEDPEVKFNWYVDGVEVHNAKTKPREEQYNSTY RVVSVLTVLHQDWLNGKEYKCKVSNKALPAPIEK TISKAKGQPREPQVYTLPPSREEMTKNQVSLTCL VKGFYPSDIAVEWESNGQPENNYKTTPPVLDSDG SFFLYSKLTVDKSRWQQGNVFSCSVMHEALHNHY TQKSLSLSPGK |
| 2 | Ab1 | Variable heavy chain domain | | EVQLVESGGGVVQPGRSLRLSCAASGFTFSSYAM HWVRQAPGKGLEWVAVISYDGSIKYYADAVKGRF TISRDNSKNTLYLQMNSLRAEDTAVYYCARHNRI YSWGWHTFDIWGQGTLVTVSS |
| 3 | Ab1 | VH CDR-H1 | Residues 31-35 of SEQ ID NO: 2 | SYAMH |
| 4 | Ab1 | VH CDR-H2 | Residues 50-66 of SEQ ID NO: 2 | VISYDGSIKYYADAVKG |
| 5 | Ab1 | VH CDR-H3 | Residues 99-112 of SEQ ID NO: 2 | HNRIYSWGWHTFDI |

TABLE A-continued

Heavy and light chain amino acid sequences of anti-PAPP-A antibody 1 (Ab1)

| SEQ ID NO: | Clone Name | Antibody Region | Residue | Sequence |
|---|---|---|---|---|
| 6 | Ab1 | Light Chain | | DIQMTQSPSSLSASVGDRVTITCRASQDISIYLN WYQQKPGKAPKLLIYGASSLQSGVPSRFSGSGSG TDFTLTISSLQPEDFATYYCQQADAGPWKFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 7 | Ab1 | Variable light chain domain | | DIQMTQSPSSLSASVGDRVTITCRASQDISIYLN WYQQKPGKAPKLLIYGASSLQSGVPSRFSGSGSG TDFTLTISSLQPEDFATYYCQQADAGPWKFGGGT KVEIK |
| 8 | Ab1 | VL CDR-L1 | Residues 24-34 of SEQ ID NO: 7 | RASQDISIYLN |
| 9 | Ab1 | VL CDR-L2 | Residues 50-56 of SEQ ID NO: 7 | GASSLQS |
| 10 | Ab1 | VL CDR-L3 | Residues 89-97 of SEQ ID NO: 7 | QQADAGPWK |

TABLE B

Heavy and light chain amino acid sequences of anti-PAPP-A antibody 2 (Ab2)

| SEQ ID NO: | Clone Name | Antibody Region | Residue | Sequence |
|---|---|---|---|---|
| 11 | Ab2 | Heavy Chain | | EVQLVESGGGVVQPGRSLRLSCAASGFTFSSYAM HWVRQAPGKGLEWVAVISYDGSIKYYADAVKGRF TISRDNSKNTLYLQMNSLRAEDTAVYYCARHERI PPWGFHTFDIWGQGTLVTVSSASTKGPSVFPLAP SSKSTSGGTAALGCLVKDYFPEPVTVSWNSGALT SGVHTFPAVLQSSGLYSLSSVVTVPSSSLGTQTY ICNVNHKPSNTKVDKKVEPKSCDKTHTCPPCPAP EAAGGPSVFLFPPKPKDTLMISRTPEVTCVVVDV SHEDPEVKFNWYVDGVEVHNAKTKPREEQYNSTY RVVSVLTVLHQDWLNGKEYKCKVSNKALPAPIEK TISKAKGQPREPQVYTLPPSREEMTKNQVSLTCL VKGFYPSDIAVEWESNGQPENNYKTTPPVLDSDG SFFLYSKLTVDKSRWQQGNVFSCSVMHEALHNHY TQKSLSLSPGK |
| 12 | Ab2 | Variable heavy chain domain | | EVQLVESGGGVVQPGRSLRLSCAASGFTFSSYAM HWVRQAPGKGLEWVAVISYDGSIKYYADAVKGRF TISRDNSKNTLYLQMNSLRAEDTAVYYCARHERI PPWGFHTFDIWGQGTLVTVSS |
| 13 | Ab2 | VH CDR-H1 | Residues 31-35 of SEQ ID NO: 12 | SYAMH |
| 14 | Ab2 | VH CDR-H2 | Residues 50-66 of SEQ ID NO: 12 | VISYDGSIKYYADAVKG |
| 15 | Ab2 | VH CDR-H3 | Residues 99-112 of SEQ ID NO: 12 | HERIPPWGFHTFDI |
| 16 | Ab2 | Light Chain | | DIQMTQSPSSLSASVGDRVTITCRASQGISIYLN WYQQKPGKAPKLLIYGASSLQSGVPSRFSGSGSG TDFTLTISSLQPEDFATYYCQQSDGTPWTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE B-continued

Heavy and light chain amino acid sequences of anti-PAPP-A antibody 2 (Ab2)

| SEQ ID NO: | Clone Name | Antibody Region | Residue | Sequence |
|---|---|---|---|---|
| 17 | Ab2 | Variable light chain domain | | DIQMTQSPSSLSASVGDRVTITCRASQGISIYLN WYQQKPGKAPKLLIYGASSLQSGVPSRFSGSGSG TDFTLTISSLQPEDFATYYCQQSDGTPWTFGGGT KVEIK |
| 18 | Ab2 | VL CDR-L1 | Residues 24-34 of SEQ ID NO: 17 | RASQGISIYLN |
| 19 | Ab2 | VL CDR-L2 | Residues 50-56 of SEQ ID NO: 17 | GASSLQS |
| 20 | Ab2 | VL CDR-L3 | Residues 89-97 of SEQ ID NO: 17 | QQSDGTPWT |

TABLE C

Heavy and light chain amino acid sequences of anti-PAPP-A antibody 3 (Ab3)

| SEQ ID NO: | Clone Name | Antibody Region | Residue | Sequence |
|---|---|---|---|---|
| 21 | Ab3 | Heavy Chain | | EVQLVESGGGVVQPGRSLRLSCAASGFTFSSYGM HWVRQAPGKGLEWVAVISYDGRNKYYADAVKGRF TISRDNSKNTLYLQMNSLRAEDTAVYYCARYKPM PFDVWGQGTLVTVSSASTKGPSVFPLAPSSKSTS GGTAALGCLVKDYFPEPVTVSWNSGALTSGVHTF PAVLQSSGLYSLSSVVTVPSSSLGTQTYICNVNH KPSNTKVDKKVEPKSCDKTHTCPPCPAPEAAGGP SVFLFPPKPKDTLMISRTPEVTCVVVDVSHEDPE VKFNWYVDGVEVHNAKTKPREEQYNSTYRVVSVL TVLHQDWLNGKEYKCKVSNKALPAPIEKTISKAK GQPREPQVYTLPPSREEMTKNQVSLTCLVKGFYP SDIAVEWESNGQPENNYKTTPPVLDSDGSFFLYS KLTVDKSRWQQGNVFSCSVMHEALHNHYTQKSLS LSPGK |
| 22 | Ab3 | Variable heavy chain domain | | EVQLVESGGGVVQPGRSLRLSCAASGFTFSSYGM HWVRQAPGKGLEWVAVISYDGRNKYYADAVKGRF TISRDNSKNTLYLQMNSLRAEDTAVYYCARYKPM PFDVWGQGTLVTVSS |
| 23 | Ab3 | VH CDR-H1 | Residues 31-35 of SEQ ID NO: 22 | SYGMH |
| 24 | Ab3 | VH CDR-H2 | Residues 50-66 of SEQ ID NO: 22 | VISYDGRNKYYADAVKG |
| 25 | Ab3 | VH CDR-H3 | Residues 99-112 of SEQ ID NO: 22 | YKPMPFDV |
| 26 | Ab3 | Light Chain | | DIQMTQSPSSLSASVGDRVTITCRASQSISSYLN WYQQKPGKAPKLLIYEASILQSGVPSRFSGSGSG TDFTLTISSLQPEDFATYYCGQSYYTPFPFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 27 | Ab3 | Variable light chain domain | | DIQMTQSPSSLSASVGDRVTITCRASQSISSYLN WYQQKPGKAPKLLIYEASILQSGVPSRFSGSGSG TDFTLTISSLQPEDFATYYCGQSYYTPFPFGGGT KVEIK |
| 28 | Ab3 | VL CDR-L1 | Residues 24-34 of SEQ ID NO: 27 | RASQSISSYLN |

TABLE C-continued

Heavy and light chain amino acid sequences of anti-PAPP-A antibody 3 (Ab3)

| SEQ ID NO: | Clone Name | Antibody Region | Residue | Sequence |
|---|---|---|---|---|
| 29 | Ab3 | VL CDR-L2 | Residues 50-56 of SEQ ID NO: 27 | EASILQS |
| 30 | Ab3 | VL CDR-L3 | Residues 89-97 of SEQ ID NO: 27 | GQSYYTPFP |

TABLE D

Heavy and light chain amino acid sequences of anti-PAPP-A antibody 4 (Ab4)

| SEQ ID NO: | Clone Name | Antibody Region | Residue | Sequence |
|---|---|---|---|---|
| 31 | Ab4 | Heavy Chain | | EVQLVESGGGVVQPGRSLRLSCAASGFAFSTYGM HWVRQAPGKGLEWVAVIRYDGQEKYYADAVKGRF TISRDNSKNTLYLQMNSLRAEDTAVYYCARYKPM PFDVWGQGTLVTVSSASTKGPSVFPLAPSSKSTS GGTAALGCLVKDYFPEPVTVSWNSGALTSGVHTF PAVLQSSGLYSLSSVVTVPSSSLGTQTYICNVNH KPSNTKVDKKVEPKSCDKTHTCPPCPAPEAAGGP SVFLFPPKPKDTLMISRTPEVTCVVVDVSHEDPE VKFNWYVDGVEVHNAKTKPREEQYNSTYRVVSVL TVLHQDWLNGKEYKCKVSNKALPAPIEKTISKAK GQPREPQVYTLPPSREEMTKNQVSLTCLVKGFYP SDIAVEWESNGQPENNYKTTPPVLDSDGSFFLYS KLTVDKSRWQQGNVFSCSVMHEALHNHYTQKSLS LSPGK |
| 32 | Ab4 | Variable heavy chain domain | | EVQLVESGGGVVQPGRSLRLSCAASGFAFSTYGM HWVRQAPGKGLEWVAVIRYDGQEKYYADAVKGRF TISRDNSKNTLYLQMNSLRAEDTAVYYCARYKPM PFDVWGQGTLVTVSS |
| 33 | Ab4 | VH CDR-H1 | Residues 31-35 of SEQ ID NO: 32 | TYGMH |
| 34 | Ab4 | VH CDR-H2 | Residues 50-66 of SEQ ID NO: 32 | VIRYDGQEKYYADAVKG |
| 35 | Ab4 | VH CDR-H3 | Residues 99-112 of SEQ ID NO: 32 | YKPMPFDV |
| 36 | Ab4 | Light Chain | | DIQMTQSPSSLSASVGDRVTITCRASQSISRYLN WYQQKPGKAPKLLIYAASILQSGVPSRFSGSGSG TDFTLTISSLQPEDFATYYCQQSHPTPFTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 37 | Ab4 | Variable light chain domain | | DIQMTQSPSSLSASVGDRVTITCRASQSISRYLN WYQQKPGKAPKLLIYAASILQSGVPSRFSGSGSG TDFTLTISSLQPEDFATYYCQQSHPTPFTFGGGT KVEIK |
| 38 | Ab4 | VL CDR-L1 | Residues 24-34 of SEQ ID NO: 37 | RASQSISRYLN |
| 39 | Ab4 | VL CDR-L2 | Residues 50-56 of SEQ ID NO: 37 | AASILQS |
| 40 | Ab4 | VL CDR-L3 | Residues 89-97 of SEQ ID NO: 37 | QQSHPTPFT |

TABLE E

Heavy and light chain amino acid sequences of anti-PAPP-A antibody 5 (Ab5)

| SEQ ID NO: | Clone Name | Antibody Region | Residue | Sequence |
|---|---|---|---|---|
| 41 | Ab5 | Heavy Chain | | EVQLVESGGGVVQPGRSLRLSCAASGFTFSSYGMHW VRQAPGKGLEWVAVIYYDGRRKYYADSVKGRFTISR DNSKNTLYLQMNSLRAEDTAVYYCARADMHRFDVWG QGTLVTVSSASTKGPSVFPLAPSSKSTSGGTAALGC LVKDYFPEPVTVSWNSGALTSGVHTFPAVLQSSGLY SLSSVVTVPSSSLGTQTYICNVNHKPSNTKVDKKVE PKSCDKTHTCPPCPAPEAAGGPSVFLFPPKPKDTLM ISRTPEVTCVVVDVSHEDPEVKFNWYVDGVEVHNAK TKPREEQYNSTYRVVSVLTVLHQDWLNGKEYKCKVS NKALPAPIEKTISKAKGQPREPQVYTLPPSREEMTK NQVSLTCLVKGFYPSDIAVEWESNGQPENNYKTTPP VLDSDGSFFLYSKLTVDKSRWQQGNVFSCSVMHEAL HNHYTQKSLSLSPGK |
| 42 | Ab5 | Variable heavy chain domain | | EVQLVESGGGVVQPGRSLRLSCAASGFTFSSYGMHW VRQAPGKGLEWVAVIYYDGRRKYYADSVKGRFTISR DNSKNTLYLQMNSLRAEDTAVYYCARADMHRFDVWG QGTLVTVSS |
| 43 | Ab5 | VH CDR-H1 | Residues 31-35 of SEQ ID NO: 42 | SYGMH |
| 44 | Ab5 | VH CDR-H2 | Residues 50-66 of SEQ ID NO: 42 | VIYYDGRRKYYADSVKG |
| 45 | Ab5 | VH CDR-H3 | Residues 99-112 of SEQ ID NO: 42 | ADMHRFDV |
| 46 | Ab5 | Light Chain | | DIQMTQSPSSLSASVGDRVTITCRASQDIISYLNWY QQKPGKAPKLLIYVASSLQSGVPSRFSGSGSGTDFT LTISSLQPEDFATYYCQQSYSPPYTFGGGTKVEIKR TVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC |
| 47 | Ab5 | Variable light chain domain | | DIQMTQSPSSLSASVGDRVTITCRASQDIISYLNWY QQKPGKAPKLLIYVASSLQSGVPSRFSGSGSGTDFT LTISSLQPEDFATYYCQQSYSPPYTFGGGTKVEIK |
| 48 | Ab5 | VL CDR-L1 | Residues 24-34 of SEQ ID NO: 47 | RASQDIISYLN |
| 49 | Ab5 | VL CDR-L2 | Residues 50-56 of SEQ ID NO: 47 | VASSLQS |
| 50 | Ab5 | VL CDR-L3 | Residues 89-97 of SEQ ID NO: 47 | QQSYSPPYT |

TABLE F

Heavy and light chain amino acid sequences of anti-PAPP-A antibody 6 (Ab6)

| SEQ ID NO: | Clone Name | Antibody Region | Residue | Sequence |
|---|---|---|---|---|
| 51 | Ab6 | Heavy Chain | | EVQLLESGGGLVQPGGSLRLSCAASGFTFSSYAMSW VRQAPGKGLEWVSAISMTVGRTYYADSVKGRFTISR DNSKNTLYLQMNSLRAEDTAVYYCARVWGGVRFDVW GQGTLVTVSSASTKGPSVFPLAPSSKSTSGGTAALG CLVKDYFPEPVTVSWNSGALTSGVHTFPAVLQSSGL YSLSSVVTVPSSSLGTQTYICNVNHKPSNTKVDKKV EPKSCDKTHTCPPCPAPEAAGGPSVFLFPPKPKDTL |

TABLE F-continued

Heavy and light chain amino acid sequences of anti-PAPP-A antibody 6 (Ab6)

| SEQ ID NO: | Clone Name | Antibody Region | Residue | Sequence |
|---|---|---|---|---|
| | | | | MISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 52 | Ab6 | Variable heavy chain domain | | EVQLLESGGGLVQPGGSLRLSCAASGFTFSSYAMSWVRQAPGKGLEWVSAISMTVGRTYYADSVKGRFTISRDNSKNTLYLQMNSLRAEDTAVYYCARVWGGVRFDVWGQGTLVTVSS |
| 53 | Ab6 | VH CDR-H1 | Residues 31-35 of SEQ ID NO: 52 | SYAMS |
| 54 | Ab6 | VH CDR-H2 | Residues 50-66 of SEQ ID NO: 52 | AISMTVGRTYYADSVKG |
| 55 | Ab6 | VH CDR-H3 | Residues 99-112 of SEQ ID NO: 52 | VWGGVRFDV |
| 56 | Ab6 | Light Chain | | DIQMTQSPSSLSASVGDRVTITCRASQSISTYLNWYQQKPGKAPKLLIYVASILQSGVPSRFSGSGSGTDFTLTISSLQPEDFATYYCQQSSSTPWTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 57 | Ab6 | Variable light chain domain | | DIQMTQSPSSLSASVGDRVTITCRASQSISTYLNWYQQKPGKAPKLLIYVASILQSGVPSRFSGSGSGTDFTLTISSLQPEDFATYYCQQSSSTPWTFGGGTKVEIK |
| 58 | Ab6 | VL CDR-L1 | Residues 24-34 of SEQ ID NO: 57 | RASQSISTYLN |
| 59 | Ab6 | VL CDR-L2 | Residues 50-56 of SEQ ID NO: 57 | VASILQS |
| 60 | Ab6 | VL CDR-L3 | Residues 89-97 of SEQ ID NO: 57 | QQSSSTPWT |

TABLE G

Heavy and light chain amino acid sequences of anti-PAPP-A antibody 7 (Ab7)

| SEQ ID NO: | Clone Name | Antibody Region | Residue | Sequence |
|---|---|---|---|---|
| 61 | Ab7 | Heavy Chain | | EVQLVESGGGVVQPGRSLRLSCAASGFTFSSYAMHWVRQAPGKGLEWVAVISYDGSIKYYADAVKGRFTISRDNSKNTLYLQMNSLRAEDTAVYYCARHNRIYSWGWHTFDIWGQGTLVTVSSAKTTPPSVYPLAPGSAAQTNSMVTLGCLVKGYFPEPVTVTWNSGSLSSGVHTFPAVLQSDLYTLSSSVTVPSSTWPSQTVTCNVAHPASSTKVDKKIVPRDCGCKPCICTVPEVSSVFIFPPKPKDVLTITLTPKVTCVVVDISKDDPEVQFSWFVDDVEVHTAQTKPREEQINSTFRSVSELPIMHQDWLNGKEFKCRVNSAAFPAPIEKTISKTKGRPKAPQVYTIPPPKEQMAKDKVSLTCMITNFFPEDITVEWQWNGQPAENYKNTQPIMDTDGSYFVYSKLNVQKSNWEAGNTFTCSVLHEGLHNHHTEKSLSHSPGK |

TABLE G-continued

Heavy and light chain amino acid sequences of anti-PAPP-A antibody 7 (Ab7)

| SEQ ID NO: | Clone Name | Antibody Region | Residue | Sequence |
|---|---|---|---|---|
| 62 | Ab7 | Variable heavy chain domain | | EVQLVESGGGVVQPGRSLRLSCAASGFTFSSYAMHW VRQAPGKGLEWVAVISYDGSIKYYADAVKGRFTISR DNSKNTLYLQMNSLRAEDTAVYYCARHNRIYSWGWH TFDIWGQGTLVTVSS |
| 63 | Ab | VH CDR-H1 | Residues 31-35 of SEQ ID NO: 62 | SYAMH |
| 64 | Ab7 | VH CDR-H2 | Residues 50-66 of SEQ ID NO: 62 | VISYDGSIKYYADAVKG |
| 65 | Ab7 | VH CDR-H3 | Residues 99-112 of SEQ ID NO: 62 | HNRIYSWGWHTFDI |
| 66 | Ab7 | Light Chain | | DIQMTQSPSSLSASVGDRVTITCRASQDISIYLNWY QQKPGKAPKLLIYGASSLQSGVPSRFSGSGSGTDFT LTISSLQPEDFATYYCQQADAGPWKFGGGTKVEIKR ADAAPTVSIFPPSSEQLTSGGASVVCFLNNFYPKDI NVKWKIDGSERQNGVLNSWTDQDSKDSTYSMSSTLT LTKDEYERHNSYTCEATHKTSTSPIVKSFNRNEC |
| 67 | Ab7 | Variable light chain domain | | DIQMTQSPSSLSASVGDRVTITCRASQDISIYLNWY QQKPGKAPKLLIYGASSLQSGVPSRFSGSGSGTDFT LTISSLQPEDFATYYCQQADAGPWKFGGGTKVEIK |
| 68 | Ab7 | VL CDR-L1 | Residues 24-34 of SEQ ID NO: 67 | RASQDISIYLN |
| 69 | Ab7 | VL CDR-L2 | Residues 50-56 of SEQ ID NO: 67 | GASSLQS |
| 70 | Ab7 | VL CDR-L3 | Residues 89-97 of SEQ ID NO: 67 | QQADAGPWK |

TABLE H

Heavy and light chain amino acid sequences of isotype control antibody 8 (Ab8)

| SEQ ID NO: | Clone Name | Antibody Region | Residue | Sequence |
|---|---|---|---|---|
| 71 | Ab8 | Heavy Chain | | EVQLLESGGDLVRPGGSLRLSCAASGFSFSRYGMSW VRQAPGKGLDWVAHISASAGATYYADSVKGRFTISR DNSKNTLFLQMNNLRADDTAIYYCAKGGKQWLIPWF DPWGQGTLVTVSSAKTTPPSVYPLAPGSAAQTNSMV TLGCLVKGYFPEPVTVTWNSGSLSSGVHTFPAVLQS DLYTLSSSVTVPSSTWPSETVTCNVAHPASSTKVDK KIVPRDCGCKPCICTVPEVSSVFIFPPKPKDVLTIT LTPKVTCVVVDISKDDPEVQFSWFVDDVEVHTAQTQ PREEQFNSTFRSVSELPIMHQDWLNGKEFKCRVNSA AFPAPIEKTISKTKGRPKAPQVYTIPPPKEQMAKDK VSLTCMITDFFPEDITVEWQWNGQPAENYKNTQPIM DTDGSYFVYSKLNVQKSNWEAGNTFTCSVLHEGLHN HHTEKSLSHSPGK |
| 72 | Ab8 | Light Chain | | DIQMTQSPSSVSASVGDRVTIACRASQDISDRLAWY QQKPGKVPKVLIYGASSLQSGVPSRFSGSGSGTDFT LTINSLQPEDFATYYCQQANSFPLTFGGGTKVEMKR ADAAPTVSIFPPSSEQLTSGGASVVCFLNNFYPKDI NVKWKIDGSERQNGVLNSWTDQDSKDSTYSMSSTLT LTKDEYERHNSYTCEATHKTSTSPIVKSFNRNEC |

TABLE I

Consensus Sequences and PAPP-A protein sequence

| SEQ ID NO | Antibody Region | Sequence |
|---|---|---|
| 73 (ST.26 sequence listing skipped sequence) | CDR H1 consensus | XYXMX |
| 74 | CDR H2 consensus | XIXXXXXXXYYADXVKG |
| 75 | CDR H3 consensus | HXRIXXWGXHTFDI |
| 76 | CDR L1 consensus | RASQXIXXYLN |
| 77 | CDR L2 consensus | XASXLQS |
| 78 (ST.26 sequence listing skipped sequence) | CDR L3 consensus | XQXXXXPXX |
| 79 | PAPP-A amino acid sequence UniProt Q13219 | MRLWSWVLHLGLLSAALGCGLAERPRRARRDPRAGRPPRPAAGPATCATRA ARGRRASPPPPPPPPGGAWEAVRVPRRRQQREARGATEEPSPPSRALYFSGR GEQLRLRADLELPRDAFTLQVWLRAEGGQRSPAVITGLYDKCSYISRDRGW VVGIHTISDQDNKDPRYFFSLKTDRARQVTTINAHRSYLPGQWVYLAATYD GQFMKLYVNGAQVATSGEQVGGIFSPLTQKCKVLMLGGSALNHNYRGYIEH FSLWKVARTQREILSDMETHGAHTALPQLLLQENWDNVKHAWSPMKDGSSP KVEFSNAHGFLLDTSLEPPLCGQTLCDNTEVIASYNQLSSFRQPKVVRYRV VNLYEDDHKNPTVTREQVDFQHHQLAEAFKQYNISWELDVLEVSNSSLRRR LILANCDISKIGDENCDPECNHTLTGHDGGDCRHLRHPAFVKKQHNGVCDM DCNYERFNFDGGECCDPEITNVTQTCFDPDSPHRAYLDVNELKNILKLDGS THLNIFFAKSSEEELAGVATWPWDKEALMHLGGIVLNPSFYGMPGHTHTMI HEIGHSLGLYHVFRGISEIQSCSDPCMETEPSFETGDLCNDTNPAPKHKSC GDPGPGNDTCGFHSFFNTPYNNFMSYADDDCTDSFTPNQVARMHCYLDLVY QGWQPSRKPAPVALAPQVLGHTTDSVTLEWFPPIDGHFFERELGSACHLCL EGRILVQYASNASSPMPCSPSGHWSPREAEGHPDVEQPCKSSVRTWSPNSA VNPHTVPPACPEPQGCYLELEFLYPLVPESLTIWVTFVSTDWDSSGAVNDI KLLAVSGKNISLGPQNVFCDVPLTIRLWDVGEEVYGIQIYTLDEHLEIDAA MLTSTADTPLCLQCKPLKYKVVRDPPLQMDVASILHLNRKFVDMDLNLGSV YQYWVITISGTEESEPSPAVTYIHGSGYCGDGIIQKDQGEQCDDMNKINGD GCSLFCRQEVSFNCIDEPSRCYFHDGDGVCEEFEQKTSIKDCGVYTPQGFL DQWASNASVSHQDQQCPGWVIIGQPAASQVCRTKVIDLSEGISQHAWYPCT ISYPYSQLAQTTFWLRAYFSQPMVAAAVIVHLVTDGTYYGDQKQETISVQL LDTKDQSHDLGLHVLSCRNNPLIIPVVHDLSQPFYHSQAVRVSFSSPLVAI SGVALRSFDNFDPVTLSSCQRGETYSPAEQSCVHFACEKTDCPELAVENAS LNCSSSDRYHGAQCTVSCRTGYVLQIRRDDELIKSQTGPSVTVTCTEGKWN KQVACEPVDCSIPDHHQVYAASFSCPEGTTFGSQCSFQCRHPAQLKGNNSL LTCMEDGLWSFPEALCELMCLAPPPVPNADLQTARCRENKHKVGSFCKYKC KPGYHVPGSSRKSKKRAFKTQCTQDGSWQEGACVPVTCDPPPPKFHGLYQC TNGFQFNSECRIKCEDSDASQGLGSNVIHCRKDGTWNGSFHVCQEMQGQCS VPNELNSNLKLQCPDGYAIGSECATSCLDHNSESIILPMNVTVRDIPHWLN PTRVERVVCTAGLKWYPHPALIHCVKGCEPFMGDNYCDAINNRAFCNYDGG DCCTSTVKTKKVTPFPMSCDLQGDCACRDPQAQEHSRKDLRGYSHG |

TABLE J

Heavy and light chain nucleic acid sequences of antibodies 1-6

| SEQ ID NO: | Clone Name | Antibody Region | Sequence |
|---|---|---|---|
| 80 | Ab1 | Heavy Chain, DNA | GAGGTGCAGCTGGTGGAGTCTGGTGGAGGCGTGGTCCAGCCT GGGCGCTCCCTGAGACTCTCCTGTGCAGCCTCTGGATTCACCT TCAGTAGCTATGCCATGCACTGGGTCCGCCAGGCTCCAGGCAA GGGTCTGGAGTGGGTGGCAGTGATATCCTACGATGGAAGCAT CAAGTACTATGCAGACGCCGTGAAGGGCCGATTCACCATCTCC |

TABLE J-continued

Heavy and light chain nucleic acid sequences of antibodies 1-6

| SEQ ID NO: | Clone Name | Antibody Region | Sequence |
|---|---|---|---|
| | | | AGAGACAATTCCAAGAACACGCTGTATCTGCAAATGAACAGC CTGAGAGCTGAGGACACGGCCGTGTATTACTGTGCGAGACAC AACCGCATCTACTCCTGGGGCTGGCACACCTTTGACATCTGGG GCCAAGGAACCCTGGTCACCGTCTCCTCAGCGTCGACCAAGG GCCCATCGGTCTTCCCCCTGGCACCCTCCTCCAAGAGCACCTC TGGGGGCACAGCGGCCCTGGGCTGCCTGGTCAAGGACTACTT CCCCGAACCGGTGACGGTGTCGTGGAACTCAGGCGCCCTGAC CAGCGGCGTGCACACCTTCCCGGCTGTCCTACAGTCCTCAGGA CTCTACTCCCTCAGCAGCGTGGTGACCGTGCCCTCCAGCAGCT TGGGCACCCAGACCTACATCTGCAACGTGAATCACAAGCCCA GCAACACCAAGGTGGACAAGAAAGTTGAGCCCAAATCTTGTG ACAAAACTCACACATGCCCACCGTGCCCAGCACCTGAAGCCG CGGGGGGACCGTCAGTCTTCCTCTTCCCCCCAAAACCCAAGGA CACCCTCATGATCTCCCGGACCCCTGAGGTCACATGCGTGGTG GTGGACGTGAGCCACGAAGACCCTGAGGTCAAGTTCAACTGG TACGTGGACGGCGTGGAGGTGCATAATGCCAAGACAAAGCCG CGGGAGGAGCAGTACAACAGCACGTACCGTGTGGTCAGCGTC CTCACCGTCCTGCACCAGGACTGGCTGAATGGCAAGGAGTAC AAGTGCAAGGTCTCCAACAAAGCCCTCCCAGCCCCCATCGAG AAAACCATCTCCAAAGCCAAAGGGCAGCCCCGAGAACCACAG GTGTACACCCTGCCCCCATCCCGCGAGGAGATGACCAAGAAC CAGGTCAGCCTGACCTGCCTGGTCAAAGGCTTCTATCCCAGCG ACATCGCCGTGGAGTGGGAGAGCAATGGGCAGCCGGAGAACA ACTACAAGACCACGCCTCCCGTGCTGGACTCCGACGGCTCCTT CTTCCTCTACAGCAAGCTCACCGTGGACAAGAGCAGGTGGCA GCAGGGGAACGTCTTCTCATGCTCCGTGATGCATGAGGCTCTG CACAACCACTACACGCAGAAGAGCCTCTCCCTGTCTCCGGGTA AA |
| 81 | Ab1 | Heavy Chain, Variable Region, DNA | GAGGTGCAGCTGGTGGAGTCTGGTGGAGGCGTGGTCCAGCCT GGGCGCTCCCTGAGACTCTCCTGTGCAGCCTCTGGATTCACCT TCAGTAGCTATGCCATGCACTGGGTCCGCCAGGCTCCAGGCAA GGGTCTGGAGTGGGTGGCAGTGATATCCTACGATGGAAGCAT CAAGTACTATGCAGACGCCGTGAAGGGCCGATTCACCATCTCC AGAGACAATTCCAAGAACACGCTGTATCTGCAAATGAACAGC CTGAGAGCTGAGGACACGGCCGTGTATTACTGTGCGAGACAC AACCGCATCTACTCCTGGGGCTGGCACACCTTTGACATCTGGG GCCAAGGAACCCTGGTCACCGTCTCCTCA |
| 82 | Ab1 | Light Chain, DNA | GACATCCAGATGACCCAGTCTCCATCCTCCCTGTCTGCATCTG TAGGAGACAGAGTCACCATCACTTGCCGGGCAAGTCAGGACA TTAGCATATATTTAAACTGGTATCAGCAGAAACCAGGGAAAG CTCCTAAGCTCCTGATCTATGGCGCATCCAGCTTGCAGAGTGG TGTCCCATCACGCTTCAGTGGCAGTGGATCTGGGACAGATTTC ACTCTCACCATCAGCAGTCTGCAACCTGAAGATTTCGCAACTT ACTACTGTCAGCAGGCCGACGCGGGGCCTTGGAAGTTCGGCG GAGGGACCAAGGTGGAGATCAAACGTACGGTGGCTGCACCAT CTGTCTTCATCTTCCCGCCATCTGATGAGCAGTTGAAATCTGG AACTGCCTCTGTTGTGTGCCTGCTGAATAACTTCTATCCCAGA GAGGCCAAAGTACAGTGGAAGGTGGATAACGCCCTCCAATCG GGTAACTCCCAGGAGAGTGTCACAGAGCAGGACAGCAAGGAC AGCACCTACAGCCTCAGCAGCACCCTGACGCTGAGCAAAGCA GACTACGAGAAACACAAAGTCTACGCCTGCGAAGTCACCCAT CAGGGCCTGAGCTCGCCCGTCACAAAGAGCTTCAACAGGGGA GAGTGT |
| 83 | Ab1 | Light Chain, Variable Region, DNA | GACATCCAGATGACCCAGTCTCCATCCTCCCTGTCTGCATCTG TAGGAGACAGAGTCACCATCACTTGCCGGGCAAGTCAGGACA TTAGCATATATTTAAACTGGTATCAGCAGAAACCAGGGAAAG CTCCTAAGCTCCTGATCTATGGCGCATCCAGCTTGCAGAGTGG TGTCCCATCACGCTTCAGTGGCAGTGGATCTGGGACAGATTTC ACTCTCACCATCAGCAGTCTGCAACCTGAAGATTTCGCAACTT ACTACTGTCAGCAGGCCGACGCGGGGCCTTGGAAGTTCGGCG GAGGGACCAAGGTGGAGATCAAA |
| 84 | Ab2 | Heavy Chain, DNA | GCCTCTGGATTCACCTTCAGTAGCTATGCCATGCACTGGGTCC GCCAGGCTCCAGGCAAGGGTCTGGAGTGGGTGGCAGTGATAT CCTACGATGGAAGCATCAAGTACTATGCAGACGCCGTGAAGG GCCGATTCACCATCTCCAGAGACAATTCCAAGAACACGCTGTA TCTGCAAATGAACAGCCTGAGAGCTGAGGACACGGCCGTGTA TTACTGTGCGAGACACGAGCGCATCCCCCCTGGGGGTTTCAC ACCTTTGACATCTGGGGCCAAGGAACCCTGGTCACCGTCTCCT CAGCGTCGACCAAGGGCCCATCGGTCTTCCCCCTGGCACCCTC CTCCAAGAGCACCTCTGGGGGCACAGCGGCCCTGGGCTGCCT |

TABLE J-continued

Heavy and light chain nucleic acid sequences of antibodies 1-6

| SEQ ID NO: | Clone Name | Antibody Region | Sequence |
|---|---|---|---|
| | | | GGTCAAGGACTACTTCCCCGAACCGGTGACGGTGTCGTGGAA CTCAGGCGCCCTGACCAGCGGCGTGCACACCTTCCCGGCTGTC CTACAGTCCTCAGGACTCTACTCCCTCAGCAGCGTGGTGACCG TGCCCTCCAGCAGCTTGGGCACCCAGACCTACATCTGCAACGT GAATCACAAGCCCAGCAACACCAAGGTGGACAAGAAAGTTGA GCCCAAATCTTGTGACAAAACTCACACATGCCCACCGTGCCCA GCACCTGAAGCCGCGGGGGGACCGTCAGTCTTCCTCTTCCCCC CAAAACCCAAGGACACCCTCATGATCTCCCGGACCCCTGAGG TCACATGCGTGGTGGTGGACGTGAGCCACGAAGACCCTGAGG TCAAGTTCAACTGGTACGTGGACGGCGTGGAGGTGCATAATG CCAAGACAAAGCCGCGGGAGGAGCAGTACAACAGCACGTACC GTGTGGTCAGCGTCCTCACCGTCCTGCACCAGGACTGGCTGAA TGGCAAGGAGTACAAGTGCAAGGTCTCCAACAAAGCCCTCCC AGCCCCCATCGAGAAAACCATCTCCAAAGCCAAAGGGCAGCC CCGAGAACCACAGGTGTACACCCTGCCCCCATCCCGCGAGGA GATGACCAAGAACCAGGTCAGCCTGACCTGCCTGGTCAAAGG CTTCTATCCCAGCGACATCGCCGTGGAGTGGGAGAGCAATGG GCAGCCGGAGAACAACTACAAGACCACGCCTCCCGTGCTGGA CTCCGACGGCTCCTTCTTCCTCTACAGCAAGCTCACCGTGGAC AAGAGCAGGTGGCAGCAGGGGAACGTCTTCTCATGCTCCGTG ATGCATGAGGCTCTGCACAACCACTACACGCAGAAGAGCCTC TCCCTGTCTCCGGGTAAA |
| 85 | Ab2 | Heavy Chain, Variable Region, DNA | GCCTCTGGATTCACCTTCAGTAGCTATGCCATGCACTGGGTCC GCCAGGCTCCAGGCAAGGGTCTGGAGTGGGTGGCAGTGATAT CCTACGATGGAAGCATCAAGTACTATGCAGACGCCGTGAAGG GCCGATTCACCATCTCCAGAGACAATTCCAAGAACACGCTGTA TCTGCAAATGAACAGCCTGAGAGCTGAGGACACGGCCGTGTA TTACTGTGCGAGACACGAGCGCATCCCCCCCTGGGGGTTTCAC ACCTTTGACATCTGGGGCCAAGGAACCCTGGTCACCGTCTCCT CA |
| 86 | Ab2 | Light Chain, DNA | GACATCCAGATGACCCAGTCTCCATCCTCCCTGTCTGCATCTG TAGGAGACAGAGTCACCATCACTTGCCGGGCAAGTCAGGGCA TTAGCATTTATTTAAACTGGTATCAGCAGAAACCAGGGAAAG CTCCTAAGCTCCTGATCTATGGCGCATCCAGCTTGCAGAGTGG TGTCCCATCACGCTTCAGTGGCAGTGGATCTGGGACAGATTTC ACTCTCACCATCAGCAGTCTGCAACCTGAAGATTTCGCAACTT ACTACTGTCAACAGAGTGACGGCACCCCTTGGACTTTCGGCGG AGGGACCAAGGTGGAGATCAAACGTACGGTGGCTGCACCATC TGTCTTCATCTTCCCGCCATCTGATGAGCAGTTGAAATCTGGA ACTGCCTCTGTTGTGTGCCTGCTGAATAACTTCTATCCCAGAG AGGCCAAAGTACAGTGGAAGGTGGATAACGCCCTCCAATCGG GTAACTCCCAGGAGAGTGTCACAGAGCAGGACAGCAAGGACA GCACCTACAGCCTCAGCAGCACCCTGACGCTGAGCAAAGCAG ACTACGAGAAACACAAAGTCTACGCCTGCGAAGTCACCCATC AGGGCCTGAGCTCGCCCGTCACAAAGAGCTTCAACAGGGGAG AGTGT |
| 87 | Ab2 | Light Chain, Variable Region, DNA | GACATCCAGATGACCCAGTCTCCATCCTCCCTGTCTGCATCTG TAGGAGACAGAGTCACCATCACTTGCCGGGCAAGTCAGGGCA TTAGCATTTATTTAAACTGGTATCAGCAGAAACCAGGGAAAG CTCCTAAGCTCCTGATCTATGGCGCATCCAGCTTGCAGAGTGG TGTCCCATCACGCTTCAGTGGCAGTGGATCTGGGACAGATTTC ACTCTCACCATCAGCAGTCTGCAACCTGAAGATTTCGCAACTT ACTACTGTCAACAGAGTGACGGCACCCCTTGGACTTTCGGCGG AGGGACCAAGGTGGAGATCAAA |
| 88 | Ab3 | Heavy Chain, DNA | GAGGTGCAGCTGGTGGAGTCTGGTGGAGGCGTGGTCCAGCCT GGGCGCTCCCTGAGACTCTCCTGTGCAGCCTCTGGATTCACCT TCAGTAGCTATGGGATGCACTGGGTCCGCCAGGCTCCAGGCA AGGGTCTGGAGTGGGTGGCAGTCATATCCTACGATGGACGCA ACAAGTACTATGCAGACGCCGTGAAGGGCCGATTCACCATCT CCAGAGACAATTCCAAGAACACGCTGTATCTGCAAATGAACA GCCTGAGAGCTGAGGACACGGCCGTGTATTACTGTGCGAGAT ACAAGCCCATGCCCTTTGACGTCTGGGGCCAAGGAACCCTGGT CACCGTCTCCTCAGCGTCGACCAAGGGCCCATCGGTCTTCCCC CTGGCACCCTCCTCAAGAGCACCTCTGGGGGCACAGCGGCC CTGGGCTGCCTGGTCAAGGACTACTTCCCCGAACCGGTGACGG TGTCGTGGAACTCAGGCGCCCTGACCAGCGGCGTGCACACCTT CCCGGCTGTCCTACAGTCCTCAGGACTCTACTCCCTCAGCAGC GTGGTGACCGTGCCCTCCAGCAGCTTGGGCACCCAGACCTACA TCTGCAACGTGAATCACAAGCCCAGCAACACCAAGGTGGACA AGAAAGTTGAGCCCAAATCTTGTGACAAAACTCACACATGCC |

TABLE J-continued

Heavy and light chain nucleic acid sequences of antibodies 1-6

| SEQ ID NO: | Clone Name | Antibody Region | Sequence |
|---|---|---|---|
|  |  |  | CACCGTGCCCAGCACCTGAAGCCGCGGGGGGACCGTCAGTCT<br>TCCTCTTCCCCCCAAAACCCAAGGACACCCTCATGATCTCCCG<br>GACCCCTGAGGTCACATGCGTGGTGGTGGACGTGAGCCACGA<br>AGACCCTGAGGTCAAGTTCAACTGGTACGTGGACGGCGTGGA<br>GGTGCATAATGCCAAGACAAAGCCGCGGGAGGAGCAGTACAA<br>CAGCACGTACCGTGTGGTCAGCGTCCTCACCGTCCTGCACCAG<br>GACTGGCTGAATGGCAAGGAGTACAAGTGCAAGGTCTCCAAC<br>AAAGCCCTCCCAGCCCCCATCGAGAAAACCATCTCCAAAGCC<br>AAAGGGCAGCCCCGAGAACCACAGGTGTACACCCTGCCCCCA<br>TCCCGCGAGGAGATGACCAAGAACCAGGTCAGCCTGACCTGC<br>CTGGTCAAAGGCTTCTATCCCAGCGACATCGCCGTGGAGTGGG<br>AGAGCAATGGGCAGCCGGAGAACAACTACAAGACCACGCCTC<br>CCGTGCTGGACTCCGACGGCTCCTTCTTCCTCTACAGCAAGCT<br>CACCGTGGACAAGAGCAGGTGGCAGCAGGGGAACGTCTTCTC<br>ATGCTCCGTGATGCATGAGGCTCTGCACAACCACTACACGCAG<br>AAGAGCCTCTCCCTGTCTCCGGGTAAA |
| 89 | Ab3 | Heavy Chain, Variable Region, DNA | GAGGTGCAGCTGGTGGAGTCTGGTGGAGGCGTGGTCCAGCCT<br>GGGCGCTCCCTGAGACTCTCCTGTGCAGCCTCTGGATTCACCT<br>TCAGTAGCTATGGGATGCACTGGGTCCGCCAGGCTCCAGGCA<br>AGGGTCTGGAGTGGGTGGCAGTCATATCCTACGATGGACGCA<br>ACAAGTACTATGCAGACGCCGTGAAGGGCCGATTCACCATCT<br>CCAGAGACAATTCCAAGAACACGCTGTATCTGCAAATGAACA<br>GCCTGAGAGCTGAGGACACGGCCGTGTATTACTGTGCGAGAT<br>ACAAGCCCATGCCCTTTGACGTCTGGGGCCAAGGAACCCTGGT<br>CACCGTCTCCTCA |
| 90 | Ab3 | Light Chain, DNA | GACATCCAGATGACCCAGTCTCCATCCTCCCTGTCTGCATCTG<br>TAGGAGACAGAGTCACCATCACTTGCCGGGCAAGTCAGAGCA<br>TTAGCAGCTATTTAAACTGGTATCAGCAGAAACCAGGGAAAG<br>CTCCTAAGCTCCTGATCTATGAGGCATCCATATTGCAGAGTGG<br>TGTCCCATCACGCTTCAGTGGCAGTGGATCTGGGACAGATTTC<br>ACTCTCACCATCAGCAGTCTGCAACCTGAAGATTTCGCAACTT<br>ACTACTGTGGGCAGAGCTACTACACCCCTTTCCCGTTCGGCGG<br>AGGGACCAAGGTGGAGATCAAACGTACGGTGGCTGCACCATC<br>TGTCTTCATCTTCCCGCCATCTGATGAGCAGTTGAAATCTGGA<br>ACTGCCTCTGTTGTGTGCCTGCTGAATAACTTCTATCCCAGAG<br>AGGCCAAAGTACAGTGGAAGGTGGATAACGCCCTCCAATCGG<br>GTAACTCCCAGGAGAGTGTCACAGAGCAGGACAGCAAGGACA<br>GCACCTACAGCCTCAGCAGCACCCTGACGCTGAGCAAAGCAG<br>ACTACGAGAAACACAAAGTCTACGCCTGCGAAGTCACCCATC<br>AGGGCCTGAGCTCGCCCGTCACAAAGAGCTTCAACAGGGGAG<br>AGTGT |
| 91 | Ab3 | Light Chain, Variable Region, DNA | GACATCCAGATGACCCAGTCTCCATCCTCCCTGTCTGCATCTG<br>TAGGAGACAGAGTCACCATCACTTGCCGGGCAAGTCAGAGCA<br>TTAGCAGCTATTTAAACTGGTATCAGCAGAAACCAGGGAAAG<br>CTCCTAAGCTCCTGATCTATGAGGCATCCATATTGCAGAGTGG<br>TGTCCCATCACGCTTCAGTGGCAGTGGATCTGGGACAGATTTC<br>ACTCTCACCATCAGCAGTCTGCAACCTGAAGATTTCGCAACTT<br>ACTACTGTGGGCAGAGCTACTACACCCCTTTCCCGTTCGGCGG<br>AGGGACCAAGGTGGAGATCAAA |
| 92 | Ab4 | Heavy Chain, DNA | GAGGTGCAGCTGGTGGAGTCTGGTGGAGGCGTGGTCCAGCCT<br>GGGCGCTCCCTGAGACTCTCCTGTGCAGCCTCTGGATTCGCGT<br>TCAGCACCTATGGGATGCACTGGGTCCGCCAGGCTCCAGGCA<br>AGGGTCTGGAGTGGGTGGCAGTGATAAGGTACGACGGACAGG<br>AGAAGTACTATGCAGACGCCGTGAAGGGCCGATTCACCATCT<br>CCAGAGACAATTCCAAGAACACGCTGTATCTGCAAATGAACA<br>GCCTGAGAGCTGAGGACACGGCCGTGTATTACTGTGCGAGAT<br>ACAAGCCCATGCCCTTTGACGTCTGGGGCCAAGGAACCCTGGT<br>CACCGTCTCCTCAGCGTCGACCAAGGGCCCATCGGTCTTCCCC<br>CTGGCACCCTCCTCCAAGAGCACCTCTGGGGGCACAGCGGCC<br>CTGGGCTGCCTGGTCAAGGACTACTTCCCCGAACCGGTGACGG<br>TGTCGTGGAACTCAGGCGCCCTGACCAGCGGCGTGCACACCTT<br>CCCGGCTGTCCTACAGTCCTCAGGACTCTACTCCCTCAGCAGC<br>GTGGTGACCGTGCCCTCCAGCAGCTTGGGCACCCAGACCTACA<br>TCTGCAACGTGAATCACAAGCCCAGCAACACCAAGGTGGACA<br>AGAAAGTTGAGCCCAAATCTTGTGACAAAACTCACACATGCC<br>CACCGTGCCCAGCACCTGAAGCCGCGGGGGGACCGTCAGTCT<br>TCCTCTTCCCCCCAAAACCCAAGGACACCCTCATGATCTCCCG<br>GACCCCTGAGGTCACATGCGTGGTGGTGGACGTGAGCCACGA<br>AGACCCTGAGGTCAAGTTCAACTGGTACGTGGACGGCGTGGA<br>GGTGCATAATGCCAAGACAAAGCCGCGGGAGGAGCAGTACAA |

TABLE J-continued

Heavy and light chain nucleic
acid sequences of antibodies 1-6

| SEQ ID NO: | Clone Name | Antibody Region | Sequence |
|---|---|---|---|
| | | | CAGCACGTACCGTGTGGTCAGCGTCCTCACCGTCCTGCACCAG
GACTGGCTGAATGGCAAGGAGTACAAGTGCAAGGTCTCCAAC
AAAGCCCTCCCAGCCCCCATCGAGAAAACCATCTCCAAAGCC
AAAGGGCAGCCCCGAGAACCACAGGTGTACACCCTGCCCCCA
TCCCGCGAGGAGATGACCAAGAACCAGGTCAGCCTGACCTGC
CTGGTCAAAGGCTTCTATCCCAGCGACATCGCCGTGGAGTGGG
AGAGCAATGGGCAGCCGGAGAACAACTACAAGACCACGCCTC
CCGTGCTGGACTCCGACGGCTCCTTCTTCCTCTACAGCAAGCT
CACCGTGGACAAGAGCAGGTGGCAGCAGGGGAACGTCTTCTC
ATGCTCCGTGATGCATGAGGCTCTGCACAACCACTACACGCAG
AAGAGCCTCTCCCTGTCTCCGGGTAAA |
| 93 | Ab4 | Heavy Chain, Variable Region, DNA | GAGGTGCAGCTGGTGGAGTCTGGTGGAGGCGTGGTCCAGCCT
GGGCGCTCCCTGAGACTCTCCTGTGCAGCCTCTGGATTCGCGT
TCAGCACCTATGGGATGCACTGGGTCCGCCAGGCTCCAGGCA
AGGGTCTGGAGTGGGTGGCAGTGATAAGGTACGACGGACAGG
AGAAGTACTATGCAGACGCCGTGAAGGGCCGATTCACCATCT
CCAGAGACAATTCCAAGAACACGCTGTATCTGCAAATGAACA
GCCTGAGAGCTGAGGACACGGCCGTGTATTACTGTGCGAGAT
ACAAGCCCATGCCCTTTGACGTCTGGGGCCAAGGAACCCTGGT
CACCGTCTCCTCA |
| 94 | Ab4 | Light Chain, DNA | GACATCCAGATGACCCAGTCTCCATCCTCCCTGTCTGCATCTG
TAGGAGACAGAGTCACCATCACTTGCCGGGCAAGTCAGAGCA
TTAGCAGGTATTTAAACTGGTATCAGCAGAAACCAGGGAAAG
CTCCTAAGCTCCTGATCTATGCGGCATCCATCTTGCAGAGTGG
TGTCCCATCACGCTTCAGTGGCAGTGGATCTGGGACAGATTTC
ACTCTCACCATCAGCAGTCTGCAACCTGAAGATTTCGCAACTT
ACTACTGTCAACAGAGTCACCCCACGCCTTTCACTTTCGGCGG
AGGGACCAAGGTGGAGATCAAACGTACGGTGGCTGCACCATC
TGTCTTCATCTTCCCGCCATCTGATGAGCAGTTGAAATCTGGA
ACTGCCTCTGTTGTGTGCCTGCTGAATAACTTCTATCCCAGAG
AGGCCAAAGTACAGTGGAAGGTGGATAACGCCCTCCAATCGG
GTAACTCCCAGGAGAGTGTCACAGAGCAGGACAGCAAGGACA
GCACCTACAGCCTCAGCAGCACCCTGACGCTGAGCAAAGCAG
ACTACGAGAAACACAAAGTCTACGCCTGCGAAGTCACCCATC
AGGGCCTGAGCTCGCCCGTCACAAAGAGCTTCAACAGGGGAG
AGTGT |
| 95 | Ab4 | Light Chain, Variable Region, DNA | GACATCCAGATGACCCAGTCTCCATCCTCCCTGTCTGCATCTG
TAGGAGACAGAGTCACCATCACTTGCCGGGCAAGTCAGAGCA
TTAGCAGGTATTTAAACTGGTATCAGCAGAAACCAGGGAAAG
CTCCTAAGCTCCTGATCTATGCGGCATCCATCTTGCAGAGTGG
TGTCCCATCACGCTTCAGTGGCAGTGGATCTGGGACAGATTTC
ACTCTCACCATCAGCAGTCTGCAACCTGAAGATTTCGCAACTT
ACTACTGTCAACAGAGTCACCCCACGCCTTTCACTTTCGGCGG
AGGGACCAAGGTGGAGATCAAA |
| 96 | Ab5 | Heavy Chain, DNA | GAGGTGCAGCTGGTGGAGTCTGGTGGAGGCGTGGTCCAGCCT
GGGCGCTCCCTGAGACTCTCCTGTGCAGCCTCTGGATTCACCT
TCAGTAGCTATGGGATGCACTGGGTCCGCCAGGCTCCAGGCA
AGGGTCTGGAGTGGGTGGCAGTCATATACTACGATGGACGCC
GCAAGTACTATGCAGACTCCGTGAAGGGCCGATTCACCATCTC
CAGAGACAATTCCAAGAACACGCTGTATCTGCAAATGAACAG
CCTGAGAGCTGAGGACACGGCTGTGTATTACTGTGCGAGAGC
CGACATGCACCGCTTTGACGTCTGGGGCCAAGGAACCCTGGTC
ACCGTCTCCTCAGCGTCGACCAAGGGCCCATCGGTCTTCCCCC
TGGCACCCTCCTCCAAGAGCACCTCTGGGGGCACAGCGGCCCT
GGGCTGCCTGGTCAAGGACTACTTCCCCGAACCGGTGACGGT
GTCGTGGAACTCAGGCGCCCTGACCAGCGGCGTGCACACCTTC
CCGGCTGTCCTACAGTCCTCAGGACTCTACTCCCTCAGCAGCG
TGGTGACCGTGCCCTCCAGCAGCTTGGGCACCCAGACCTACAT
CTGCAACGTGAATCACAAGCCCAGCAACACCAAGGTGGACAA
GAAAGTTGAGCCCAAATCTTGTGACAAAACTCACACATGCCC
ACCGTGCCCAGCACCTGAAGCGCGCGGGGGACCGTCAGTCTT
CCTCTTCCCCCCAAAACCCAAGGACACCCTCATGATCTCCCGG
ACCCCTGAGGTCACATGCGTGGTGGTGGACGTGAGCCACGAA
GACCCTGAGGTCAAGTTCAACTGGTACGTGGACGGCGTGGAG
GTGCATAATGCCAAGACAAAGCCGCGGGAGGAGCAGTACAAC
AGCACGTACCGTGTGGTCAGCGTCCTCACCGTCCTGCACCAGG
ACTGGCTGAATGGCAAGGAGTACAAGTGCAAGGTCTCCAACA
AAGCCCTCCCAGCCCCCATCGAGAAAACCATCTCCAAAGCCA
AAGGGCAGCCCCGAGAACCACAGGTGTACACCCTGCCCCCAT
CCCGCGAGGAGATGACCAAGAACCAGGTCAGCCTGACCTGCC |

TABLE J-continued

Heavy and light chain nucleic acid sequences of antibodies 1-6

| SEQ ID NO: | Clone Name | Antibody Region | Sequence |
|---|---|---|---|
| | | | TGGTCAAAGGCTTCTATCCCAGCGACATCGCCGTGGAGTGGG<br>AGAGCAATGGGCAGCCGGAGAACAACTACAAGACCACGCCTC<br>CCGTGCTGGACTCCGACGGCTCCTTCTTCCTCTACAGCAAGCT<br>CACCGTGGACAAGAGCAGGTGGCAGCAGGGGAACGTCTTCTC<br>ATGCTCCGTGATGCATGAGGCTCTGCACAACCACTACACGCAG<br>AAGAGCCTCTCCCTGTCTCCGGGTAAA |
| 97 | Ab5 | Heavy Chain, Variable Region, DNA | GAGGTGCAGCTGGTGGAGTCTGGTGGAGGCGTGGTCCAGCCT<br>GGGCGCTCCCTGAGACTCTCCTGTGCAGCCTCTGGATTCACCT<br>TCAGTAGCTATGGGATGCACTGGGTCCGCCAGGCTCCAGGCA<br>AGGGTCTGGAGTGGGTGGCAGTCATATACTACGATGGACGCC<br>GCAAGTACTATGCAGACTCCGTGAAGGGCCGATTCACCATCTC<br>CAGAGACAATTCCAAGAACACGCTGTATCTGCAAATGAACAG<br>CCTGAGAGCTGAGGACACGGCTGTGTATTACTGTGCGAGAGC<br>CGACATGCACCGCTTTGACGTCTGGGGCCAAGGAACCCTGGTC<br>ACCGTCTCCTCA |
| 98 | Ab5 | Light Chain, DNA | GACATCCAGATGACCCAGTCTCCATCCTCCCTGTCTGCATCTG<br>TAGGAGACAGAGTCACCATCACTTGCCGGGCAAGTCAGGACA<br>TTATCAGCTATTTAAACTGGTATCAGCAGAAACCAGGGAAAG<br>CTCCTAAGCTCCTGATCTATGTGGCATCCAGCTTGCAGAGTGG<br>TGTCCCATCACGCTTCAGTGGCAGTGGATCTGGGACAGATTTC<br>ACTCTCACCATCAGCAGTCTGCAACCTGAAGATTTCGCAACTT<br>ACTACTGTCAACAGAGTTACAGCCCGCCTTACACTTTCGGCGG<br>AGGGACCAAGGTGGAGATCAAACGTACGGTGGCTGCACCATC<br>TGTCTTCATCTTCCCGCCATCTGATGAGCAGTTGAAATCTGGA<br>ACTGCCTCTGTTGTGTGCCTGCTGAATAACTTCTATCCCAGAG<br>AGGCCAAAGTACAGTGGAAGGTGGATAACGCCCTCCAATCGG<br>GTAACTCCCAGGAGAGTGTCACAGAGCAGGACAGCAAGGACA<br>GCACCTACAGCCTCAGCAGCACCCTGACGCTGAGCAAAGCAG<br>ACTACGAGAAACACAAAGTCTACGCCTGCGAAGTCACCCATC<br>AGGGCCTGAGCTCGCCCGTCACAAAGAGCTTCAACAGGGGAG<br>AGTGT |
| 99 | Ab5 | Light Chain, Variable Region, DNA | GACATCCAGATGACCCAGTCTCCATCCTCCCTGTCTGCATCTG<br>TAGGAGACAGAGTCACCATCACTTGCCGGGCAAGTCAGGACA<br>TTATCAGCTATTTAAACTGGTATCAGCAGAAACCAGGGAAAG<br>CTCCTAAGCTCCTGATCTATGTGGCATCCAGCTTGCAGAGTGG<br>TGTCCCATCACGCTTCAGTGGCAGTGGATCTGGGACAGATTTC<br>ACTCTCACCATCAGCAGTCTGCAACCTGAAGATTTCGCAACTT<br>ACTACTGTCAACAGAGTTACAGCCCGCCTTACACTTTCGGCGG<br>AGGGACCAAGGTGGAGATCAAA |
| 100 | Ab6 | Heavy Chain, DNA | GAGGTGCAGCTGTTGGAGTCTGGTGGAGGCTTGGTACAGCCT<br>GGTGGATCCCTGAGACTCTCCTGTGCAGCCTCTGGATTCACCT<br>TTAGCAGCTACGCGATGAGCTGGGTCCGCCAGGCTCCAGGGA<br>AGGGTCTGGAGTGGGTCTCAGCCATCAGTATGACCGTGGGTC<br>GCACATACTACGCAGACTCCGTGAAGGGCCGGTTCACCATCTC<br>CAGAGACAATTCCAAGAACACGCTGTATCTGCAAATGAACAG<br>CCTGAGAGCCGAGGACACGGCCGTGTATTACTGTGCGAGAGT<br>GTGGGGCGGCGTGCGCTTTGACGTCTGGGGCCAAGGAACCCT<br>GGTCACCGTCTCCTCAGCGTCGACCAAGGGCCCATCGGTCTTC<br>CCCCTGGCACCCTCCTCCAAGAGCACCTCTGGGGGCACAGCG<br>GCCCTGGGCTGCCTGGTCAAGGACTACTTCCCCGAACCGGTGA<br>CGGTGTCGTGGAACTCAGGCGCCCTGACCAGCGGCGTGCACA<br>CCTTCCCGGCTGTCCTACAGTCCTCAGGACTCTACTCCCTCAG<br>CAGCGTGGTGACCGTGCCCTCCAGCAGCTTGGGCACCCAGAC<br>CTACATCTGCAACGTGAATCACAAGCCCAGCAACACCAAGGT<br>GGACAAGAAAGTTGAGCCCAAATCTTGTGACAAAACTCACAC<br>ATGCCCACCGTGCCCAGCACCTGAAGCCGCGGGGGGACCGTC<br>AGTCTTCCTCTTCCCCCCAAAACCCAAGGACACCCTCATGATC<br>TCCCGGACCCCTGAGGTCACATGCGTGGTGGTGGACGTGAGC<br>CACGAAGACCCTGAGGTCAAGTTCAACTGGTACGTGGACGGC<br>GTGGAGGTGCATAATGCCAAGACAAAGCCGCGGGAGGAGCA<br>GTACAACAGCACGTACCGTGTGGTCAGCGTCCTCACCGTCCTG<br>CACCAGGACTGGCTGAATGGCAAGGAGTACAAGTGCAAGGTC<br>TCCAACAAAGCCCTCCCAGCCCCCATCGAGAAAACCATCTCCA<br>AAGCCAAAGGGCAGCCCCGAGAACCACAGGTGTACACCCTGC<br>CCCCATCCCGCGAGGAGATGACCAAGAACCAGGTCAGCCTGA<br>CCTGCCTGGTCAAAGGCTTCTATCCCAGCGACATCGCCGTGGA<br>GTGGGAGAGCAATGGGCAGCCGGAGAACAACTACAAGACCA<br>CGCCTCCCGTGCTGGACTCCGACGGCTCCTTCTTCCTCTACAG |

TABLE J-continued

Heavy and light chain nucleic
acid sequences of antibodies 1-6

| SEQ ID NO: | Clone Name | Antibody Region | Sequence |
|---|---|---|---|
| | | | CAAGCTCACCGTGGACAAGAGCAGGTGGCAGCAGGGGAACGT<br>CTTCTCATGCTCCGTGATGCATGAGGCTCTGCACAACCACTAC<br>ACGCAGAAGAGCCTCTCCCTGTCTCCGGGTAAA |
| 101 | Ab6 | Heavy Chain, Variable Region, DNA | GAGGTGCAGCTGTTGGAGTCTGGTGGAGGCTTGGTACAGCCT<br>GGTGGATCCCTGAGACTCTCCTGTGCAGCCTCTGGATTCACCT<br>TTAGCAGCTACGCGATGAGCTGGGTCCGCCAGGCTCCAGGGA<br>AGGGTCTGGAGTGGGTCTCAGCCATCAGTATGACCGTGGGTC<br>GCACATACTACGCAGACTCCGTGAAGGGCCGGTTCACCATCTC<br>CAGAGACAATTCCAAGAACACGCTGTATCTGCAAATGAACAG<br>CCTGAGAGCCGAGGACACGGCCGTGTATTACTGTGCGAGAGT<br>GTGGGGCGGCGTGCGCTTTGACGTCTGGGGCCAAGGAACCCT<br>GGTCACCGTCTCCTCA |
| 102 | Ab6 | Light Chain, DNA | GACATCCAGATGACCCAGTCTCCATCCTCCCTGTCTGCATCTG<br>TAGGAGACAGAGTCACCATCACTTGCCGGGCAAGTCAGAGCA<br>TTAGCACCTATTTAAACTGGTATCAGCAGAAACCAGGGAAAG<br>CTCCTAAGCTCCTGATCTATGTGGCATCCATCTTGCAGAGTGG<br>TGTCCCATCACGCTTCAGTGGCAGTGGATCTGGGACAGATTTC<br>ACTCTCACCATCAGCAGTCTGCAACCTGAAGATTTCGCAACTT<br>ACTACTGTCAACAGAGTTCCAGCACGCCTTGGACTTTCGGCGG<br>AGGGACCAAGGTGGAGATCAAACGTACGGTGGCTGCACCATC<br>TGTCTTCATCTTCCCGCCATCTGATGAGCAGTTGAAATCTGGA<br>ACTGCCTCTGTTGTGTGCCTGCTGAATAACTTCTATCCCAGAG<br>AGGCCAAAGTACAGTGGAAGGTGGATAACGCCCTCCAATCGG<br>GTAACTCCCAGGAGAGTGTCACAGAGCAGGACAGCAAGGACA<br>GCACCTACAGCCTCAGCAGCACCCTGACGCTGAGCAAAGCAG<br>ACTACGAGAAACACAAAGTCTACGCCTGCGAAGTCACCCATC<br>AGGGCCTGAGCTCGCCCGTCACAAAGAGCTTCAACAGGGGAG<br>AGTGT |
| 103 | Ab6 | Light Chain, Variable Region, DNA | GACATCCAGATGACCCAGTCTCCATCCTCCCTGTCTGCATCTG<br>TAGGAGACAGAGTCACCATCACTTGCCGGGCAAGTCAGAGCA<br>TTAGCACCTATTTAAACTGGTATCAGCAGAAACCAGGGAAAG<br>CTCCTAAGCTCCTGATCTATGTGGCATCCATCTTGCAGAGTGG<br>TGTCCCATCACGCTTCAGTGGCAGTGGATCTGGGACAGATTTC<br>ACTCTCACCATCAGCAGTCTGCAACCTGAAGATTTCGCAACTT<br>ACTACTGTCAACAGAGTTCCAGCACGCCTTGGACTTTCGGCGG<br>AGGGACCAAGGTGGAGATCAAA |

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. An isolated human antibody that binds to human Pregnancy Associated Plasma Protein A (PAPP-A) (SEQ ID NO: 79), wherein the antibody comprises a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein:

a. CDR-H1 comprises the sequence SYAMH (SEQ ID NO: 3);
b. CDR-H2 comprises the sequence VISYDGSIKYYA-DAVKG (SEQ ID NO: 4);
c. CDR-H3 comprises the sequence HNRIYSWGWHTFDI (SEQ ID NO: 5);
d. CDR-L1 comprises the sequence RASQDISIYLN (SEQ ID NO: 8);

e. CDR-L2 comprises the sequence GASSLQS (SEQ ID NO: 9); and f. CDR-L3 comprises the sequence QQADAGPWK (SEQ ID NO: 10).

2. The isolated human antibody of claim 1, wherein the VH sequence comprises the VH sequence set forth in SEQ ID NO: 2.

3. The isolated human antibody of claim 1, wherein the VL sequence comprises the VL sequence set forth in SEQ ID NO: 7.

4. The isolated human antibody of claim 1, wherein the VH sequence comprises the VH sequence set forth in SEQ ID NO: 2 and the VL sequence comprises the VL sequence set forth in SEQ ID NO: 7.

5. The isolated human antibody of claim 1, wherein the antibody comprises a heavy chain comprising the sequence set forth in SEQ ID NO: 1.

6. The isolated human antibody of claim 1, wherein the antibody comprises a light chain comprising the sequence set forth in SEQ ID NO: 6.

7. The isolated human antibody of claim 1, wherein the antibody comprises a heavy chain comprising the sequence set forth in SEQ ID NO: 1; and a light chain comprising the sequence set forth in SEQ ID NO: 6.

8. An isolated human antibody that binds to human Pregnancy Associated Plasma Protein A (PAPP-A) (SEQ ID NO: 79), wherein the antibody comprises two variable heavy chain (VH) sequences and two variable light chain (VL) sequences, wherein each of the VH sequences comprise the VH sequence set forth in SEQ ID NO: 2, and each of the VL sequences comprise the VL sequence set forth in SEQ ID NO: 7.

9. An isolated human antibody that binds to human Pregnancy Associated Plasma Protein A (PAPP-A) (SEQ ID NO: 79), wherein the antibody comprises a human IgG1 Fc region, two heavy chains each of which comprise the sequence set forth in SEQ ID NO: 1, and two light chains each of which comprise the sequence set forth in SEQ ID NO: 6.

* * * * *